US012679861B2

(12) United States Patent
Giusti et al.

(10) Patent No.: US 12,679,861 B2
(45) Date of Patent: Jul. 14, 2026

(54) PHOTOISOMERIZED COMPOSITIONS OF ANTHOCYANINS AND METHODS OF MAKING AND USE THEREOF

(71) Applicant: Ohio State Innovation Foundation, Columbus, OH (US)

(72) Inventors: M. Monica Giusti, Columbus, OH (US); Yucheng Zhou, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 1010 days.

(21) Appl. No.: 17/859,071

(22) Filed: Jul. 7, 2022

(65) Prior Publication Data
US 2023/0026978 A1     Jan. 26, 2023

Related U.S. Application Data

(60) Provisional application No. 63/219,054, filed on Jul. 7, 2021.

(51) Int. Cl.
| | |
|---|---|
| *C07H 17/065* | (2006.01) |
| *A23L 5/43* | (2016.01) |
| *A61K 8/60* | (2006.01) |
| *C07B 35/08* | (2006.01) |

(52) U.S. Cl.
CPC .............. *C07H 17/065* (2013.01); *A23L 5/43* (2016.08); *A61K 8/602* (2013.01); *C07B 35/08* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,421,618 A | 12/1983 | Salisbury | |
| 2005/0208139 A1* | 9/2005 | Hilt | A61K 9/06 514/651 |

FOREIGN PATENT DOCUMENTS

| | | | | |
|---|---|---|---|---|
| JP | H07242837 A | * | 9/1995 | C09B 61/00 |

OTHER PUBLICATIONS

Yoshida, K., Okuno, R., Kameda, K., Mori, M., & Kondo, T. (2003). Influence of E, Z-isomerization and stability of acylated anthocyanins under the UV irradiation. Biochemical engineering journal, 14(3), 163-169. (Year: 2003).*
Suga Test Instruments, Inc., UV fade meter 48AU (Year: 2025).*
Ahmadiani et al. Molar absorptivity (ε) and spectral characteristics of cyanidin-based anthocyanins from red cabbage. Food Chem, 2016, 197, 900-906.

Andersen, Ø., & Jordheim, M. (2005). The Anthocyanins. In Flavonoids. 81 pages. https://doi.org/10.1201/9781420039443. ch10.
Bakowska-Barczak. Acylated anthocyanins as stable, natural food colorants: A review. Polish J food Nutr Sci 2005, 14, 107-116.
Basílio N et al. Chemistry and Photochemistry of Anthocyanins and Related Compounds: A Thermodynamic and Kinetic Approach. Molecules. 2016, 21, 1502.
Brouillard R et al. The Hemiacetal-Cis-Chalcone Equilibrium of Malvin, a Natural Anthocyanin. Can. J. Chem. 1990, 68, 755-761.
Dou et al. (2003). Detailed dynamics of a complex photochemical reaction: Cis-trans photoisomerization of stilbene. Journal of Chemical Physics, 119(20), 10658-10666. https://doi.org/10.1063/1.1621621.
Eiro MJ et al. Anthocyanin Color Behavior and Stability during Storage: Effect of Intermolecular Copigmentation. J. Agric. Food Chem. 2002, 50(25), 7461-7466.
García-Beneytez et al. (2003). Analysis of grape and wine anthocyanins by HPLC-MS. Journal of Agricultural and Food Chemistry, 51(19), 5622-5629. https://doi.org/10.1021/jf030220.
George F et al . Influence of trans-cis isomerisation of coumaric acid substituents on colour variance and stabilisation in anthocyanins. Phytochem. 2001, 57, 791-795.
Giusti MM et al. Acylated Anthocyanins from Edible Sources and Their Applications in Food Systems. Biochem. Eng. J. 2003. 14(3), 217-225.
Giusti MM et al. Characterization and Measurement of Anthocyanins by UV-Visible Spectroscopy. In Handbook of Food Analytical Chemistry; 2001; vol. 2-2, pp. 19-31.
Gonzali et al. Anthocyanins from Purple Tomatoes as novel Antioxidants to Promote Human Health. Antioxidants, 2020, 9(10), 1017.
Hayashi K et al. Photo-Isomerization of the Nasunin , the Ma Jor Eggplant Anthocyanins. Food Sci. Technol. Int Tokyo 1998, 4(1), 25-28.

(Continued)

*Primary Examiner* — Dale R Miller
(74) *Attorney, Agent, or Firm* — Meunier Carlin & Curfman LLC

(57) ABSTRACT

Disclosed herein are photoisomerized compositions comprising anthocyanins and methods of making an use thereof. For example, disclosed herein are methods of photoisomerizing a composition, the methods comprising: irradiating a composition comprising an anthocyanin dissolved in a solvent solution with UV light; wherein at least a portion of the anthocyanin is present as a trans isomer before the irradiation; wherein the solvent solution comprises ethanol and water in a ratio of ethanol to water (volume/volume) of 99:1 to 70:30; thereby converting at least a portion of trans isomer to a cis isomer via photoisomerization to produce a photoisomerized composition. In some examples, the photoisomerized composition has a more intense and stable blue color at pH 8 relative to the composition before irradiation.

20 Claims, 24 Drawing Sheets
(5 of 24 Drawing Sheet(s) Filed in Color)

(56)                    References Cited

OTHER PUBLICATIONS

He F et al. Anthocyanins and Their Variations in Red Wines I. Monomeric Anthocyanins and Their Color Expression. Molecules, 2017, 17, 1751-1601.

Ichiyanagi T et al. Nasunin from Eggplant Consists of Cis-Trans Isomers of Delphinidin 3-[4-(p-Coumaroyl)-L-rhamnosyl (1→6)glucopyranoside]]-5-glucopyranoside. J. Agric. Food Chem. 2005, 53, 9472-9477.

Khoo et al. Anthocyanidins and anthocyanins: colored pigments as food, pharmaceutical ingredients, and the potential health benefits. Food & Nutrition Research, 2017, 61, 1361779.

Lee et al. (2007). Anthocyanins and other polyphenolics in American elderberry (Sambucus canadensis) and European elderberry (S. nigra) cultivars. Journal of the Science of Food and Agriculture, 87(Aug. 2007), 2665-2675. https://doi.org/10.1002/jsfa.

Lewis et al. (1989). The singlet states of methyl cinnamate and methyl indenoate. Journal of Photochemistry and Photobiology, A: Chemistry, 47(2), 173-179. https://doi.org/10.1016/1010-6030(89)87063-7.

Lila. Anthocyanins and Human Health: An In Vitro Investigative Approach. Journal of Biomedicine and Biotechnology, 2004, 2004:5, 306-313.

Malien-Aubert C et al. Color Stability of Commercial Anthocyanin-Based Extracts in Relation to the Phenolic Composition. Protective Effects by Intra- and Intermolecular Copigmentation. J. Agric. Food Chem. 2001, 49(1), 170-176.

Martín et al. (2017). Anthocyanin Pigments: Importance, Sample Preparation and Extraction. In Phenolic Compounds—Natural Sources, Importance and Applications. InTech. https://doi.org/10.5772/66892.

Mazza G et al. The Mechanism of Co-Pigmentation of Anthocyanins in Aqueous Solutions. Phytochem. 1990, 29(4), 1097-1102.

Quant et al. (2019). Solvent Effects on the Absorption Profile, Kinetic Stability, and Photoisomerization Process of the Norbornadiene-Quadricyclanes System. Journal of Physical Chemistry C, 123(12), 7081-7087. https://doi.org/10.1021/acs.jpcc.9b02111.

Rodríguez et al. (2020). Understanding the role played by protic ionic liquids (PILs) and the substituent effect for enhancing the generation of Z-cinnamic acid derivatives. Cite This: Photochem. Photobiol. Sci, 19, 819. https://doi.org/10.1039/d0pp00072h.

Sadilova E et al. Anthocyanins, Colour and Antioxidant Properties of Eggplant (Solanum melongena L.) and Violet Pepper (Capsicum annuum L.) Peel Extracts. Z Naturforsch C J Biosci. 2006, 61(7-8), 527-35.

Salum et al. (2010). Photoisomerization of ionic liquid ammonium cinnamates: One-pot synthesis-isolation of Z-cinnamic acids. Organic Letters, 12(21), 4808-4811. https://doi.org/10.1021/ol1019508.

Salum et al. (2013). High purity cis-cinnamic acid preparation for studying physiological role of trans-cinnamic and cis-cinnamic acids in higher plants. Environmental Control in Biology, 51(1), 1-10. https://doi.org/10.2525/ecb.51.1.

Sigurdson et al. (2018). Impact of location, type, and number of glycosidic substitutions on the color expression of o-dihydroxylated anthocyanidins. Food Chemistry, 268(February), 416-423. https://doi.org/10.1016/j.foodchem.2018.06.079.

Sigurdson GT et al. Bathochromic and Hyperchromic Effects of Aluminum Salt Complexation by Anthocyanins from Edible Sources for Blue Color Development. J. Agric. Food Chem. 2014, 62(29), 6955-6965.

Sigurdson GT et al. Cis-Trans Configuration of Coumaric Acid Acylation Affects the Spectral and Colorimetric Properties of Anthocyanins. Molecules 2018, 23(3), 598.

Sigurdson GT et al. Molar Absorptivities ($\varepsilon$) and Spectral and Colorimetric Characteristics of Purple Sweet Potato Anthocyanins. Food Chem. 2019, 271, 497-504.

Sigurdson GT et al. Natural Colorants: Food Colorants from Natural Sources. Annu. Rev. Food Sci. Technol. 2017, 8(1), 261-280.

Sun et al. (2002). Effect of Food Processing on Bioactive Compounds in Foods: A New Method for Separation and Identification of cis-Cinnamic Acid from Its Racemic Mixture. ACS Symposium Series, 816, 228-240. https://doi.org/10.1021/bk-2002-0816.ch017.

Tang et al. (2018). Black goji as a potential source of natural color in a wide pH range. Food Chemistry, 269(February), 419-426. https://doi.org/10.1016/j.foodchem.2018.07.034.

Turner LB et al. Light Induced Isomerization and Dimerization of Cinnamic Acid Derivatives in Cell Walls. Phytochem. 1993. 33(4), 791-796.

Yin et al. (2003). Biologically active cis-cinnamic acid occurs naturally in Brassica parachinensis. Chinese Science Bulletin, 48(6), 555-558. https://doi.org/10.1360/03tb9118.

Yoshida K et al. Influence of E,Z-Isomerization and Stability of Acylated Anthocyanins under the UV Irradiation. In Biochem. Eng. J. 2003, 14, 163-169.

Yoshida K et al. Structure of Anthocyanins Isolated from Purple Leaves of Perilla ocimoides L. Var. Crispa Benth and Their Isomerization by Irradiation of Light. Agric. Biol. Chem. 1990, 54(7), 1745-1751.

Zhao et al. (2014). Structure-activity relationships of anthocyanidin glycosylation. Molecular Diversity, 18(3), 687-700. https://doi.org/10.1007/s11030-014-9520-z.

Zhao et al. (2017). Stability-increasing effects of anthocyanin glycosyl acylation. Food Chemistry, 214, 119-128. https://doi.org/10.1016/j.foodchem.2016.07.073.

Zhao et al. (2019). Does the wavelength dependent photoisomerization process of the p-coumaric acid come out from the electronic state dependent pathways? Spectrochimica Acta—Part A: Molecular and Biomolecular Spectroscopy, 211, 203-211. https://doi.org/10.1016/j.saa.2018.12.010.

Zheng J et al. Anthocyanins composition and antioxidant activity of wild Lycium ruthenicum Murr. from Qinghai-Tibet Plateau. Food Chem. 2010, 126(3), 859-865.

Zhou Y et al. Accumulation of Anthocyanins and Other Phytochemicals in American Elderberry Cultivars during Fruit Ripening and its Impact on Color Expression. Plants. 2020, 9, 1721.

* cited by examiner delphinidin-3-*trans*-*p*-coumaroyl-
rutinoside-5-glucoside
(*trans*-Dp)

delphinidin-3-*cis*-*p*-coumaroyl-
rutinoside-5-glucoside
(*cis*-Dp)

$hv$

UV Spectral Chart

365nm UV without Filter

GTI ColorMatcher D65 Lamp

PHOTOISOMERIZED COMPOSITIONS OF ANTHOCYANINS AND METHODS OF MAKING AND USE THEREOF

CROSS-REFERENCE TO RELATED APPLICATIONS

This application claims the benefit of priority to U.S. Provisional Application No. 63/219,054 filed Jul. 7, 2021, which is hereby incorporated herein by reference in its entirety.

BACKGROUND

Color is often used by the consumer as an important indicator of food quality and it may remarkably affect consumer food preferences and acceptance. In recent years, the market for the application of synthetic colorants has decreased in favor of natural colorants, especially since the human safety of synthetic food dyes has been questioned, and their use, legally challenged. For this reason, the food industry is making efforts to replace the synthetic food colorants with naturally-derived colorants.

Anthocyanins are one of the major plant-derived pigments that can be found in many fruits, vegetables, grains and flowers, responsible for their red, purple and blue. Anthocyanin-based colorants have become more popular due to their wide color hues, water-soluble characteristics, and potential health benefits. Despite this, anthocyanin-based colorants carry much more limitations for food applications than synthetic colorants.

Although cis acylations may be better resistance to bleaching and anthocyanin extracts with the presence of cis isomers could be better candidates as natural colorants, the scarcity of cis isomers in nature limits their industrial application. Efficient methods of producing compositions with high proportions of cis isomers of anthocyanins are thus needed. The compositions, methods, and systems discussed herein addresses these and other needs.

SUMMARY

In accordance with the purposes of the disclosed compositions, methods, and systems as embodied and broadly described herein, the disclosed subject matter relates photoisomerized compositions comprising anthocyanins and methods of making an use thereof.

For example, disclosed herein are methods of photoisomerizing a composition, the methods comprising: irradiating a composition comprising an anthocyanin dissolved in a solvent solution with UV light; wherein at least a portion of the anthocyanin is present as a trans isomer before the irradiation; wherein the solvent solution comprises ethanol and water in a ratio of ethanol to water (volume/volume) of 99:1 to 70:30; thereby converting at least a portion of trans isomer to a cis isomer via photoisomerization to produce a photoisomerized composition.

In some examples, the solvent solution comprises ethanol and water in a ratio of ethanol to water of 99:1 or less, 97:3 or less, 94:6 or less, 90:10 or less, 88:12 or less, 86:14 or less, 84:16 or less, 82:18 or less, or 80:20 or less. In some examples, the solvent solution comprises ethanol and water in a ratio of ethanol to water of from 90:10 to 80:20. In some examples, the solvent solution comprises ethanol and water in a ratio of ethanol to water of 90:10.

In some examples, the UV light comprises light of one or more wavelengths of from 100 nm to 400 nm. In some examples, the UV light comprises light of one or more wavelengths of from 200 nm to 300 nm. In some examples, the UV light comprises UVC light. In some examples, the UV light comprises light of one or more wavelengths of from 100 nm to 280 nm. In some examples, the UV light comprises light of one or more wavelengths of from 250 nm to 260 nm. In some examples, the UV light has a wavelength of 254 nm.

In some examples, the composition is irradiated for an amount of time of from 1 minute to 60 minutes. In some examples, the composition is irradiated for an amount of time of from 1 minute to 20 minutes. In some examples, the composition is irradiated for an amount of time of from 4 minutes to 16 minutes, from 1 minute to 12 minutes, from 12 minutes to 20 minutes, or from 12 minutes to 16 minutes.

In some examples, the composition comprises a crude extract derived from a plant dissolved in the solvent solution. In some examples, the composition comprises a crude extract derived from a raw agricultural product dissolved in the solvent solution. In some examples, the composition comprises a crude extract derived from an elderberry dissolved in the solvent solution.

In some examples, the anthocyanin is derived from a plant. In some examples, the anthocyanin is derived from a raw agricultural product. In some examples, the anthocyanin is derived from an elderberry. In some examples, the anthocyanin comprises an acylated anthocyanin. In some examples, the anthocyanin comprises a cinnamic acid acylated anthocyanin. In some examples, the anthocyanin comprises cyanidin-3-p-coumaroyl-sambubioside-5-glucoside.

In some examples, the composition comprises the anthocyanin in a concentration of from 50 to 500 micromoles per liter (micromolar, $\mu M$). In some examples, the composition comprises the anthocyanin in a concentration of from 100 to 300 $\mu M$. In some examples, the composition comprises the anthocyanin in a concentration of from 100 to 200 $\mu M$.

In some examples, the composition comprises the anthocyanin in a concentration of from 100 to 200 $\mu M$ and the solvent solution comprises ethanol and water in a ratio of ethanol to water of 90:10 to 80:20.

In some examples, the cis isomer to the trans isomer are present in the photoisomerized composition in a ratio of 0.2 or more, 0.5 or more, 0.65 or more, or 0.75 or more. In some examples, the cis isomer is present in the photoisomerized composition in a concentration of 20 $\mu M$ or more, 40 $\mu M$ or more, 50 $\mu M$ or more, or 60 $\mu M$ or more.

In some examples, the photoisomerized composition has improved color and stability relative to the composition before irradiation. In some examples, the photoisomerized composition has a more intense and stable blue color at pH 8 relative to the composition before irradiation.

In some examples, the method further comprises making the composition by dissolving the anthocyanin in the solvent solution. In some examples, the method further comprises extracting the anthocyanin from a source. In some examples, the source is a plant. In some examples, the source is a raw agricultural product.

Also disclosed herein are photoisomerized composition made using any of the methods disclosed herein.

Also disclosed herein are methods of use of the photoisomerized compositions disclosed herein, for example as a natural food dye, on an OTC coating, or in a cosmetic.

Also disclosed herein are methods of photoisomerizing a composition, the methods comprising: irradiating a composition comprising an anthocyanin dissolved in a solvent solution with visible light; thereby converting at least a portion of the composition from a first isomer to a second isomer (e.g., from a trans isomer to a cis isomer, or vice versa) via photoisomerization to produce a photoisomerized composition.

Additional advantages of the disclosed compositions, systems, and methods will be set forth in part in the description which follows, and in part will be obvious from the description. The advantages of the disclosed compositions, systems, and methods will be realized and attained by means of the elements and combinations particularly pointed out in the appended claims. It is to be understood that both the foregoing general description and the following detailed description are exemplary and explanatory only and are not restrictive of the disclosed systems and methods, as claimed.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

The patent or application file contains at least one drawing executed in color. Copies of this patent or patent application publication with color drawing(s) will be provided by the Office upon request and payment of the necessary fee.

The accompanying figures, which are incorporated in and constitute a part of this specification, illustrate several aspects of the disclosure, and together with the description, serve to explain the principles of the disclosure.

DETAILED DESCRIPTION

Figure 1A:
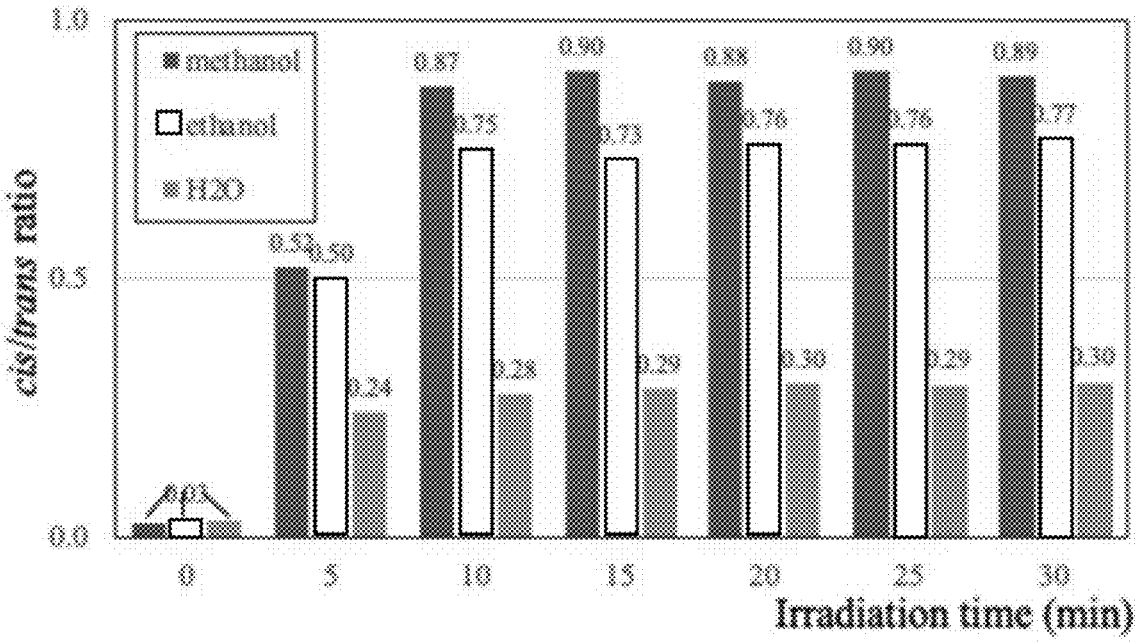
FIG. 1A. The cis/trans ratio of 100 μM American elderberry crude extract during 30 min UV irradiation (254 nm) in 100% HCl-methanol, ethanol and water.

The compositions, methods, and systems described herein may be understood more readily by reference to the following detailed description of specific aspects of the disclosed subject matter and the Examples included therein.

Before the present compositions, methods, and systems are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

Disclosed herein are methods of photoisomerizing a composition, the methods comprising: irradiating a composition comprising an anthocyanin dissolved in a solvent solution with UV light; wherein at least a portion of the anthocyanin is present as a trans isomer before the irradiation; wherein the solvent solution comprises ethanol and water in a ratio of ethanol to water (volume/volume) of 99:1 to 70:30; thereby converting at least a portion of trans isomer to a cis isomer via photoisomerization to produce a photoisomerized composition.

Also disclosed herein are methods of photoisomerizing a composition, the methods comprising: irradiating a composition comprising an anthocyanin dissolved in a solvent solution with visible light; thereby converting at least a portion of the composition from a first isomer to a second isomer (e.g., from a trans isomer to a cis isomer, or vice versa) via photoisomerization to produce a photoisomerized composition.

In some examples, the solvent solution comprises ethanol and water in a ratio of ethanol to water (volume/volume) of 99:1 or less (e.g., 98:2 or less, 97:3 or less, 96:4 or less, 95:5 or less, 94:6 or less, 93:7 or less, 92:8 or less, 91:9 or less, 90:10 or less, 89:11 or less, 88:12 or less, 87:13 or less, 86:14 or less, 85:15 or less, 84:16 or less, 83:17 or less, 82:18 or less, 81:19 or less, 80:20 or less, 79:21 or less, 78:22 or less, 77:23 or less, 76:24 or less, 75:25 or less, 74:26 or less, 73:27 or less, 72:28 or less, or 71:29 or less).

In some examples, the solvent solution comprises ethanol and water in a ratio of ethanol to water (volume/volume) of 70:30 or more (e.g., 71:29 or more, 72:28 or more, 73:27 or more, 74:26 or more, 75:25 or more, 76:24 or more, 77:23 or more, 78:22 or more, 79:21 or more, 80:20 or more, 81:19 or more, 82:18 or more, 83:17 or more, 84:16 or more, 85:15 or more, 86:14 or more, 87:13 or more, 88:12 or more, 89:11 or more, 90:10 or more, 91:9 or more, 92:8 or more, 93:7 or more, 94:6 or more, 95:4 or more, 96:4 or more, 97:3 or more, or 98:2 or more). The ratio of ethanol to water in the solvent solution can range from any of the minimum values described above to any of the maximum values described above. For example, the solvent solution can comprise ethanol and water in a ratio of ethanol to water (volume/volume) of 99:1 to 70:30 (e.g., from 99:1 to 85:15, from 85:15 to 70:30, from 99:1 to 90:10, from 90:10 to 80:20, from 80:20 to 90:30, from 99:1 to 75:25, from 95:5 to 70:30, or from 95:5 to 75:25). In some examples, the solvent solution comprises ethanol and water in a ratio of ethanol to water of from 90:10 to 80:20. In some examples, the solvent solution comprises ethanol and water in a ratio of ethanol to water of 90:10.

The UV light can comprise light of one or more wavelengths of 100 nm or more (e.g., 125 nm or more, 150 nm or more, 175 nm or more, 200 nm or more, 225 nm or more, 250 nm or more, 275 nm or more, 300 nm or more, 325 nm or more, 350 nm or more, or 375 nm or more). In some examples, the UV light can comprise light of one or more wavelengths of 400 nm or less (e.g., 375 nm or less, 350 nm or less, 325 nm or less, 300 nm or less, 275 nm or less, 250 nm or less, 225 200 nm or less, 175 nm or less, 150 nm or less, or 125 nm or less). The UV light can comprise light of one of more wavelengths that ranges from any of the minimum values described above to any of the maximum values described above. For example, the UV light can comprise light of one of more wavelengths of from 100 nm to 400 nm (e.g., from 100 nm to 250 nm, from 250 nm to 400 nm, from 100 nm to 200 nm, from 200 nm to 300 nm, from 300 nm to 400 nm, from 125 nm to 400 nm, from 100 nm to 375 nm, or from 125 nm to 375 nm). In some examples, the UV light comprises light of one or more wavelengths of from 200 nm to 300 nm. In some examples, the UV light comprises UVC light. In some examples, the UV light comprises light of one or more wavelengths of from 100 nm to 280 nm. In some examples, the UV light comprises light of one or more wavelengths of from 250 nm to 260 nm. In some examples, the UV light has a wavelength of 254 nm. In some examples, the UV light comprises UVA light. In some examples, the UV light comprises light of one or more wavelengths of from 315 nm to 400 nm. In some examples, the UV light comprises light of one or more wavelengths from 300 nm to 400 nm. In some examples, the UV light comprises light of one or more wavelengths from 300 nm to 400 nm, such as 365 nm and/or 440 nm.

The visible light can, for example, comprise light of one or more wavelengths of 350 nm or more (e.g., 375 nm or more, 400 nm or more, 425 nm or more, 450 nm or more, 475 nm or more, 500 nm or more, 525 nm or more, 550 nm or more, 575 nm or more, 600 nm or more, 625 nm or more, 650 nm or more, or 675 nm or more). In some examples, the visible light can comprise light of one or more wavelengths of 700 nm or less (e.g., 675 nm or less, 650 nm or less, 625 nm or less, 600 nm or less, 575 nm or less, 550 nm or less, 525 nm or less, 500 nm or less, 475 nm or less, 450 nm or less, 425 nm or less, 400 nm or less, or 375 nm or less). The visible light can comprise light of one or more wavelengths that ranges from any of the minimum values described above to any of the maximum values described above. For example, the visible light can comprise light of one or more wavelengths of from 350 nm to 700 nm (e.g., from 350 nm to 525 nm, from 525 nm to 700 nm, from 350 nm to 400 nm, from 400 nm to 450 nm, from 450 nm to 500 nm, from 500 nm to 550 nm, from 550 nm to 600 nm, from 600 nm to 650 nm, from 650 nm to 700 nm, from 400 nm to 700 nm, from 350 nm to 650 nm, from 400 nm to 650 nm, from 350 nm to 410 nm, from 450 nm to 550 nm, from 550 nm to 700 nm, from 400 nm to 435 nm, from 435 nm to 560 nm, from 560 nm to 590 nm, or from 600 nm to 700 nm). In some examples, the visible light is provided by a light source, such as a D65 or artificial sunlight source or a fluorescent light.

In some examples, the composition is irradiated for an amount of time of 1 minute or more (e.g., 2 minutes or more, 3 minutes or more, 4 minutes or more, 5 minutes or more, 10 minutes or more, 15 minutes or more, 20 minutes or more, 25 minutes or more, 30 minutes or more, 35 minutes or more, 40 minutes or more, 45 minutes or more, 50 minutes or more, or 55 minutes or more). In some examples, the composition is irradiated for an amount of time of 60 minutes or less (e.g., 55 minutes or less, 50 minutes or less, 45 minutes or less, 40 minutes or less, 35 minutes or less, 30 minutes or less, 25 minutes or less, 20 minutes or less, 15 minutes or less, 10 minutes or less, 5 minutes or less, 4 minutes or less, 3 minutes or less, or 2 minutes or less). The amount of time that the composition is irradiated can range from any of the minimum values described above to any of the maximum values described above. For example, the composition can be irradiated for an amount of time of from 1 minute to 60 minutes (e.g., from 1 minute to 30 minutes, from 30 minutes to 60 minutes, from 1 minute to 20 minutes, from 20 minutes to 40 minutes, from 40 minutes to 60 minutes, from 2 minutes to 60 minutes, from 1 minute to 55 minutes, from 2 minutes to 55 minutes, from 4 minutes to 16 minutes, from 1 minute to 12 minutes, from 12 minutes to 20 minutes, or from 12 minutes to 16 minutes).

In some examples, the composition comprises a crude extract derived from a plant dissolved in the solvent solution. The crude extract can, for example, be derived from a whole plant or any portion thereof, such as a flower (e.g., flower petals), leaf, stem, etc. In some examples, the composition comprises a crude extract derived from a raw agricultural product dissolved in the solvent solution. Examples of raw agricultural products include vegetables, fruits, grains, nuts, and mixtures thereof. In some examples, the raw agricultural product includes a fruit, a vegetable, or a combination thereof. In some examples, the composition comprises a crude extract derived from a berry such as a bilberry, blueberry, blackberry, blackcurrant, chokeberry, strawberry, elderberry, or a combination thereof. In some examples, the composition comprises a crude extract derived from a red radish (*Raphanus sativus*), black carrot (*Daucus carota* L.), red cabbage, black currant, blueberry, red grape, blackberry, black goji (*Lycium ruthenicum*), eggplant (*Solanum melongena*), East Asian eggplant, tomato (*Solanaceae lycopersicum*) (cv. Indigo Rose), violet pepper (*Capsicum annuum*), elderberry, or a combination thereof. In some examples, the composition comprises a crude extract derived from an elderberry, such as an American elderberry, dissolved in the solvent solution. In some examples, the composition comprises a crude extract derived from an eggplant, such as an East Asian eggplant, dissolved in the solvent solution.

In some examples, the anthocyanin is derived from a plant dissolved in the solvent solution. The crude extract can, for example, be derived from a whole plant or any portion thereof, such as a flower (e.g., flower petals), leaf, stem, etc. In some examples, the anthocyanin comprises a crude extract derived from a raw agricultural product. Examples of raw agricultural products include vegetables, fruits, grains, nuts, and mixtures thereof. In some examples, the raw agricultural product includes a fruit, a vegetable, or a combination thereof. In some examples, the anthocyanin is derived from a berry such as a bilberry, blueberry, blackberry, blackcurrant, chokeberry, strawberry, elderberry, or a combination thereof. In some examples, the anthocyanin is derived from a red radish (*Raphanus sativus*), black carrot (*Daucus carota* L.), red cabbage, black currant, blueberry, red grape, blackberry, elderberry, or a combination thereof. In some examples, the anthocyanin is derived from an elderberry, such as an American elderberry, dissolved in the solvent solution.

In some examples, the anthocyanin comprises an acylated anthocyanin. In some examples, the anthocyanin comprises a cinnamic acid acylated anthocyanin. In some examples, the anthocyanin comprises cyanidin-3-p-coumaroyl-sambubioside-5-glucoside, delphinidin-3-p-coumaroyl-rutinoside-5-glucoside, or a combination thereof.

In some examples, the composition comprises the anthocyanin in a concentration of 50 micromoles per liter (micromolar, µM) or more (e.g., 75 µM or more, 100 µM or more, 125 µM or more, 150 µM or more, 175 µM or more, 200 µM or more, 225 µM or more, 250 µM or more, 275 µM or more, 300 µM or more, 325 µM or more, 350 µM or more, 375 µM or more, 400 µM or more, 425 µM or more, 450 µM or more, or 475 µM or more). In some examples, the composition comprises the anthocyanin in a concentration of 500 µM or less (e.g., 475 µM or less, 450 µM or less, 425 µM or less, 400 µM or less, 375 µM or less, 350 µM or less, 325 µM or less, 300 µM or less, 275 µM or less, 250 µM or less, 225 µM or less, 200 µM or less, 175 µM or less, 150 µM or less, 125 µM or less, 100 µM or less, or 75 µM or less). The concentration of the anthocyanin in the composition can range from any of the minimum values described above to any of the maximum values described above. For example, the composition can comprise the anthocyanin in a concentration of from 50 to 500 micromoles per liter (micromolar, µM) (e.g., from 50 µM to 275 µM, from 275 µM to 500 µM, from 50 µM to 150 µM, from 150 µM to 250 µM, from 250 µM to 350 µM, from 350 µM to 500 µM, from 75 µM to 500 µM, from 50 µM to 475 µM, from 75 µM to 475 µM, from 100 to 300 µM, or 100 to 200 µM). In some examples, the composition comprises the anthocyanin in a concentration of from 100 to 200 µM and the solvent solution comprises ethanol and water in a ratio of ethanol to water of 90:10 to 80:20.

In some examples, the cis isomer to the trans isomer are present in the photoisomerized composition in a ratio of 0.2 or more (e.g., 0.25 or more, 0.3 or more, 0.35 or more, 0.4 or more, 0.45 or more, 0.5 or more, 0.55 or more, 0.6 or more, 0.65 or more, 0.7 or more, 0.75 or more, 0.8 or more, 0.85 or more, 0.9 or more, 0.95 or more, 1 or more, 1.05 or more, 1.1 or more, or 1.15 or more). In some examples, the cis isomer to the trans isomer are present in the photoisomerized composition in a ratio of 1.2 or less (e.g., 1.15 or less, 1.1 or less, 1.05 or less, 1 or less, 0.95 or less, 0.9 or less, 0.85 or less, 0.8 or less, 0.75 or less, 0.7 or less, 0.65 or less, 0.6 or less, 0.55 or less, 0.5 or less, 0.45 or less, 0.4 or less, 0.35 or less, 0.3 or less, or 0.25 or less). The ratio of the cis isomer to the trans isomer in the photoisomerized composition can range from any of the minimum values described above to any of the maximum values described above. For example, the cis isomer to the trans isomer can be present in the photoisomerized composition in a ratio of from 0.2 to 1.2 (e.g., from 0.2 to 0.7, from 0.7 to 1.2, from 0.2 to 0.4, from 0.4 to 0.6, from 0.6 to 0.8, from 0.8 to 1, from 1 to 1.2, from 0.3 to 1.2, from 0.5 to 1.2, from 0.65 to 1.2, or from 0.75 to 1.2).

In some examples, the cis isomer is present in the photoisomerized composition in a concentration of 20 µM or more (e.g., 25 µM or more, 30 µM or more, 35 µM or more, 40 µM or more, 45 µM or more, 50 µM or more, 55 µM or more, 60 µM or more, 65 µM or more, 70 µM or more, 75 µM or more, 80 µM or more, 85 µM or more, 90 µM or more, 95 µM or more, or 100 µM or more).

In some examples, the method further comprises making the composition by dissolving the anthocyanin in the solvent solution.

In some examples, the method further comprises extracting the anthocyanin from a source, such as a raw agricultural product.

Also disclosed herein are photoisomerized compositions made using any of the methods disclosed herein. In some examples, the photoisomerized composition has improved color and stability relative to the composition before irradiation. In some examples, the photoisomerized composition has a more intense and stable blue color at pH 8 relative to the composition before irradiation.

Also disclosed herein are methods of use of the photoisomerized compositions, for example as a natural food dye, on an OTC coating, in a cosmetic, etc.

A number of embodiments of the invention have been described. Nevertheless, it will be understood that various modifications may be made without departing from the spirit and scope of the invention. Accordingly, other embodiments are within the scope of the following claims.

The examples below are intended to further illustrate certain aspects of the systems and methods described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of measurement conditions, e.g., component concentrations, temperatures, pressures and other measurement ranges and conditions that can be used to optimize the described process.

Example 1—Evaluating Key Factors Affecting Anthocyanin Photoisomerization to Modulate Anthocyanin Color Expression and Stability Through UV Irradiation Abstract. UV irradiation of cinnamic acid acylated anthocyanin can convert trans isomers into more stable and less-bleached cis isomers. The effect of starting materials, solvents, and anthocyanin concentrations on anthocyanin photoisomerization were evaluated to determine a preferred conversion situation and modulate the color expression and stability of anthocyanin extract through photoisomerization. Cis and trans cyanidin-3-p-coumaroyl-sambubioside-5-glucosides and the anthocyanin crude extract were obtained from American elderberry. The extract and isolates were dissolved in ethanol-water solutions in a concentration of 100-300 µM. Samples were irradiated in a UV chamber (254 nm) for up to 20 min and the cis/trans ratio was monitored throughout the process by uHPLC-PDA. The spectra of the crude extract before and after 12 min UV irradiation in 90% ethanol were determined on a plate reader over 28-day storage, and color parameters were calculated from the spectra. Photoinduced isomerization from trans→cis and cis→trans occurred under UV irradiation. Photoisomerization of the crude extract resulted in longer equilibrium time with similar terminal cis/trans ratios (~0.65) as compared to the trans isolates. The crude extract reached a higher cis/trans ratio (~0.65) when being irradiated in ethanol than in water (~0.3) after equilibrium and obtained the highest cisltrans ratio in 90% ethanol (~0.75). Isomerization occurred more rapidly under lower anthocyanin concentration, and the final cis/trans ratio might vary depending on the concentration. Photoirradiation of American elderberry crude extract resulted in both hyperchromic and bathochromic shifts of visible spectra, producing more intense and saturated colors under a wide pH range. The overall color stability was also improved to a certain extent. Anthocyanin photoisomerization can be a food-friendly approach to enhance the color performance of anthocyanin-based natural colorants.

Introduction. Color is often used by the consumer as an important indicator of food quality and it may remarkably affect consumer food preferences and acceptance (Szalóki-Dorkó et al., 2015). In recent years, the market for the application of synthetic colorants has decreased in favor of natural colorants, especially since the human safety of synthetic food dyes has been questioned, and their use, legally challenged. For this reason, the food industry is making efforts to replace the synthetic food colorants with naturally-derived colorants. There have been a number of color additives derived from natural sources legally permitted as food colorants exempt from batch certification by the U.S. Food and Drug Administration (FDA) (FDA, 2016). Colorants exempt from certification include a variety of pigments derived from plant, animal, or mineral sources (Sigurdson et al., 2017).

Anthocyanins are one of the major plant-derived pigments that can be found in many fruits, vegetables, grains and flowers, responsible for their red, purple and blue colors (Martin et al., 2017; Sigurdson et al., 2017). Anthocyanin-based colorants have become more popular due to their wide color hues, water-soluble characteristics, and potential health benefits (Ahmadiani et al., 2014). Despite this, anthocyanin-based colorants carry much more limitations for food applications than synthetic colorants. The production of anthocyanin-based pigments usually requires large amount of raw materials therefore they are typically more expensive. Anthocyanins are in general sensitive to heat, light, and pH during processing and most anthocyanins can be bleached at pH around 4.5 and lose the tinctorial capacity. Besides, it is usually challenging to resemble the expected color hues (Sigurdson et al., 2017).

Berries such as bilberries, blueberries, blackberries, blackcurrants, chokeberries, and strawberries are rich sources of anthocyanins (Wallace & Giusti, 2015). However, most berries lack acylated anthocyanins, and consequently their anthocyanin extracts are less stable when compared to red radish (*Raphanus sativus*), black carrot (*Daucus carota* L.) and red cabbage (*Brassica oleracea*) (Giusti & Wrolstad, 2003). The latter are prized for their high acylated anthocyanin content. Anthocyanins with acylations, especially for those with aromatic acids, show generally better stability due to intramolecular and/or intermolecular co-pigmentation, and self-association reactions (Giusti & Wrolstad, 2003). Although anthocyanin itself is odorless and nearly flavorless, with a moderately astringent sensation (Martin et al., 2017), sources rich in acylated anthocyanins such as red radish and red cabbage carry out strong vegetative note due to their relatively high content of sulfur-containing compounds from glucosinolate degradation (Chen et al., 2017), therefore additional procedures are needed to remove or reduce the concentration of aroma and flavor compounds before food application, which increases the cost. Hence, an anthocyanin source that is low in price, rich in anthocyanin content, particularly the more stable acylated anthocyanins, and with less undesirable aroma and flavor is still being sought by the food industry.

The genus *Sambucus* L. (elderberry) belongs to the Adoxaceae family, and consists of 5-30 species and 6-11 subspecies depending on the taxonomy system (Mlynarczyk et al., 2020). Elderberry has been used as a medicinal plant for hundreds of years, and its cultivation has increased greatly over the last few decades as a result of increased attention to antioxidant-rich fruits and vegetables (Csorba et al., 2020). Anthocyanin content of elderberry fruits has been reported to be nearly 1400 mg/100 g FW, being significantly higher than black currant, blueberry, red grape, blackberry and most other fruit species (He et al., 2010; Prior et al., 1998; Purgar et al., 2012; Wu et al., 2004; Zhou et al., 2016). Their dark red concentrated juice can also be used as coloring agents for a series of food products.

The two most economically important species around the world are the European elderberry (*S. nigra* L.) and the American elderberry (*S. canadensis* L.) (Charlebois et al., 2010). The European elderberry is widely distributed in Europe, and has been introduced in various parts of the world, such as North America, East Asia, New Zealand, and South Australia (Charlebois et al., 2010). The American elderberry is native to most of eastern and midwestern North America (Byers et al., 2012). Since the European elderberry has a longer history of been grown as a commercial fruit crop than the American counterpart, more breeding selection, phytochemical and medicinal research has been conducted on the this species (Byers et al., 2012). Although both species can be grown commercially in North America, the native American species can better adapt to local conditions and therefore are more welcomed in the United States (Wilson et al., 2016). Other *Sambucus* species include *S. peruviana*, *S. racemose*, *S. cerulea* and some others, mainly distributed in South America, Europe and Asia (Schmid & Bolli, 1994). Since these species have not yet to be commercially grown in large scale, little research has been conducted on their phytochemical and medicinal properties.

Cultivation and domestication of American elderberry started in the 1920s (Byers et al., 2012). Single cultivar plantation leads to a short harvesting and processing season therefore can eliminate the problems caused by the uneven ripening and disease susceptibility (Csorba et al., 2020). Increased interest now appears on the breeding of cultivars specifically for the food industry and on the comparative evaluation of cultivars. The variations on chemical components, especially on anthocyanin traits, among different cultivars may considerably affect the elderberry extract coloring ability and their ultimate utilization in food industry. So far, some comparative studies have been conducted on the chemical traits of selected American cultivars (*S. canadensis*) (Lee & Finn, 2007; Ozgen et al., 2010; Perkins-Veazie et al., 2015) or European elderberry (*S. nigra*) (Ferreira et al., 2019), but they were seldom extended to the spectrophotometric and colorimetric properties, especially for American cultivars. The chemical composition including phenolics of the fruit is not only determined by genetic factors, but also greatly influenced by ripeness. Those internal and external factors team up and eventually affect the application of American elderberry as natural colorants.

All the major anthocyanins in *S. nigra, S. canadensis* and *S. peruviana* were identified as cyanidin-derivatives. More than 70% anthocyanins in American elderberry were determined to be acylated with p-coumaric acids (Zhou et al., 2020). p-Coumaric acid is a hydroxy derivative of cinnamic acid therefore contains a double bond on its side chain. Due to the presence of the double bond, anthocyanin acylated with p-coumaric acid can configure in either cis or trans (Zhao et al., 2017). Many studies have been conducted on the impact of site, type, number of glycosyl and acyl groups on the anthocyanin spectrophotometric and colorimetric properties (Sigurdson et al., 2018; Zhao et al., 2014, 2017), while the knowledge on the effects of cis-trans cinnamic acid configuration is still limited. Previous studies showed that the cis isomers exhibited molar absorptivity ($\varepsilon$) about 1.5 times larger than that of the trans and anthocyanins configured in cis were less likely to undergo hydration reaction at the mildly acidic pH (Ø. Andersen & Jordheim, 2005; George et al., 2001; Zhao et al., 2017). However, these studies were mostly conducted under a specific pH, and most comparisons were carried out on delphindin, malvidin, or petunidin derivatives, with little known on the cyanidin derivatives.

Although cis acylations may be better resistance to bleaching and anthocyanin extracts with the presence of cis isomers could be better candidates as natural colorants, the scarcity of cis isomers in nature limits their industrial application. Of botanical and edible fruits, only certain species or cultivars of black goji (*Lycium ruthenicum*) (Tang & Giusti, 2018), eggplant (*Solanum melongena*) (Ichiyanagi et al., 2005), elderberry (*Sambucus canadensis*) (Zhou et al., 2020), grape (*Vitis vinifera*) (Garcia-Beneytez et al., 2003), tomato (*Solanaceae lycopersicum*) (cv. Indigo Rose) (Wang et al., 2020) and violet pepper (*Capsicum annuum*) (Sadilova et al., 2006) have been identified to contain cis coumaric acylated anthocyanins, but all in small quantities (<10% of the total anthocyanin content).

A mutual cis-trans isomerization reaction of acylated anthocyanins was reported when exploring the acylated anthocyanin stability under artificial UV or sunlight irradiation (Yoshida et al., 1990, 2003). Irradiation of pure cis or trans cyanidin-derivatives in methanol solution by UV light at 366 nm ended up with a mix of cis and trans in approximately 1:1 ratio (Yoshida et al., 1990). According to the FDA, UV radiation consisting of low pressure mercury lamps emitting 90% of the emission at the wavelength of 253.7 nm is approved to be used for the processing and treatment of juice products to reduce the pathogens and other microorganisms (Food and Drug Administration (FDA), 2020). This provided a solution to multiply the amount of cis acylations in vitro. Nevertheless, there is a huge gap persisted between the in vitro UV triggered acylated anthocyanin photoisomerization and practical application, as isolated cis or trans anthocyanins cannot be regarded as naturally-derived pigments and methanolic solution is toxic.

Cinnamic acids are secondary metabolites produced by plants. Due to the presence of carbon-to-carbon double bonds molecular structure, they can exist in both cis and trans-forms (Salum & Erra-Balsells, 2013). Both forms have been found in nature. However, the trans-cinnamic acids are the predominant form (>99%), probably due to their better stability as compared to the corresponding cis-isomers or because of their biological roles (Salum & Erra-Balsells, 2013; Sun et al., 2002). Cinnamic acids include an array of compounds, such as coumaric acid, caffeic acid, and ferulic acid.

The trans-cinnamic acid is synthesized from catalyzing L-phenylalanine (L-Phe) by phenylalanine ammonia lyase (PAL) (Salum & Erra-Balsells, 2013). The naturally occurring cis cinnamic acid could be a product of sunlight-mediated photoisomerization of trans-cinnamic acid or a product of isomerase catalysis from trans isomers (Yin et al., 2003). The cis-configured cinnamic acid is believed to be extremely scarce in nature, therefore, little effort has been devoted to study the production and function of this group of compounds.

Cinnamic acids can conjugate with anthocyanins to form acylated anthocyanins. And p-coumaric acid is the most frequent aromatic acyl group of anthocyanins found in nature (Andersen & Markham, 2005). Similar to their free forms in nature, the cinnamic acid residues of acylated anthocyanins can be cis configured, but more prevalently, in the trans form. It has been found that cis isomers exhibit larger $\varepsilon$ and $\lambda_{max}$, increased color intensity, and reduced hydration across the pH (George et al., 2001; Sigurdson et al., 2018). Half-lives of cis isomers were also shown to be 2-6 times longer than trans at pH 1-8. These results suggest that cis isomers are expected to possess unique color characteristics and extended stability under a wide pH range.

Although the cis isomers show superiorities on coloring capacity, their scarcity limits the application potentials. A mutual conversion between the two geometric isomers has been demonstrated in vitro with artificial and natural irradiation (Yoshida et al., 1990, 2003), which provides possibilities to amplify the quantity of cis isomers in vitro. The photoirradiated cis-trans isomerization is reversible thus leads to a photostationary-state mixture of both isomers in solution (Salum et al., 2010). The excitation of trans isomers with UV light led to cis to trans isomerization with approximately 1:1 ratio in methanol solution and 1:6 in aqueous solution (Yoshida et al., 2003). Although the photoisomerization efficiency of cinnamic esters has been reported to be independent of the solvent (Lewis et al., 1989; Rodriguez et al., 2020), the nature of solvent seems to greatly impact the anthocyanin trans-cis photoisomerization pathways.

Photochemical cis-trans isomerization of cinnamic acid has become a major area of interest in modern photochemical research, their applications have been expanded to storage devices and optomechanical switching (Salum et al., 2010). Current knowledge on the photoisomerization of anthocyanins is still limited. Relevant studies were conducted on the isolated cyanidin or delphinidin-derivatives with UV lamp at 365 nm, fluorescent light or sunlight (Hayashi et al., 1997; Ichiyanagi et al., 2005; Yoshida et al., 1990, 2003). Irradiation of juice products by UV lamp at 254 nm is approved for sterilization purpose by the FDA (Food and Drug Administration (FDA), 2019), making it a desirable wavelength for cis/trans conversion. Isomerization efficiency has been compared between methanolic and aqueous solutions, and among buffers at pH 3.2, 5.7, and 8.0. The methanolic solution was generally more efficient than the aqueous, and no isomerization was observed in pH 8.0 buffer (Hayashi et al., 1997; Yoshida et al., 2003). However, methanol is toxic due to its metabolic products (Centers for Disease Control and Prevention, 2021). Therefore, it is meaningful to evaluate the isomerization efficiency in a more food-friendly media such as ethanol. Besides, most studies only focused on the condition at a specific time point or after equilibrium (Hayashi et al., 1997; Ichiyanagi et al., 2005). As the composition of cis/trans mixture is governed by different factors and time dependency, it is necessary to delineate the overall perspective of the cis-trans isomerization.

A previous study revealed that American elderberry was rich in trans-p-coumaroyl-cyanidin derivatives, accompanied with a small quantity of cis isomers (Zhou et al., 2020). American elderberry was one of the few food materials containing cis-configured anthocyanins and was a part of fruit class. Therefore, its crude extract was used in order to predict the feasibility of triggering cis-trans photoisomerization in fruit juice. The first objective was to determine the impact of starting material (isolates versus anthocyanin crude extract), solvent, and anthocyanin concentration on the photoisomerization reactions. The second objective was to develop a method to increase the concentration of cis isomers in the anthocyanin extract in a food-friendly environment. A third objective was to modulate the color performance of American elderberry extract and expand its application as natural colorants through UV irradiation.

Materials and Methods

Anthocyanin extraction. Anthocyanins were extracted from the fully-ripened American elderberry fruits. Briefly, about 50 g American elderberry fruits were blended with liquid nitrogen for about 2 min until fine powder was achieved. Anthocyanins and other phenolics were extracted with acidified acetone and partitioned with chloroform (Rodriguez-Saona & Wrolstad, 2002). The powdered elderberries were then mixed with 2 volumes (~30 ml each) of 0.01% HCl acidified acetone and blended for another 1 min. The slurry was filtered using a Buchner funnel with Whatman No. 4 filter paper (Whatman Incorporation, NJ, US). After filtration, anthocyanins remaining in the slurry were re-extracted by 0.01% HCl acidified 70% (v/v) acetone until the slurry was almost colorless. The anthocyanin extract was mixed with chloroform and placed in a separatory funnel, the mixture was gently mixed and left to sit at room temperature for at least 2 hrs, until a good separation of aqueous anthocyanin extract and organic solvents (acetone and chloroform) was achieved. The anthocyanin-rich layer (top layer) was transferred to a flask and evaporated by a rotary evaporator (e.g., at 40° C.) to remove the acetone and chloroform residues. The anthocyanin crude extract was refrigerated until further analysis.

Anthocyanin isolation and purity check. The cis and trans cyanidin-3-p-coumaroyl-sambubioside-5-glucosides were isolated from the American elderberry crude extract by a Shimadzu semi-prep reverse-phase HPLC (Shimadzu, Columbia, MD, US) equipped with LC-6AD pumps, a SIL-20A HT autosampler, a SPD-M20A Photodiode Array Detector and a CBM-M20A communication module. A Luna reverse-phase PFP column (5 μm particle size and 100 Å pore size) with 250*21.2 nm column size (Phenomenex, Torrance, CA, US) was used to separate different compounds. The flow rate was 10 ml/min and the mobile phases consisted of 4.5% (v/v) formic acid acidified HPLC water (solvent A) and 100% acetonitrile (solvent B).

The American elderberry crude extract was filtered through a 0.2 μm RC membrane filter (Phenomenex, Torrance, CA, USA) before injection. The collected cis and trans isomers were diluted by one volume of 0.01% HCl acidified deionized distilled water and passed through a pre-activated C18 column to concentrate the isolates.

The purity of the isolated cis and trans isomers was determined by a Shimadzu ultra-High-Pressure Liquid Chromatography (uHPLC) equipped with LC-2040C pumps coupled to a triple-quadrupole Shimadzu LCMS-8040 mass spectrometer using LC-2040 PDA detector (Shimadzu, Columbia, MD, USA). A Restek reverse phase C-18 column (1.9 μm particle size and 100 Å pore size) with 50×2.1 mm column size (Restek Corporation, Bellefonte, PA, USA) was used to separate different compounds. Samples were filtered through a 0.2 μm RC membrane filter (Phenomenex, Torrance, CA, USA) before injection (10 ml). Samples were run using a flow rate of 0.25 ml/min and solvent A: 4.5% formic acid in HPLC water and solvent B: 100% acetonitrile, at 60° C. Anthocyanin separation was achieved using a linear gradient from 1% to 3% B in 2 min; 2 to 3 min, 3% to 4.5% B; 3 to 7.5 min, 4.5% to 8.5% B; 7.5 to 13 min, 8.5% to 40% B. Spectra (200-700 nm) was collected. The mass spectrometer was conducted under positive ion mode with Q1 and Q3 SIM scan. The mass spectrometer was set for positive ion mode, with total ion scan from 100-1000 m/z and precursor ion scan at 271, 287, 301, 303, 317 and 331 m/z. MS data, order of elution and comparison to literature were used for the anthocyanin identification.

Anthocyanin quantification. Anthocyanin concentration of the cis and trans cyanidin-3-p-coumaroyl-sambubioside-5-glucosides isolates and American elderberry crude extract were quantified by the pH-differential method (Giusti & Wrolstad, 2002). The absorbance of the anthocyanin extracts at pH 1 and pH 4.5 was measured using a SpectraMax 190 Microplate Reader (Molecular Devices, Sunnyvale, CA, USA) at 520 nm ($\lambda_{max}$) and 700 nm. with automated 1-cm pathlength correction. The molecular weight (449.2 g mol$^{-1}$) and molar extinction coefficient (26,900 L cm$^{-1}$ mol$^{-1}$) of cyanidin-3-glucoside (C3G) were used for calculation. The total monomeric anthocyanin content was expressed as mg C3GE per 100 g of FW.

Polymeric color was determined by measuring the absorbance of the extracts at 420 nm, 520 nm ($\lambda_{max}$) and 700 nm after being treated with sodium bisulfate (Giusti & Wrolstad, 2001). The percent polymeric color was expressed as the ratio between polymerized color and overall color density.

Total phenolic content was quantified using the Folin-Ciocalteau method and expressed as gallic acid equivalents (Waterhouse, 2002). Absorbance was read at 765 nm using the SpectraMax 190 Microplate Reader. Total phenolic content was calculated and expressed as mg gallic acid equivalents (GAE) per 100 g of FW Anthocyanin concentration in each isolates and extract was calculated using the formula:

$$\text{Anthocyanin content } (\mu mol/L) = [(A_{max} - A_{700})_{pH1.0} - (A_{max} - A_{700})_{pH4.5}] * DF * 10^6] / \varepsilon$$

Preliminary screening. A preliminary screening was conducted to help determine the solvent, anthocyanin concentration and observation time points to use for the photoisomerization reaction.

Initial screening: American elderberry crude extracts were dissolved in 0.01% HCl acidified methanol, ethanol, or water to a concentration of 100 μM and placed into quartz cuvettes (10 mm light path, 3.5 mL volume), capped with PTFE stoppers (Science Outlet Inc., Hong Kong, China). Irradiation took placed in a UV light chamber (UV Stratalinker Model 1800, Stratagene, San Diego, CA, US) with 5 254 nm UV light bulbs, 8 watts each (Stratagene, San Diego, CA, US). UV-light exposure times were 0, 5, 10, 15, 20, 25, and 30 min.

Impact of % water in ethanol: American elderberry crude extract was loaded on a pre-activated C18 cartridge, and vacuum filtered to completely remove water contained. Anthocyanins absorbed on the sorbent were eluted with 2 volumes of 0.01% HCl acidified ethanol. The anthocyanin concentration of the extract re-dissolved in ethanol was calculated using the concentration determined as described in "anthocyanin quantification." The ethanolic anthocyanin extract was diluted to 100 μM using the following ethanol-water ratios: 99:1 (v/v), 97:3 (v/v), 94:6 (v/v), 90:10 (v/v), 88:12 (v/v), 86:14 (v/v), 84:16 (v/v), 82:18 (v/v), 80:20 (v/v), 70:30 (v/v), 60:40 (v/v), 50:50 (v/v), 40:60 (v/v), 30:70 (v/v), 20:80 (v/v). Samples were irradiated 16 min in the UV chamber. Three replicates were prepared for each treatment.

Anthocyanin concentration: The crude extract was diluted to 100 or 500 μM by 0.01% HCl acidified ethanol. Exposure time for the samples were 0, 5, 10, 15, 20, 25, and 30 min.

UV irradiation of cis and trans isolates. The cis and trans isomers isolated in "Anthocyanin isolation and purity check" were diluted to 100 μM by 0.01% HCl acidified ethanol. Samples were pipetted into quartz cuvettes and irradiated in the UV chamber (254 nm). One sample of each isolate was removed from the UV chamber every 2 min until 20 min. Three replicates were prepared for each isolate at each time point.

UV irradiation of the crude extract. The crude extracts were diluted to 100 μM by 100%, 90%, or 80% ethanol (0.01% HCl acidified), 100% distilled water (0.01% HCl acidified) to determine the solvent effect. The crude extracts were diluted to 100, 200 or 300 μM by 80% ethanol (0.01% HCl acidified) to determine the concentration effect. The UV irradiation was conducted following the same method described in "UV irradiation of cis and trans isolates." Three replicates were prepared for each treatment at each time point.

Determination of conversion rate. After irradiation, each sample was diluted 8 times by 0.01% HCl acidified distilled water, filtered through a 0.2 μm RC membrane filter and capped within a HPLC vial. The cis/trans ratio was determined by the Shimadzu uHPLC-PDA equipped with LC-6AD pumps, a SIL-20A HT autosampler, a SPD-M20A Photodiode Array Detector and a CBM-M20A communication module. A Luna reverse-phase PFP column (5 μm particle size and 100 Å pore size) with 250*21.2 nm column size (Phenomenex, Torrance, CA, US) was used to separate different compounds. The flow rate was 10 ml/min and the mobile phases consisted of 4.5% (v/v) formic acid acidified HPLC water (solvent A) and 100% acetonitrile (solvent B).

The isolated cis and trans isomers were diluted by 1 volume of 0.01% HCl acidified deionized distilled water and passed through a pre-activated C18 column to remove acetonitrile. The cis and trans isolates were eluted with acidified (0.01% HCl) methanol, and re-dissolved in acidified deionized distilled water after evaporation The injection volume was 30 μL. The cis/trans ratio was calculated using the area under curve (AUC) of the corresponding peaks at max plot in the 521-525 nm range.

Conversion process modelling. The time-dependent isomerization process was programmed by Matlab 2020a (MathWorks, Natick, MA, USA). Model parameters were fitted by formulating into a nonlinear least square optimization problem, by searching for the parameter set that minimized the Root-mean-square error (RMSE) of model estimated values versus experiment measured values. Interior-point method was used to solve the nonlinear programming optimization problem (Potra & Wright, 2000).

The reaction starting from the cis isolates was modelled by a modified reciprocal squared function with formula:

$$Y(\text{cis/trans ratio}) = k * t^{(-2)} + R_t$$

where k is the curve rate, t is the time, and $R_t$ is the terminal cis/trans ratio.

The reaction starting from the trans isolates and the crude extracts were modelling using a modified sigmoid function with formula:

$$Y(\text{cis/trans ratio}) = (R_t - R_i)\left(\frac{2}{1 + e^{-kt}} - 1\right) + R_i$$

where k is the curve rate, t is the time, and $R_i$ and $R_t$ are the cis/trans ratios at initial and terminal states, respectively.

The time to equilibrium was determined when the slope of conversion curve was below 0.001 (threshold=0.001).

Buffer system and sample preparation. Buffer solutions of pH 1-9 were prepared. The buffer systems were composed of 0.025 M KCl for pH 1, 0.1 M citric acid and 0.2 M $Na_2HPO_4$ for pH 2-7, 0.2 M $Na_2HPO_4$ and 0.2 M $NaH_2PO_4$ for pH 8, and 0.1 M $Na_2CO_3$ and 0.1 M $NaHCO_3$ for pH 9 (Zhou et al., 2020).

The 100 μM American elderberry crude extract after 12 min UV irradiation in 0.01% HCl acidified 90% ethanol was poured into a beaker, wrapped with aluminum foil, and placed in the hood overnight to remove ethanol. The extracts with or without UV irradiation were re-dissolved in pH 1-9 buffer in a concentration of 100 μM. After mixing, a 300 μL aliquot of each sample was pipetted into a 96-well microplate. The microplate was sealed by a polyethylene sealing film, wrapped with parafilm and refrigerated.

Spectrophotometric and colorimetric data collection. Spectral data (380-700 nm, 1 nm interval) was collected after 1 hr equilibrium by the SpectraMax 190 Microplate Reader. The spectral change was monitored at day 1, 2, 3, 5, 7, 14, 21, and 28 to determine the extracts' color stability and half-lives at pH 1-9. The spectral data was converted into colorimetric data (L* (lightness), a*, b*, $C^*_{ab}$ (chroma), $h^*_{ab}$ (hue angle)) using the ColorBySpectra software according to CIE 1964 standard observer, D65 illuminant spectral distribution and 10° observer angle.

Statistical analysis. One-way ANOVA (two-tailed, a=0.05) and post hoc Tukey test were conducted by the SPSS software (IBM, Armonk, NY, US) to determine the most favorable ethanol-water mixture and compare the cis/trans ratio at 0, 4- and 16-min irradiation across different treatments. A t-test was conducted by the SPSS software to evaluate the impact of photoisomerization on anthocyanin spectrophotometric ($\lambda_{vis-max}$ (nm), absorbance at $\lambda_{vis-max}$ ($A_{vis-max}$) and % absorbance retention) and colorimetric (CIE L*, $C^*_{ab}$, $h^*_{ab}$) properties.

Results and Discussion

Preliminary screening of experimental conditions. To better select and scale the process variables, solvents, anthocyanin concentrations and observation time points were preliminarily screened.

Anthocyanin trans↔cis photoisomerization occurred in 0.01% HCl-methanol, ethanol and water, reaching a photostationary stage at around 15 minutes, and the terminal cis/trans ratios from the highest to the lowest were in the order of methanol>ethanol>water (FIG. 1A). Methanol has been the solvent of choice for most published studies on photoisomerization, yet, due to its toxicity, and the similar results obtained with ethanol, the experiments herein were continued using ethanol and water. In addition, the process was monitored at 2-min intervals for 20 minutes.

Figure 1B:
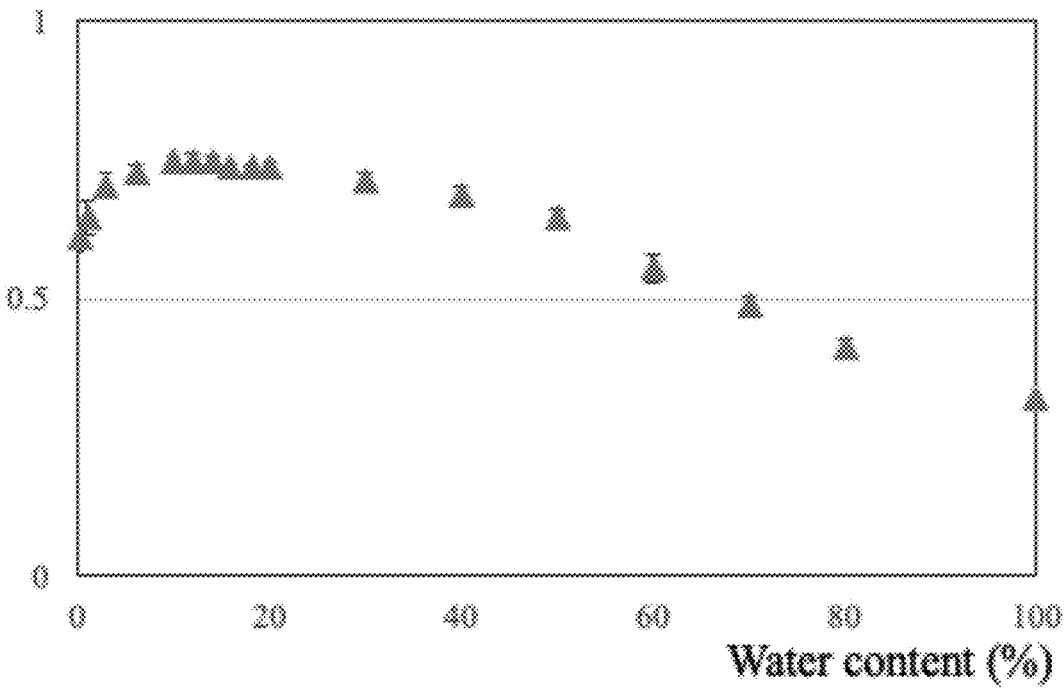
FIG. 1B. The cis/trans ratio after 16 min UV irradiation in 0.01% HCl acidified ethanol-water media (B), n=3, error bar indicate standard deviation.

For the initial experiment, anthocyanin crude extracts were dissolved in 0.01% HCl acidified distilled water, prior to dilution in ethanol. Replication of the experiment after complete removal of water resulted on lower trans to cis conversion, suggesting that the small amount of water favored the conversion ratio. Therefore, the photoisomerization reaction was evaluated in different ethanol/water mixtures (FIG. 1B). Higher conversion ratios were obtained when 10-20% water was mixed with ethanol (v/v). Therefore, 80%, 90% and 100% acidified ethanol as well as 100% acidified water were selected as solvents to be evaluated for anthocyanin photoisomerization.

Anthocyanin photoisomerization seemed to be more efficient under lower anthocyanin concentration (FIG. 2), producing more cis isomer, and at a faster rate than at the higher concentration. Therefore, 100, 200 and 300 μM were selected as the concentrations to be compared and discussed hereinafter.

Figure 3:
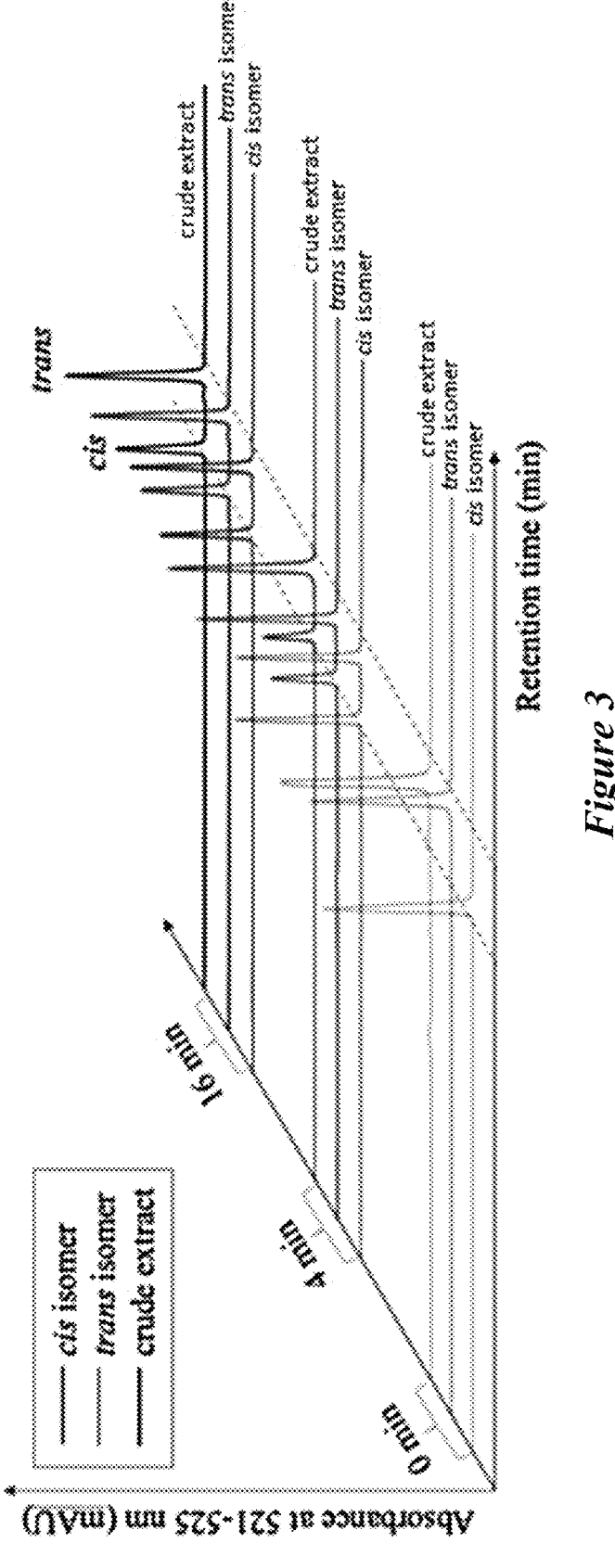
FIG. 3. HPLC chromatograms of 100 μM cyanidin-3-p-coumaroyl-sambubioside-5-glucoside (cis- or trans-) and American elderberry crude extract at the initial state (0 min), and after 4- or 16-min UV irradiation (254 nm) in 0.01% HCl-ethanol.

Photoisomerization of anthocyanin isolates versus crude extract. UV irradiation induced both cis→trans and trans→cis isomerization. Reaction of the cis isomers reached a cis/trans ratio of 1.003±0.007 after 4 min, and 0.706±0.005 after 16 min irradiation (FIG. 3 and Table 1). Reaction of the trans isomers reached a cis/trans ratio of 0.550±0.018 after 4 min, and 0.623±0.002 after 16 min irradiation. Thus, the trans↔cis conversions were mutually happened under UV irradiation, and the observed cis/trans ratio was actually the outcome of a two-way isomerization process.

Although cis isomers were scarce in nature, and cis→trans conversion might not be as extensively happened and studied as its reversed reaction, knowing that the two reactions simultaneously occur can help better govern the isomerization process on both directions.

TABLE 1

The cis/trans ratios of cyanidin-3-p-coumaroyl-sambubioside-5-glucoside (cis- or trans-) and American elderberry crude extract at the initial state (0 min), and after 4- or 16-min UV irradiation (254 nm). In parenthesis are standard deviations. Different superscript letters indicate significant differences (p < 0.05).

| | Initial cis/trans ratio | cis/trans at 4 min | cis/trans at 16 min |
|---|---|---|---|
| Comparison between anthocyanin isolates and crude extract(100% ethanol, 100 μM) | | | |
| Cis isomers | ND[1] | 1.003 (0.007)[c] | 0.706 (0.005)[b] |
| Trans isomers | 0.005 (0.001)[a] | 0.550 (0.018)[b] | 0.623 (0.002)[a] |
| Crude extract | 0.033 (0.001)[b] | 0.328 (0.001)[a] | 0.629 (0.009)[a] |
| Impact of solvents (100 μM crude extract) | | | |
| 100% $H_2O$ | 0.036 (0.002)[a] | 0.206 (0.004)[a] | 0.304 (0.001)[a] |
| 80% ethanol | 0.031 (0.001)[a] | 0.507 (0.025)[c] | 0.691 (0.004)[c] |
| 90% ethanol | 0.034 (0.001)[a] | 0.585 (0.025)[d] | 0.753 (0.004)[d] |
| 100% ethanol | 0.033 (0.003)[a] | 0.328 (0.001)[b] | 0.629 (0.009)[b] |
| Impact of anthocyanin concentration (μM) (crude extract in 80% ethanol) | | | |
| 100 | 0.031 (0.002)[a] | 0.507 (0.025)[a] | 0.691 (0.004)[a] |
| 200 | 0.034 (0.003)[a] | 0.368 (0.017)[b] | 0.668 (0.018)[a] |
| 300 | 0.035 (0.001)[a] | 0.233 (0.006)[c] | 0.510 (0.047)[b] |

[1]Not Determined

The two isomerization reactions were modelled using different functions (Table 2). The reaction starting from the cis isomer was modelled using a modified reciprocal squared function. The reactions starting from the trans and the crude extracts (will be introduced hereinafter) were modelled using modified sigmoid functions. A sigmoid function is commonly used on a progression with small beginnings, then accelerates and approaches a climax over time (Gibbs & MacKay, 2000). It has been widely used to simulate the learning curve and it provided a great prediction of anthocyanin photoisomerization behavior in the study. Model fitting of the two reactions are displayed in FIG. 4. The model parameters, terminal cis/trans ratio and time to equilibrium were summarized in Table 2.

TABLE 2

Model parameter (k, $R_i$, $R_t$), stable time (min), and coefficient of determination ($R^2$) of anthocyanin photoisomerization under different irradiation conditions.

| Anthocyanin source | Solvent | Concentration (μM) | Model | Initial cis/trans ratio ($R_i$) | Terminal cis/trans ratio ($R_t$) | Curve rate (k) | Time to equilibrium (min) | $R^2$ |
|---|---|---|---|---|---|---|---|---|
| Cis isomers | 100% ethanol | 100 | Modified reciprocal squared function* | NA*** | 0.682 | 5.42 | 22.1 | 0.999 |
| Trans isomers | 100% ethanol | 100 | Modified sigmoid function** | 0.000 | 0.630 | 0.63 | 10.5 | 0.995 |
| Crude extract | 100% ethanol | 100 | | 0.025 | 0.653 | 0.27 | 21.5 | 0.998 |
| Crude extract | 100% $H_2O$ | 100 | | 0.041 | 0.312 | 0.32 | 16.1 | 0.981 |
| Crude extract | 90% ethanol | 100 | | 0.041 | 0.746 | 0.54 | 12.2 | 0.997 |
| Crude extract | 80% ethanol | 100 | | 0.043 | 0.688 | 0.45 | 14.0 | 0.995 |

TABLE 2-continued

Model parameter (k, R$_i$, R$_t$), stable time (min), and coefficient of determination (R$^2$) of anthocyanin photoisomerization under different irradiation conditions.

| Anthocyanin source | Solvent | Concentration (μM) | Model | Initial cis/trans ratio (R$_i$) | Terminal cis/trans ratio (R$_t$) | Curve rate (k) | Time to equilibrium (min) | R$^2$ |
|---|---|---|---|---|---|---|---|---|
| Crude extract | 80% ethanol | 200 | | 0.044 | 0.670 | 0.28 | 20.9 | 0.996 |
| Crude extract | 80% ethanol | 300 | | 0.045 | 0.574 | 0.17 | 29.8 | 0.982 |

*Modified reciprocal squared function: Y(cis/trans ratio) = k * t$^{(-2)}$ + R$_t$

**Modified sigmoid function: $Y(\text{cis/trans ratio}) = (R_t - R_i)\left(\dfrac{2}{1 + e^{-kt}} - 1\right)$

***NA: Not Available

It was estimated from the model that the conversion of the cis reached a plateau phase at 22.1 min, being twice as much as that of the conversion from the trans (Table 2). Nevertheless, a longer equilibrium time does not necessarily mean a lower conversion efficiency. The reactions starting from either the cis or the trans achieved similar cis/trans ratios (~0.65) when equilibrium, thus the quantity of trans isomers generated from the reaction of cis isomers was more than twice as much as that of cis isomers generated from the isomerization of trans isomers. Considering the quantity of isomerization products generated and the time to reach an equilibrium, the cis→trans conversion was more efficient than its inverted reaction under the testing condition. Besides, the time to equilibrium may vary if a different threshold was chosen.

The mechanism of anthocyanin cis→trans and trans→cis photoisomerization have not been fully reported, while some progresses have been made on the photoisomerization of other compounds such as stilbene. Stilbene is a central ethylene moiety with one phenyl group substituents on each end of the carbon-carbon double bond. Research on stilbene demonstrated that the molecule arrived at its minimal potential energy when rotated to about 90° from either the cis or trans conformation, calling the phantom state. From this state, it can decay to the ground state to form an isomerization product, or alternatively invert back to the reactant. For stilbene, experiments suggested an energy barrier of ~0.15 eV in the isolated molecule for the trans→cis reaction, and a barrier of no more than 0.05 eV for the cis→trans reaction (Dou & Allen, 2003). The lower energy barrier of the latter conversion was expected to result in a higher conversion efficiency, which aligned with these observations.

Figure 4:
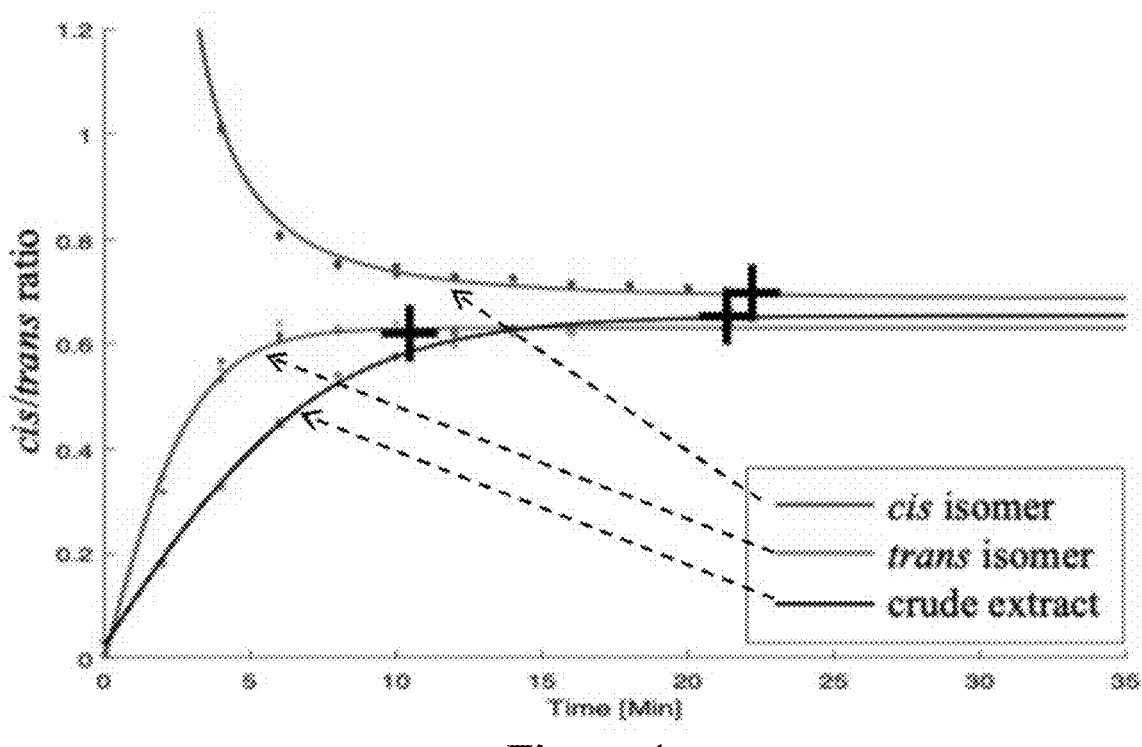
FIG. 4. Model fitting of cis/trans ratio of 100 μM cyanidin-3-p-coumaroyl-sambubioside-5-glucoside (cis- or trans-) and American elderberry crude extract under UV irradiation (254 nm). Cross marks indicate the photo-stationary phase.

Photoisomerization process of the American elderberry crude extract was monitored and compared to the reaction starting from the trans isolates to determine the impact of anthocyanin purity on the conversion efficiency. The cis/trans ratios after 4- or 16-min irradiation are shown in Table 1. The fitted model and the model parameters are shown in FIG. 4 and Table 2.

Anthocyanins in American elderberry crude extract was composed of ~65% trans-cyanidin-3-p-coumaroyl-sambubioside-5-glucoside, 2% of its cis isomers, with other anthocyanins, mostly non-acylated anthocyanin coexisted. Photoisomerization of the cyanidin-derived stereoisomers were successfully induced in the crude extract (FIG. 3). The initial cis/trans ratio in the crude extract was 0.033±0.001. This ratio was increased to 0.328±0.001 after 4-min UV irradiation, and further ascended to 0.629±0.009 after 16-min irradiation (FIG. 4). Compared to the isomerization of the trans isolates, the crude extract required longer time (21.5 min) to reach an equilibrium (Table 2). And the curve rate (k) of the trans isolates was higher than the crude extract, indicating a higher conversion efficiency. Nevertheless, the reaction of the trans isomers and the crude extract showed no significant differences on the cis/trans ratio after 12 min, and both reached an equilibrium at a cis/trans ratio of 0.63-0.65. The initial cis/trans ratio and the presence of other anthocyanins and polyphenols were likely to only influence the conversion efficiency but had little impact on the final conversion ratio. As starting with either the trans isomers or the crude extract provided a similar cis/trans ratio at the photo-stationary phase, the crude extract can be used directly as a starting material to explore the isomerization mechanism or produce more cis isomers.

Impact of solvent on photoisomerization reaction. The cis/trans ratios of the crude extract irradiated in ethanol-water system at 4- and 16-min are listed in Table 1. Photoisomerization of cyanidin derivatives readily occurred in all tested solvents even when small amount of energy was given. The initial cis/trans ratio in the crude extract was around 0.035. This ratio increased to 0.206 after 4-min irradiation in aqueous solvent, and further increased to 0.304 after 16-min irradiation (Table 1). The ratio obtained in this study was higher than that reported by Yoshida et al. (cis/trans: 0.17) when similar solvent (0.5% TFA-H$_2$O) and irradiation time (15 min) were applied (Yoshida et al., 2003). The different anthocyanin sources (stereoisomers of delphinidin derivatives used in Yoshida's study) and light sources (365 nm used by Yoshida et al.) might be responsible for such variations. In 100% acidified ethanol, the cis/trans ratio was 0.328 after 4 min-irradiation, being significantly higher than the ratio obtained in aqueous solution after 16-min irradiation, and further reached to 0.629 after 16-min irradiation. Photoisomerization of anthocyanins happened more rapidly and reached to a higher conversion ratio in ethanolic than aqueous solutions, consistent with the trend reported on other anthocyanin sources (Hayashi et al., 1997; Yoshida et al., 1990, 2003).

Figure 5:
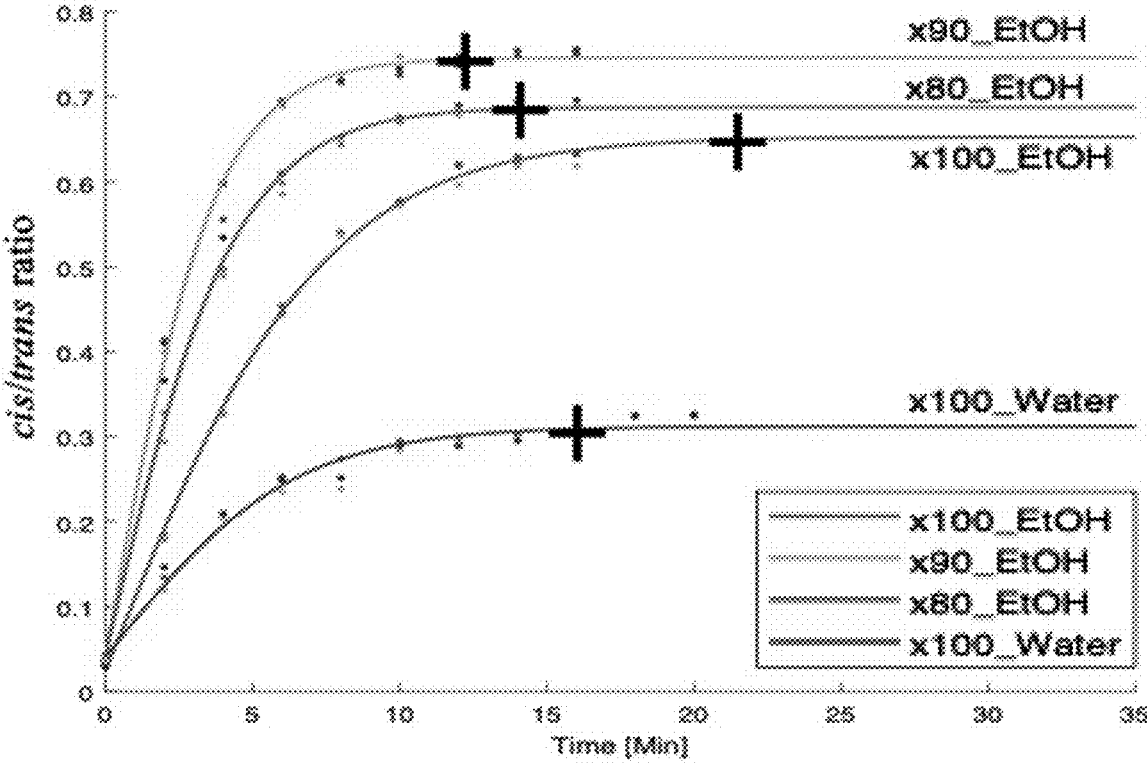
FIG. 5. Model fitting of cis/trans ratio of 100 μM anthocyanin in American elderberry crude extract during UV irradiation (254 nm) in 0.01% HCl acidified 100% H₂O, 80% ethanol, 90% ethanol, or 100% ethanol solutions. Cross marks indicate stable thresholds.

Higher cis/trans ratio was observed during the whole conversion process when 10-20% water was involved as compared to the pure ethanol (Table 1). In 90% ethanol, the cis/trans ratio was 0.585 at 4-min and increased to 0.753 after 16-min UV irradiation. In 80% ethanol, the cis/trans ratio was 0.507 at 4-min and increased to 0.691 after 16-min. Modelling of conversion process under each solvent showed that the photo-stationary phase was estimated to be obtained after 12.2 min irradiation with a cis/trans ratio of 0.746 in 90% ethanol (FIG. 5 and Table 2). The photo-stationary phase was estimated to be obtained after 14.0 min irradiation with a cis/trans ratio of 0.688 in 80% ethanol. In 100% ethanol, the extract reached a plateau at 21.5 min with a cis/trans ratio of 0.653; and in 100% water, the extract reached a plateau at 16.1 min with a cis/trans ratio of 0.312. The conversion efficiency, which was determined by the curve rate (k), was estimated to be the highest in 90% ethanol (0.54), followed by 80% ethanol (0.45), 100% $H_2O$ (0.32) and 100% ethanol (0.27). Considering the conversion efficiency and the cis/trans ratio at the stationary phase, acidified 90% ethanol would be a promising solvent used for anthocyanin photoisomerization.

Current knowledge on the relationship between anthocyanin photoisomerization and solvent are rather limited. Yet, the impact of solvent on the photoisomerization of other compounds, such as azobenzene, stilbene, and dihydroazulene has been examined (Dou & Allen, 2003; Quant et al., 2019). For example, a study on norbornadiene, a bicyclic hydrocarbon compound, showed that the quantum yield for the photoisomerization of norbornadiene was as low as 3% in acetonitrile solvent and was close to 30% in toluene solvent, the latter solvent being less polar than the former one. Further investigation on this compound and its analogues revealed that the photoisomerization of nonpolar compound was largely unaffected by solvent polarity, while for compounds polar at its ground state, they were expected to be more polar at the excited state due to charge transfer in the donor-acceptor structure, and bear stronger solvent effects (Quant et al., 2019). Anthocyanins are polar compounds due to the presence of multiple hydroxyl groups from aglycone and sugars, therefore their photoisomerization behavior was expected to be dependent on the solvent polarity. The relative polarities of ethanol, methanol and water are reported to be 0.654, 0.762, and 1 (Reichardt & Welton, 2010), which was correlated to the terminate cis/trans ratio obtained in the preliminary study (FIG. 1A-FIG. 1B). Therefore, it was hypothesized that the cis/trans ratio of anthocyanin photoisomerization at the stationary phase increased with the increasing of solvent polarity and dropped after passing certain point. The addition of small amount of water into ethanol increased the polarity of solvent, and consequently accelerated the conversion process. While further increasing of % $H_2O$ in ethanol-$H_2O$ increased solvent polarity and slowed down the isomerization efficiency.

Figure 2:
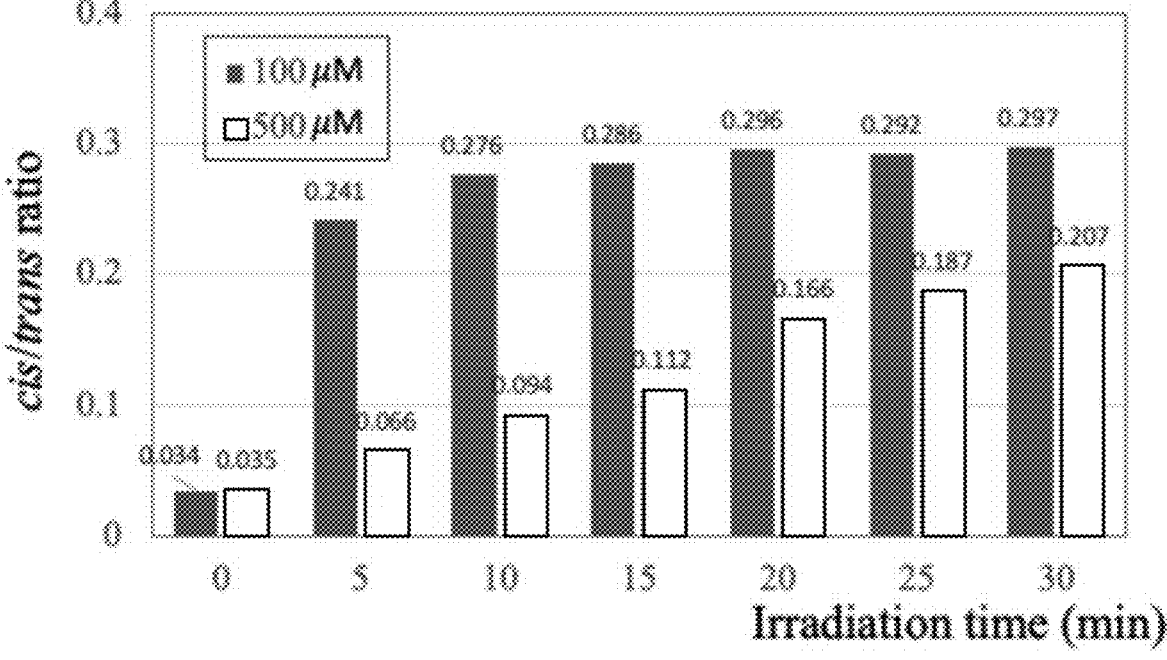
FIG. 2. The cis/trans ratio of 100 and 500 μM American elderberry crude extracts during 30 min UV irradiation (254 nm) in 100% HCl acidified water.

Determine the impact of anthocyanin concentration. A preliminary study has shown that the anthocyanin concentration also affected isomerization reaction, and higher cis/trans ratio was likely to be obtained under lower concentration (FIG. 2). Therefore, the crude extracts with the concentration of 100-300 µM were monitored for their photoisomerization process. The cis/trans ratio of 100 µM anthocyanin extract at 4 min was 0.507±0.025, being significantly higher than that of 200 and 300 µM crude extracts (Table 1). However, after 16 min irradiation, the 100 and 200 µM obtained similar cis/trans ratios with no significant difference between them. While both were significantly higher than that of 300 µM.

Figure 6:
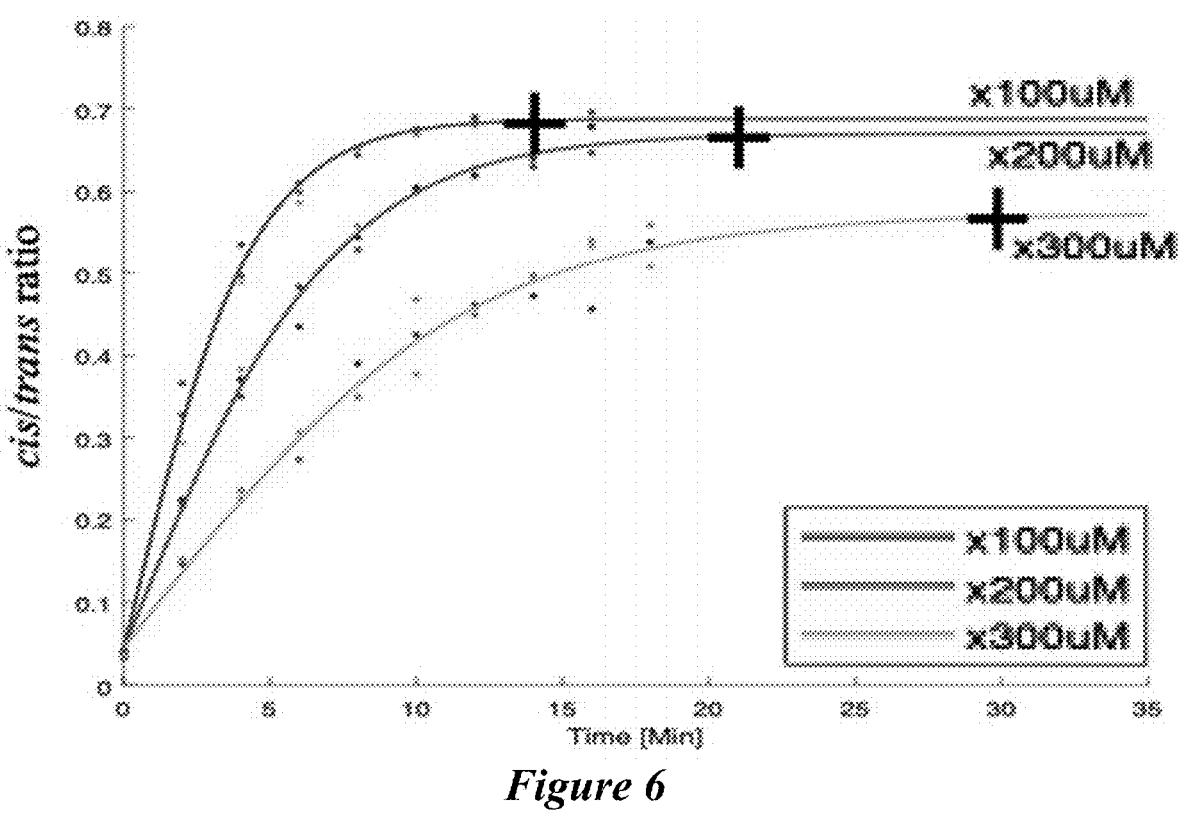
FIG. 6. Model fitting of cis/trans ratio of 100 μM, 200 μM, or 300 μM American elderberry crude extract during UV irradiation (254 nm) in 0.01% HCl acidified 80% ethanol. Cross marks indicate stable thresholds.

The fitted conversion models, model parameters and stable time were present in FIG. 6 and Table 2. The cis/trans ratio at the photo-stationary phase was estimated to be 0.688 for the 100 µM, 0.670 for the 200 µM and 0.574 for the 300 µM crude extracts (Table 1). As for the stable time, the 100 µM crude extract reached an equilibrium at 14 min, the 200 µM crude extract was equilibrated at 20.9 min and the 300 crude µM extract required almost 30 min to reach an equilibrium. Similar trend was observed on the curve rate that higher curve rate was obtained under lower concentration.

Photoisomerization reaction happens when the chromophore is excited by absorbing the light energy to its excited state. Such conversion needs to overcome an energy barrier. The cis-product would not be generated if the energy absorbed by the trans molecules was insufficient to overcome this barrier (Zhao et al., 2019). When certain amount of energy was imparted towards the system, higher anthocyanin content would "dilute" energy that single molecule received and resulted in a lower conversion rate. It was hypothesized that within certain limits, higher anthocyanin content only resulted in a lower conversion rate but did not affect the final cis/trans ratio greatly. However, when exceeded certain extend, the high anthocyanin content "overwhelmed" the energy system and caused a decrease on both conversion efficiency and final cis/trans ratio.

Although isomerization occurred faster at lower anthocyanin concentrations, higher quantity of cis isomers could be produced at higher concentration under the same irradiation time. Table 3 lists the estimated quantity of cis isomers in 100-300 µM American elderberry crude extracts during UV irradiation until the 100 µM extract reached a plateau phase (14 min). The estimated amount of cis isomers in 100 µM extract was constantly lower than that in 200 and 300 µM extracts. The latter two expressed no significant differences until 14 min. Extracts with higher anthocyanin content was likely to accumulate more cis isomers if sufficient irradiation time was given. To sum up, lower anthocyanin concentration resulted in higher conversion efficiency and the final cis/trans ratio was concentration dependent. And higher amount of cis isomers was tended to be produced when irradiated under higher anthocyanin content.

TABLE 3

Estimated quantity of cis isomers in the American elderberry crude extract after 4, 8, and 14 min UV irradiation (254 nm). In parenthesis are standard deviation.

| Anthocyanin concentration (µM) | Estimated quantity (µM) of cis isomers after: | | |
|---|---|---|---|
| | 4 min irradiation | 8 min irradiation | 14 min irradiation |
| 100 | 23.56 (0.75)[a] | 27.56 (0.11)[a] | 28.57 (0.19)[a] |
| 200 | 37.65 (1.25)[b] | 49.30 (0.85)[b] | 54.55 (0.42)[b] |
| 300 | 39.62 (0.80)[b] | 55.90 (2.62)[b] | 68.86 (1.33)[c] |

When comparing across all the testing conditions, the highest terminal cis/trans ratio was obtained by irradiating 100 µM crude extract in 90% ethanol (0.746), followed by the same crude extract irradiated in 80% ethanol (0.688). The lowest terminal cis/trans ratio was obtained when pure aqueous solution was applied (0.312) (Table 1). On the aspect of stable time, trans isomers reached to the plateau phase more rapidly than the crude extract, whereas the crude extract with higher anthocyanin concentration required more time to reach an equilibrium. Anthocyanin isomerization was generally the most efficient in ethanol solution with 100 µM trans isomers, followed by 100 µM crude extract in 90% ethanol, and the least efficient under high concentration, according to the estimated curve rates. Considering the feasibility, cost, food-friendly of practical application, UV irradiation of anthocyanin crude extract in 90% acidified ethanol with relative low concentration could be the most promising condition to trigger the production of cis isomers and potentially modulated the color expression of anthocyanin extracts.

Figure 7A:
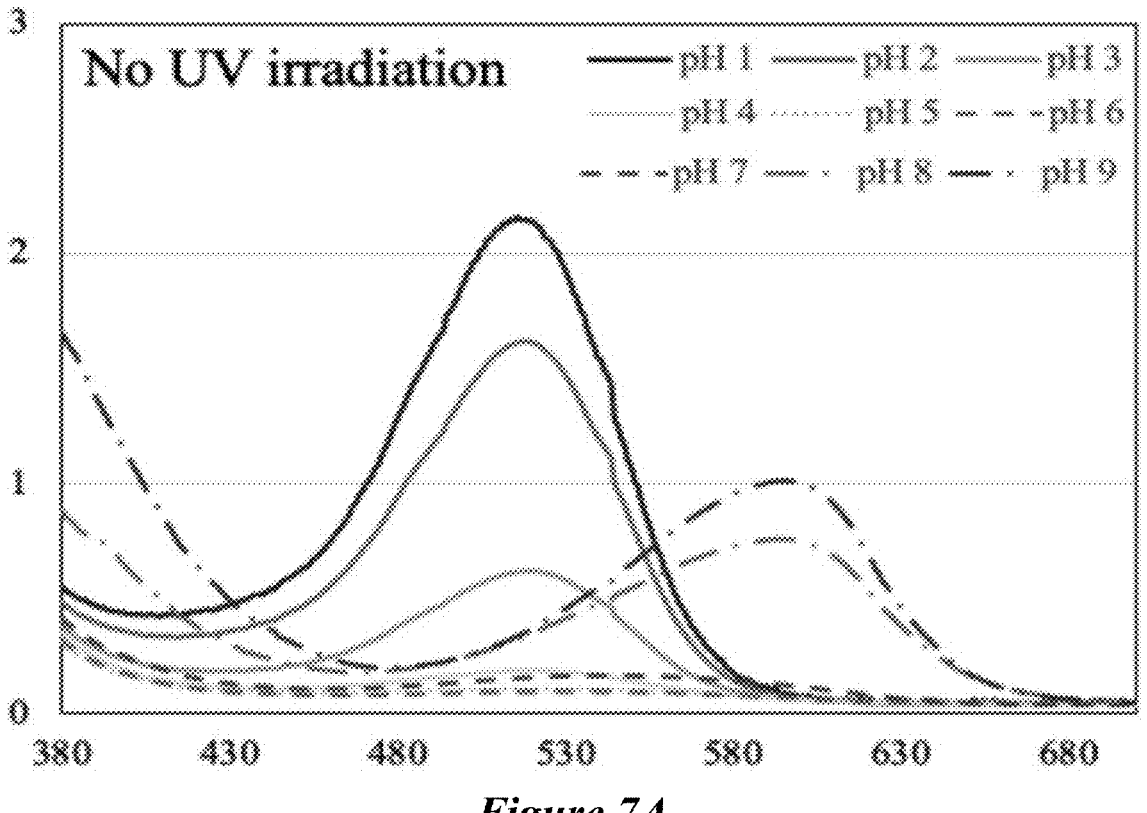
FIG. 7A. Visible spectra (380-700 nm) of 100 μM American elderberry crude extract before UV irradiation in pH 1-9 buffers (100 μM). Data was collected 1 h after mixing.
Figure 7B:
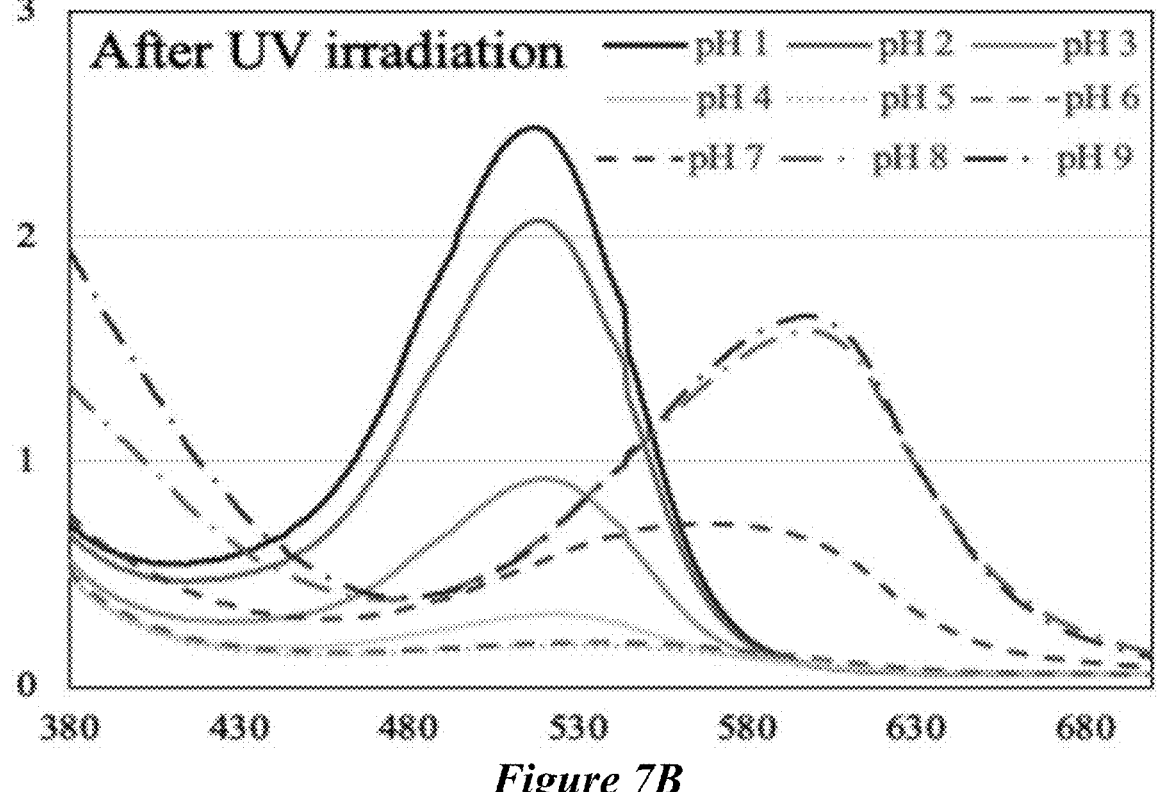
FIG. 7B. Visible spectra (380-700 nm) of 100 μM American elderberry crude extract after 12 min UV irradiation in pH 1-9 buffers (100 μM). Data was collected 1 h after mixing.

Impact of UV Irradiation on the Spectrophotometric Properties of American Elderberry Extract. UV irradiation induced both bathochromic and hyperchromic shifts on the visible spectrum of the crude extract (FIG. 7A-FIG. 7B). The UV irradiated extract displayed significant larger $\lambda_{vis-max}$ at pH 1-9 (Table 4).

bance retention (%), defined as a ratio of $A_{vis-max}$ between any pH higher than 1 and pH 1, was compared (Table 4). Similar to the observation on $A_{vis-max}$, the extract after UV irradiation achieved significantly larger % absorbance retention than the non-irradiated extract under all pHs. Both extracts retained more colors at acidic and alkaline pHs and experienced more color loss at low acidic to neutral pH.

Impact of UV irradiation on the color expression and stability of American elderberry extract. Color expression of

TABLE 4

$\lambda_{vis-max}$ (nm), absorbance at $\lambda_{vis-max}$ ($A_{vis-max}$), and % absorbance retention of American elderberry crude extract before and after UV irradiation (100 μM) in pH 1-9 buffers, n = 3. In parenthesis are standard deviations. Different superscripts indicate a significant difference (p < 0.05) between the extracts. (NA = not available)

| Extract treatment | pH 1 | pH 2 | pH 3 | pH 4 | pH 5 | pH 6 | pH 7 | pH 8 | pH 9 |
|---|---|---|---|---|---|---|---|---|---|
| | | | | $\lambda_{vis-max}$ (nm) | | | | | |
| No UV irradiation | 517 (1.2)[a] | 518 (0.6)[a] | 520 (0.0)[a] | 520 (1.0)[a] | 523 (2.5)[a] | NA | 563 (0.6)[a] | 594 (1.0)[a] | 596 (0.0)[a] |
| After UV irradiation | 521 (0.0)[b] | 521 (0.0)[b] | 523 (0.6)[b] | 524 (1.2)[b] | 533 (1.5)[b] | 535 (2.6) | 572 (1.2)[b] | 598 (0.6)[b] | 598 (0.6)[b] |
| | | | | Absorbance at $\lambda_{vis-max}$ ($A_{vis-max}$) | | | | | |
| No UV irradiation | 2.23 (0.07)[a] | 1.62 (0.07)[a] | 0.60 (0.02)[a] | 0.19 (0.01)a | 0.11 (0.01)[a] | NA | 0.14 (0.01)[a] | 0.77 (0.01)[a] | 1.00 (0.01)[a] |
| After UV irradiation | 2.40 (0.02)[b] | 2.09 (0.03)[b] | 1.12 (0.02)[b] | 0.41 (0.02)[b] | 0.23 (0.01)[b] | 0.25 (0.01) | 0.73 (0.01)[b] | 1.48 (0.02)[b] | 1.54 (0.04)[b] |
| | | | | % absorbance retention | | | | | |
| No UV irradiation | | 72.9 (4.0)[a] | 27.0 (1.8)[a] | 8.6 (0.2)[a] | 4.8 (0.3)[a] | NA | 6.4 (0.2)[a] | 34.4 (0.7)[a] | 44.8 (1.9)[a] |
| After UV irradiation | | 87.2 (1.0)[b] | 46.7 (0.4)[b] | 17.0 (0.8)[b] | 9.6 (0.3)[b] | 10.4 (0.4)[b] | 30.4 (0.3)[b] | 61.6 (1.0)[b] | 64.3 (1.4)[b] |

At pH 1-4, the $\lambda_{vis-max}$ of the UV irradiated extract was approximately 3-4 nm greater than the original crude extract. The cis isomers generally exhibited larger $\lambda_{vis-max}$ than the trans under pH from acidic to alkaline. The UV irradiation triggered anthocyanin trans→cis conversion, therefore shifted whole spectrum to longer wavelength and resulted in bluer color hues.

The American elderberry crude extract, after UV irradiation, exhibited significantly higher absorption at $\lambda_{vis-max}$ ($A_{vis-max}$) under all pHs (FIG. 7A-FIG. 7B and Table 4). The $A_{vis-max}$ of the original and UV irradiated extracts at pH 1 were 2.23 and 2.40, respectively. The differences of $A_{vis-max}$ between the two became more pronounced with pH increasing. At pH 3-5, the $A_{vis-max}$ of the UV irradiated extract was approximately twice as much as that of the non-UV irradiated extract. At pH 6, the crude extract without UV irradiation was almost completed bleached due to the formation of colorless hemiketal forms and its $A_{vis-max}$ at this pH was negligible. While the extract still retained absorption ($A_{vis-max}$=0.25±0.01) after UV irradiation, due to the formation of cis isomers through photoisomerization. The most pronounced differences between the two was shown at pH 7, at which the $A_{vis-max}$ of the UV irradiated extract more than 5 times higher than the other one. Differences on the $A_{vis-max}$ between the two extracts were strongly correlated with the spectral characteristics of the cis and trans isomers under each pH, that this pair of stereoisomers exhibited the greatest differences on $A_{vis-max}$ at pH 3-7, and less variations at pH 1-2 and 8-9.

Figures 8, 9:
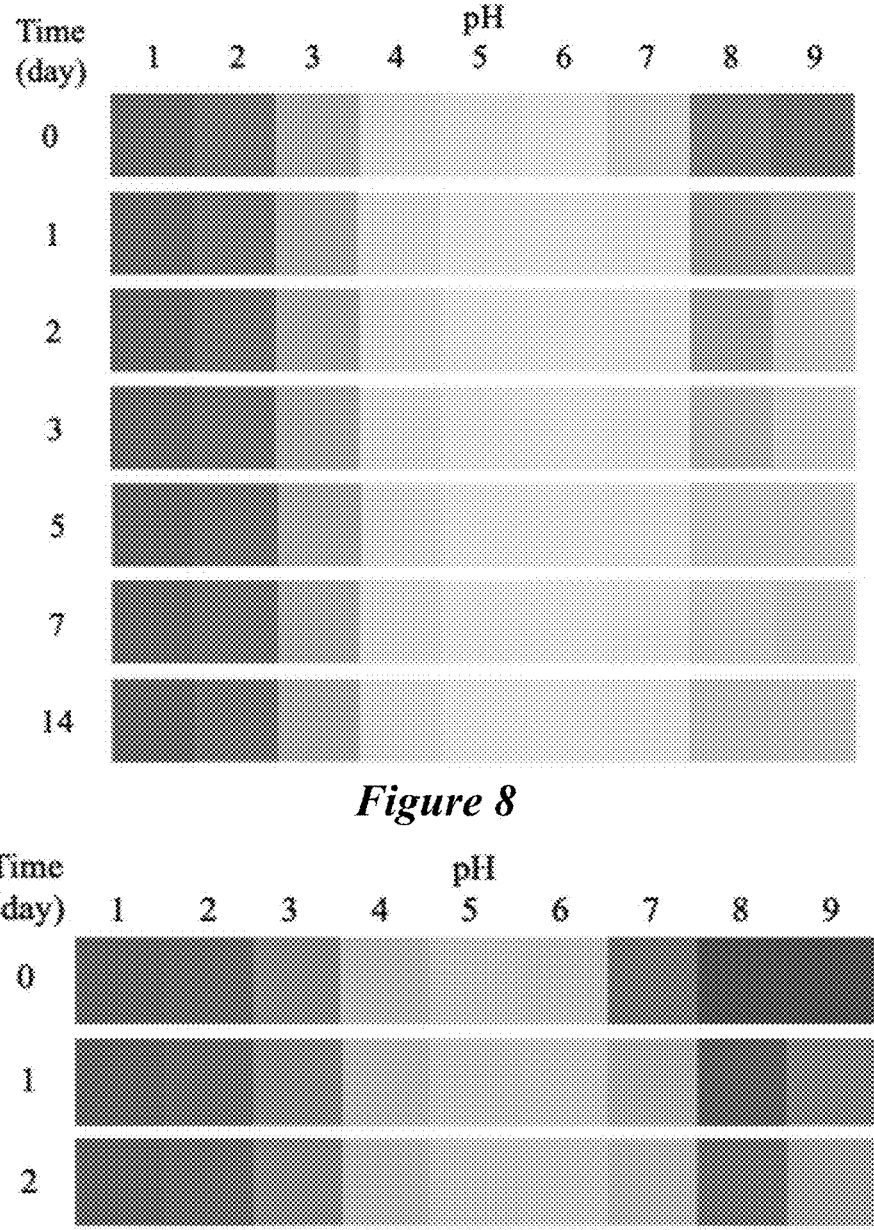
FIG. 8. Color swatches of non-irradiated American elderberry crude extract (100 μM) in pH 1-9 buffers during storage (4° C. in dark). The initial color data was collected 1 hr after mixing.
FIG. 9. Color swatches of American elderberry crude extract (100 μM) after 12 min UV irradiation (90% ethanol) in pH 1-9 buffers during storage (4° C. in dark). The initial color data was collected 1 hr after mixing.

Considering the possible unequal anthocyanin concentrations between the two extracts caused by unknown molar absorptivity (ε) of individual anthocyanin, relative absorthe crude extract before and after UV irradiation during storage were visualized in FIG. 8-FIG. 9 using color swatches. At acidic pH, the L* of both extracts increased and the $C^*_{ab}$ decreased with pH increasing (Table 5). The extract after UV irradiation displayed significantly smaller L* and larger $C^*_{ab}$ than the extract without UV irradiation, meaning that the former one constantly expressed darker and more saturated colors than the latter. The $h^*_{ab}$ of the UV-treated extract was 2.3-5.3° larger than the non-treated extract. Therefore, UV irradiation shifted the color hue of the extract towards more orange-red shades under acidic pH. Color properties of American elderberry crude extract modulated by UV light was consistent with the different colorimetric behaviors of the cis and trans isomers discussed elsewhere, in which the cis acylation exhibited smaller L*, and larger $C^*_{ab}$ and $h^*_{ab}$ at acidic pH. Both extracts experienced negligible changes at $A_{vis-max}$ during the storage time frame (4-week), therefore, the half-lives of both extracts under this pH range were not determined.

More remarkable differences were observed between the two extracts at pH 4-6, where the L* of the extract became 7-9 unites smaller, and the $C^*_{ab}$ became 2-3.3 times larger after UV irradiation (Table 5). The American elderberry extract bleached thoroughly at low acidic pH due to the abundant cyanidin-3,5-glycosides it contained. Its negligible coloring capacity at this pH range restricted its application in food. The UV irradiation multiplied the amount of cis isomers in the extract, and considerably improved its tinctorial capacity under this pH range. Although the color of the extract shown at pH 4-6 was still not so vibrant after UV irradiation, it can be applied on some products that requires mild and lighter pink colors. Half-lives of the extracts before and after UV irradiation were calculated to be 1246.3 hours (~52 days) and 2951.1 (~123 days), respectively. However, since the extract without irradiation showed overall pale color, it was expectable that little color change was observed over time.

The UV induced color change on the crude extract behaved similarly at pH 7 and 9 that the UV irradiation significantly intensified the initial color expression while colors quickly disappeared during storage. At the initial time point, the L* of the extract after irradiation was 27.8 units smaller, and the $C^*_{ab}$ was nearly 5 times larger than that of the crude extract (Table 5). However, the differences on L* between the two quickly reduced to ~10 units and less than twofold on $C^*_{ab}$ after 24 hours. This was in agreement with the cis and trans isomers' colorimetric and stability attributes determined elsewhere, in that the cis and the trans isomers varied considerably on the L* and $C^*_{ab}$ but less varied on half-lives. Apparently, the extract before irradiation exhibited longer half-lives than the one after irradiation at pH 7 (Table 6). It did not indicate higher stability but was more resulted from its initial weak coloring capacity.

At pH 8, UV irradiation resulted in darker and more saturated (smaller L* and larger $C^*_{ab}$) blue hues)(~257°) with no significant effect on the hue angle (Table 6). The replacement of synthetic blue dyes was particularly challenging. Anthocyanin-based blue colors can easily get lost unless metal ions present or using heavily substituted anthocyanin sources (Sigurdson et al., 2017). However, anthocyanin-metal ion complex might be questioned about its "nature", and the heavily substituted anthocyanins are not commonly found in edible source. Therefore, the UV irradiation provided a new approach to obtain more stable and "bluer" hues from anthocyanins source. Although the two extracts showed similar half-lives, the extract after UV irradiation constantly produced darker colors and kept the $h^*_{ab}$ in the region of blue hues for longer time.

Conclusion. Anthocyanin trans↔cis conversion occurred under UV irradiation and the status at photostationary phase depending on starting materials, solvents, and anthocyanin concentrations. The increasing of the isomerized products could be modelled by a sigmoid function. The calculated conversion efficiency was higher for cis→trans reaction than

TABLE 5

Colorimetric properties (CIE L*, $C^*_{ab}$, $h^*_{ab}$) of UV irradiated and non-irradiated American elderberry crude extract (100 μM) in pH 1-9 buffers. Data was collected 1 hr after mixing. In parenthesis are standard deviations. Different superscripts indicate a significant difference (p < 0.05) among extracts.

| Extract treatment | pH 1 | pH 2 | pH 3 | pH 4 | pH 5 | pH 6 | pH 7 | pH 8 | pH 9 |
|---|---|---|---|---|---|---|---|---|---|
| | | | | Lightness (L*) | | | | | |
| No UV irradiation | 63.2 (0.3)[a] | 66.9 (0.6)[a] | 79.1 (0.6)[a] | 89.6 (0.2)[a] | 92.4 (0.1)[a] | 92.6 (0.3)[a] | 88.0 (0.1)[a] | 65.6 (0.2)[a] | 61.9 (0.3)[a] |
| After UV irradiation | 61.3 (0.6)[b] | 62.4 (0.3)[b] | 69.3 (0.4)[b] | 81.0 (0.6)[b] | 85.4 (0.5)[b] | 83.6 (0.9)[b] | 60.2 (0.3)[b] | 48.9 (0.7)[b] | 48.0 (0.6)[b] |
| | | | | Chroma ($C^*_{ab}$) | | | | | |
| No UV irradiation | 69.5 (0.7)[a] | 64.0 (0.9)[a] | 38.2 (1.1)[a] | 11.5 (0.6)[a] | 4.1 (0.4)[a] | 3.3 (0.3)[a] | 6.2 (0.1)[a] | 25.4 (0.3)[a] | 26.5 (0.2)[a] |
| After UV irradiation | 70.9 (0.4)[a] | 68.2 (0.4)[b] | 55.0 (0.3)[b] | 25.6 (1.2)[b] | 11.8 (0.5)[b] | 10.9 (0.0)[b] | 30.0 (0.3)[b] | 35.3 (0.3)[b] | 26.6 (0.3)[a] |
| | | | | Hue angle ($h^*_{ab}$) | | | | | |
| No UV irradiation | 15.0 (0.8)[a] | 7.3 (0.7)[a] | 357.4 (0.1)[a] | 4.0 (0.7)[a] | 26.3 (1.1)[a] | 29.5 (2.5)[a] | 344.5 (0.2)[a] | 256.8 (0.3)[a] | 232.7 (0.3)[a] |
| After UV irradiation | 17.3 (0.1)[b] | 12.6 (0.4)[b] | 1.7 (0.2)[b] | 356.9 (0.5)[b] | 0.9 (1.3)[b] | 353.2 (1.3)[b] | 303.8 (0.2)[b] | 256.6 (0.4)[a] | 224.1 (0.5)[b] |

TABLE 6

Kinetic parameters (k and half-lives (hour)) for the degradation of the American elderberry crude extract (100 μM) before and after UV irradiation in pH 4-9 buffer during storage (4° C. in dark). Numbers in parentheses are the standard deviations.

| Extract treatment | pH 4 | pH 5 | pH 6 | pH 7 | pH 8 | pH 9 |
|---|---|---|---|---|---|---|
| | | | k * 10^{-3} | | | |
| No UV irradiation | 0.60 (0.04) | NA | NA | 0.63 (0.06) | 5.91 (0.06) | 4.72 (0.01) |
| After UV irradiation | 0.24 (0.01) | 0.62 (0.02) | 0.80 (0.03) | 2.52 (0.00) | 4.97 (0.00) | 5.75 (0.01) |
| | | | $t_{1/2}$ (hr) | | | |
| No UV irradiation | 1246.3 (188.5)[a] | NA | NA | 1106.5 (109.0)[b] | 116.9 (1.3)[a] | 147.0 (6.1)[b] |
| After UV irradiation | 2951.1 (350.8)[b] | 1108.3 (33.4) | 862.9 (24.6) | 274.8 (3.4)[a] | 116.9 (1.3)[a] | 120.7 (4.8)[a] | its reversed reaction, suggesting a lower energy barrier for this direction. The reactions starting from the crude extract and isolates reached similar cis/trans ratios (~0.65) at the stationary phase with more time needed by the crude extract. Anthocyanin isomerization was governed by solvents that higher cis/trans ratio and conversion efficiency were obtained in organic solvents than the aqueous. Whereas the highest conversion rate was obtained in 80-90% ethanol (~0.75). It seemed that the anthocyanin photoisomerization efficiency was associated with the solvent polarity and the conversion efficiency increased with the increasing of polarity and quickly decreased after passing certain value. Anthocyanin photoisomerization was also concentration-dependent that the conversion happened faster under lower concentration. The terminal cis/trans ratio might vary if the anthocyanin concentration overwhelmed. Nevertheless, higher quantity of the cis isomers tended be obtained under higher concentration, especially when longer UV exposure time was applied. Anthocyanin photoisomerization was recommended to conducted with anthocyanin crude extract in 90% ethanol under lower concentration to achieve a high conversion efficiency in a food-friendly environment.

Irradiation of American elderberry crude extract by UV light (254 nm) resulted in sharper visible spectra, darker and more saturated color expression, especially under pH 5-6, and more intense and stable blue colors at pH 8, due to the isomerization of the trans to the cis. As UV radiation has been approved by FDA to be used on fruit juice, UV irradiation can be a safe and sustainable approach to enhance the color performance of anthocyanin-based food colorants.

BIBLIOGRAPHY

Ahmadiani et al. (2014). Anthocyanins contents, profiles, and color characteristics of red cabbage extracts from different cultivars and maturity stages. *Journal of Agricultural and Food Chemistry*, 62(30), 7524-7531. https://doi.org/10.1021/jf501991q Andersen et al. (2005). The Anthocyanins. In *Flavonoids*. https://doi.org/10.1201/9781420039443.ch10

Andersen et al. (2005). Flavonoids: Chemistry, biochemistry and applications. In *Flavonoids: Chemistry, Biochemistry and Applications*. https://doi.org/10.1201/9781420039443

Byers et al. (2012). Growing and marketing elderberries in Missouri. *Extension Publications* (MU).

Charlebois et al. (2010). Elderberry: Botany, Horticulture, Potential. *Horticultural Reviews*, 37, 213-280. https://doi.org/10.1002/9780470543672.ch4

Chen et al. (2017). Characterizing Red Radish Pigment Off-Odor and Aroma-Active Compounds by Sensory Evaluation, Gas Chromatography-Mass Spectrometry/Olfactometry and Partial Least Square Regression. *Food and Bioprocess Technology*, 10(7), 1337-1353. https://doi.org/10.1007/s11947-017-1904-5

Csorba et al. (2020). Cultivar and year effects on the chemical composition of elderberry (*Sambucus nigra* L.) fruits. *Notulae Botanicae Horti Agrobotanici Cluj-Napoca*, 48(2), 770-782. https://doi.org/10.15835/nbha48211873

Dou et al. (2003). Detailed dynamics of a complex photochemical reaction: Cis-trans photoisomerization of stilbene. *Journal of Chemical Physics*, 119(20), 10658-10666. https://doi.org/10.1063/1.1621621

FDA. (2016). *Listing of Color Additives Exempt from Certification*. 1st April.

Ferreira et al. (2019). *Effect of harvesting year and elderberry cultivar on the chemical composition and potential bioactivity: A three-year study*. https://doi.org/10.1016/j.foodchem.2019.125366

Food and Drug Administration (FDA). (2019). CFR Code of Federal Regulations Title 21 FOOD AND DRUGS. Www.Fda.Gov.

Food and Drug Administration (FDA). (2020). CFR. Title 21.

Garcia-Beneytez et al. (2003). Analysis of grape and wine anthocyanins by HPLC-MS. *Journal of Agricultural and Food Chemistry*, 51(19), 5622-5629. https://doi.org/10.1021/jf030220

George et al. (2001). Influence of trans-cis isomerisation of coumaric acid substituents on colour variance and stabilisation in anthocyanins. *Phytochemistry*. https://doi.org/10.1016/S0031-9422(01)00105-4

Gibbs et al. (2000). Variational Gaussian process classifiers. *IEEE Transactions on Neural Networks*, 11(6), 1458-1464. https://doi.org/10.1109/72.883477

Giusti et al. (2001). Characterization and measurement of anthocyanins by UV-visible spectroscopy. In *Current protocols in food analytical chemistry* (pp. 19-32). http://www.academia.edu/6873755/Characterization_and-_Measurement_of_Anthocyanins_by_UV-Visible_Spectroscopy Giusti et al. (2003). Acylated anthocyanins from edible sources and their applications in food systems. *Biochemical Engineering Journal*, 14(3), 217-225. https://doi.org/10.1016/S1369-703X(02)00221-8

Hayashi et al. (1997). Note Photo-Isomerization of the Nasunin, the Major Eggplant Anthocyanins. In *Food Sci. Technol. Int. Tokyo* (Vol. 4, Issue I).

He et al. (2010). Different anthocyanin profiles of the skin and the pulp of Yan73 (muscat hamburg×alicante bouschet) grape berries. *Molecules*, 15(3), 1141-1153. https://doi.org/10.3390/molecules15031141

Ichiyanagi et al. (2005). Nasunin from eggplant consists of cis-trans isomers of delphinidin 3-[4-(p-coumaroyl)-L-rhamnosyl (1→6)glucopyranoside]-5-glucopyranoside. *Journal of Agricultural and Food Chemistry*, 53(24), 9472-9477. https://doi.org/10.1021/jf051841y Lee et al. (2007). Anthocyanins and other polyphenolics in American elderberry (*Sambucus canadensis*) and European elderberry (*S. nigra*) cultivars. *Journal of the Science of Food and Agriculture*, 87(August 2007), 2665-2675. https://doi.org/10.1002/jsfa Lewis et al. (1989). The singlet states of methyl cinnamate and methyl indenoate. *Journal of Photochemistry and Photobiology, A: Chemistry*, 47(2), 173-179. https://doi.org/10.1016/1010-6030(89)87063-7

Martin et al. (2017). Anthocyanin Pigments: Importance, Sample Preparation and Extraction. In *Phenolic Compounds—Natural Sources, Importance and Applications*. InTech. https://doi.org/10.5772/66892

Mlynarczyk et al. (2020). The Content of Selected Minerals, Bioactive Compounds, and the Antioxidant Properties of the Flowers and Fruit of Selected Cultivars and Wildly Growing Plants of *Sambucus nigra* L. *Molecules*, 25(4), 876. https://doi.org/10.3390/molecules25040876

Ozgen et al. (2010). Total phenolic, anthocyanin contents and antioxidant capacity of selected elderberry (*Sambucus canadensis* L.) accessions. *Pharmacognosy Magazine*, 6(23), 198-203. https://doi.org/10.4103/0973-1296.66936

Perkins-Veazie et al. (2015). Fruit composition of elderberry (*Sambucus* spp.) genotypes grown in Oregon and Missouri, USA. *Acta Horticulturae*, 1061(2013), 219-224. https://doi.org/10.17660/ActaHortic.2015.1061.24

Potra et al. (2000). Interior-point methods. *Journal of Computational and Applied Mathematics*, 124(1-2), 281-302. https://doi.org/10.1016/S0377-0427(00)00433-7

Prior et al. (1998). Antioxidant Capacity as Influenced by Total Phenolic and Anthocyanin Content, Maturity, and Variety of Vaccinium Species. *Journal of Agricultural and Food Chemistry*, 46(7), 2686-2693. https://doi.org/10.1021/jf980145d Purgar et al. (2012). A comparison of fruit chemical characteristics of two wild grown Rubus species from different locations of Croatia. *Molecules*, 17(9), 10390-10398. https://doi.org/10.3390/molecules170910390

Quant et al. (2019). Solvent Effects on the Absorption Profile, Kinetic Stability, and Photoisomerization Process of the Norbornadiene-Quadricyclanes System. *Journal of Physical Chemistry C*, 123(12), 7081-7087. https://doi.org/10.1021/acs.jpcc.9b02111

Reichardt et al. (2010). Empirical Parameters of Solvent Polarity. In *Solvents and Solvent Effects in Organic Chemistry* (pp. 425-508). Wiley-VCH Verlag GmbH & Co. KGaA. https://doi.org/10.1002/9783527632220.ch7

Rodriguez-Saona et al. (2002). Extraction, isolation, and purification of anthocyanins. In *Current protocols in food analytical chemistry.*

Rodriguez et al. (2020). Understanding the role played by protic ionic liquids (PILs) and the substituent effect for enhancing the generation of Z-cinnamic acid derivatives †. *Cite This: Photochem. Photobiol. Sci*, 19,819. https://doi.org/10.1039/d0pp00072h Sadilova et al. (2006). Anthocyanins, colour and antioxidant properties of eggplant (*Solanum melongena* L.) and violet pepper (*Capsicum annuum* L.) peel extracts. *Zeitschrift Fur Naturforschung—Section C Journal of Biosciences,* 61(7-8), 527-535. https://doi.org/10.1515/znc-2006-7-810

Salum et al. (2010). Photoisomerization of ionic liquid ammonium cinnamates: One-pot synthesis-isolation of Z-cinnamic acids. *Organic Letters,* 12(21), 4808-4811. https://doi.org/10.1021/ol11019508

Salum et al. (2013). High purity cis-cinnamic acid preparation for studying physiological role of trans-cinnamic and cis-cinnamic acids in higher plants. *Environmental Control in Biology,* 51(1), 1-10. https://doi.org/10.2525/ecb.51.1

Schmid et al. (1994). Revision of the Genus Sambucus. *Taxon.* https://doi.org/10.2307/1223564

Sigurdson et al. (2018). Impact of location, type, and number of glycosidic substitutions on the color expression of o-dihydroxylated anthocyanidins. *Food Chemistry,* 268 (February), 416-423. https://doi.org/10.1016/j.foodchem.2018.06.079

Sigurdson et al. (2019). Molar absorptivities (ε) and spectral and colorimetric characteristics of purple sweet potato anthocyanins. *Food Chemistry,* 271(April 2018), 497-504. https://doi.org/10.1016/j.foodchem.2018.07.096

Sigurdson et al. (2017). Natural Colorants: Food Colorants from Natural Sources. *Annual Review of Food Science and Technology,* 8(1), 261-280. https://doi.org/10.1146/annurev-food-030216-025923

Sigurdson et al. (2018). Cis-trans configuration of coumaric acid acylation affects the spectral and colorimetric properties of anthocyanins. *Molecules,* 23(3). https://doi.org/10.3390/molecules23030598

Sun et al. (2002). Effect of Food Processing on Bioactive Compounds in Foods: A New Method for Separation and Identification of cis-Cinnamic Acid from Its Racemic Mixture. *ACS Symposium Series,* 816, 228-240. https://doi.org/10.1021/bk-2002-0816.ch017

Szalóki-Dorkó et al. (2015). Evaluation of colouring ability of main European elderberry (*Sambucus nigra* L.) varieties as potential resources of natural food colourants. *International Journal of Food Science and Technology,* 50(6), 1317-1323. https://doi.org/10.1111/ijfs.12773

Tang et al. (2018). Black goji as a potential source of natural color in a wide pH range. *Food Chemistry,* 269(February), 419-426. https://doi.org/10.1016/j.foodchem.2018.07.034

Wallace et al. (2015). Anthocyanins. *Advances in Nutrition,* 6(5), 619-622. https://doi.org/10.3945/an.115.009233

Waterhouse. (2002). Determination of total phenolics. In *Current protocols in food analytical chemistry* (pp. 463-469).

Wilson et al. (2016). Growing Elderberries: A Production Manual and Enterprise Viability Guide for Vermont and the Northeast. *UVM Center for Sustainable Agriculture.*

Wu et al. (2004). Characterization of anthocyanins and proanthocyanidins in some cultivars of *Ribes, Aronia,* and *Sambucus* and their antioxidant capacity. *Journal of Agricultural and Food Chemistry,* 52(26), 7846-7856. https://doi.org/10.1021/jf0486850

Yin et al. (2003). Biologically active cis-cinnamic acid occurs naturally in *Brassica parachinensis. Chinese Science Bulletin,* 48(6), 555-558. https://doi.org/10.1360/03tb9118

Yoshida et al. (1990). Structure of anthocyanins isolated from purple leaves of perilla ocimoides 1. Var. Crispa benth and their isomerization by irradiation of light. *Agricultural and Biological Chemistry,* 54(7), 1745-1751. https://doi.org/10.1080/00021369.1990.10870188

Yoshida et al. (2003). Influence of E,Z-isomerization and stability of acylated anthocyanins under the UV irradiation. *Biochemical Engineering Journal,* 14(3), 163-169. https://doi.org/10.1016/S1369-703X(02)00217-6

Zhao et al. (2014). Structure-activity relationships of anthocyanidin glycosylation. *Molecular Diversity,* 18(3), 687-700. https://doi.org/10.1007/s11030-014-9520-z Zhao et al. (2017). Stability-increasing effects of anthocyanin glycosyl acylation. *Food Chemistry,* 214, 119-128. https://doi.org/10.1016/j.foodchem.2016.07.073

Zhao et al. (2019). Does the wavelength dependent photoisomerization process of the p-coumaric acid come out from the electronic state dependent pathways? *Spectrochimica Acta—Part A: Molecular and Biomolecular Spectroscopy,* 211, 203-211. https://doi.org/10.1016/j.saa.2018.12.010

Zhou et al. (2020). Accumulation of anthocyanins and other phytochemicals in american elderberry cultivars during fruit ripening and its impact on color expression. *Plants,* 9(12), 1-14. https://doi.org/10.3390/plants9121721

Zhou et al. (2016). Frugivory by Brown Marmorated Stink Bug (Hemiptera: Pentatomidae) Alters Blueberry Fruit Chemistry and Preference by Conspecifics. *Environmental Entomology,* 45(5), 1227-1234. https://doi.org/10.1093/ee/nvw110

Example 2—Efficient Method for
Anthocyanin-Based Colorants Performance
Enhancement Through UV Irradiation Described herein is a UV-based method for efficiently modifying the conformation of acylated anthocyanins to enhance the color expression and stability of anthocyanin-based colorants rich in hydroxycinnamic acid acylations. An advantage to this methods is that FDA-approved UV light is used to include a reaction in food-friendly solvents (water and ethanol), and external addition of stabilizing compounds is reduced or eliminated. In some examples, the reaction conditions can be selected to minimize degradation of the anthocyanin. The methods described herein can provide alternatives to synthetic colorants by expanding the color performance of anthocyanins. This contributes to natural colorants' role in offering various colors to make foods more appealing.

Example 3—Ultraviolet-Visible Excitation of cis-
and trans-p-coumaric Acylated Delphinidins and
Their Resulting Photochromic Characteristics Abstract. Anthocyanins are often acylated with trans-hydroxycinnamic acids, but can undergo a structural transformation to their cis-isomer. This study investigated the reversible photochromism of trans- and cis-acylated del-

Figures 10, 11:
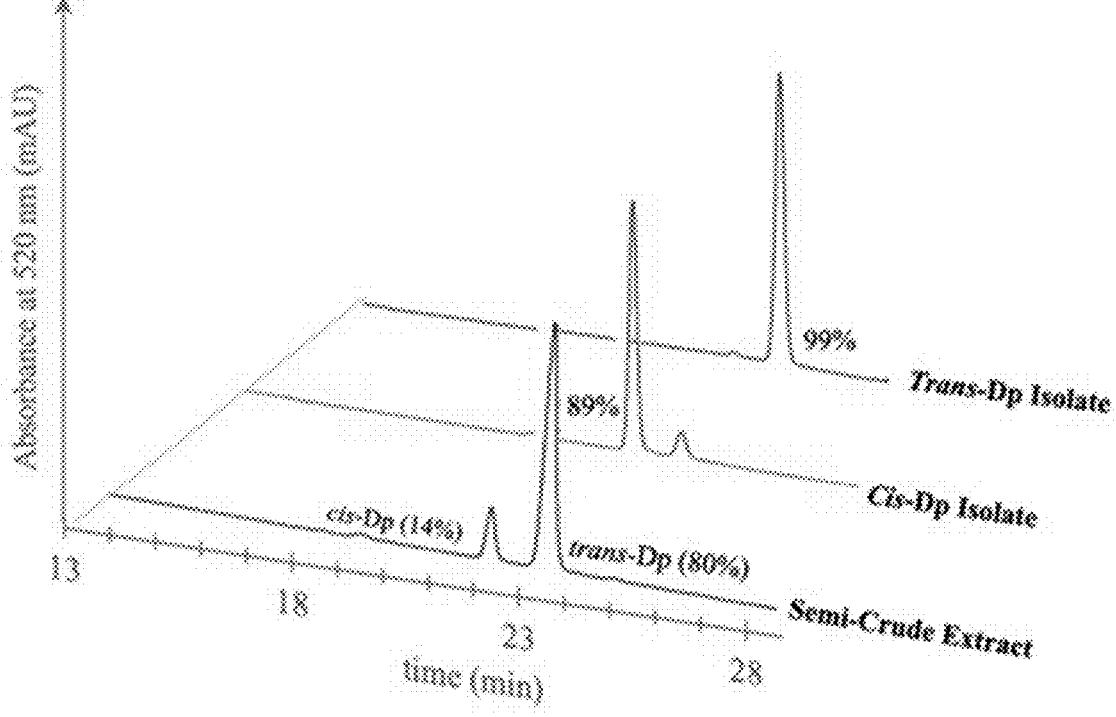
FIG. 10. Reversible isomerization of trans-Dp and cis-Dp as a result of excitation with light. The two differing sizes of the arrows represent the favoring of the chemical equilibrium dominated by trans-Dp.
FIG. 11. HPLC-PDA chromatogram of Semi-Crude Extract (SCE) from East Asian eggplants after semi-purification with a C18 cartridge. Cis-Dp and trans-Dp isolates represent the PDA chromatograms of the peaks isolated from semi-crude extract. Individual peak % was calculated as % of the total area under the curve when peaks were detected at 520 nm.

33 phinidin derivatives (Dp) under industry accessible ultraviolet (UV) and visible energies, and their impact on color expression (FIG. 10). Delphinidin-3-(trans-p-coumaroyl)-rutinoside-5-glucoside, delphinidin-3-(cis-p-coumaroyl)-rutinoside-5-glucoside, and its mixture were subjected to UV and visible light for up to 20 hours. Isomerization was monitored using HPLC-PDA. Color, spectra, and stability were compared using a spectrophotometer and ColorBySpectra software. All light treatments induced photoisomerization between trans and cis-acylated Dp, but to varying extents, equilibria, and at different exposure times. Visible energy induced greater trans-to-cis isomerization, while UV induced greater cis-to-trans isomerization. Cis-Dp showed greater color intensity and stability in pH 1, and greener hue ($h^*_{ab}$ 130°) than trans-Dp ($h^*_{ab}$ 188°) in pH 8 after equilibration of 15 minutes.

Introduction. Anthocyanins (ACN) are phytochemical pigments with health-promoting properties that can be used as food colorants [1,2]. Anthocyanins come from different plant sources, and have the potential to express a wide variety of colors, ranging from orange to blue, depending on the pH conditions [3]. However, their color stability is limited when compared to synthetic dye counterparts. Researchers have used colloidal complexation or co-pigmentation to retain or enhance the color of anthocyanins with a variety of biopolymers, phenolic compounds, and metals [4-6]. Although combining these strategies can help to stabilize the product's color characteristics, the use of colloids or co-pigments can alter the solubility of the matrix or the flavor of the product [5]. Therefore, stabilization of anthocyanins via chemical structural manipulation, such as photoisomerization, is a promising strategy.

Anthocyanins have a flavylium base structure and a variety of methoxylation, glycosylation, hydroxylation, and acylation patterns that make up over 700 molecular structures [8]. In general, greater attachments of glycosylation and acylation on the aglycone backbone have been associated with greater pigment stability and color expression [9,10]. Anthocyanins can be acylated with aliphatic acids, such as malonic and malic acid, as well as hydroxycinnamic acids, such as p-coumaric, ferulic, and caffeic acid. Most studies have alluded to hydroxycinnamic acylation's role in increasing pigment stability as a result of both intramolecular and intermolecular co-pigmentation [11]. Hydroxycinnamic acids can exist in either in its trans- or cis-configuration, however, trans-isomers are known to be highly prevalent in nature [12]. A previous study showed that cis-acylated anthocyanins may exhibit increased color strength and stability than their trans-counterparts [13]. However, since cis-acylated anthocyanins are difficult to find, photoisomerization of naturally abundant trans-acylated anthocyanins to form the rare pigment was studied here [14].

Photoisomerization of anthocyanins is often discussed in terms of the ground state transitions of chalcones as a result of change in pH and light [15-18]. The photoisomerization that occurs during the flavylium multistate of trans-chalcone to cis-chalcone depends on the isomerization barrier as well as the pH, as postulated by the energy diagram described by Basilio and Pina [19], which was adopted from the reaction rates and equilibrium constants of the trans- and cis-chalcone isomerization [20, 21]. Photoisomerization of hydroxycinnamic acylations of anthocyanins have had less attention and there is much more to be discovered. Earlier works by Yoshida et al. [22] and Hayashi et al. [23] showed that delphinidins acylated with p-coumaric acid can undergo photoisomerization under various buffers and solvents. Solvation is just one factor that contributes to the photoisomerization reaction, and other conditions such as concentration, excitation energy, and stereochemistry of reagent molecule may also play a role in its reactivity [24-26]. Experimental studies on anthocyanins photoisomerization have focused mostly on solvation effects, which provides opportunities for further exploration of light energy and the reagent molecule on this reaction. In order for the findings of this research to be applicable to the food industry, sources of excitation that are easily acquirable and economical were chosen. Thus, the study investigated the effects of industry-accessible ultraviolet and visible energies on the extent, equilibrium, and efficiency of acylated delphinidin's reversible photoisomerization.

Materials and Methods

Materials. East Asian eggplants (*Solanum melongena* L.) were purchased from a local Chinese grocery store (Sunrise Asian Super Market, Columbus, OH, USA) and used to obtain the anthocyanin extracts. Chemical solvents used for extraction, purification, and analyses were: trifluoroacetic acid (TFA), hydrochloric acid (HCl), formic acid, acetone, chloroform, ethyl acetate (EtOAc), methanol (MeOH), potassium chloride (KCl), citric acid (CA), disodium phosphate ($Na_2HPO_4$), HPLC-grade acetonitrile, and HPLC-grade water. These chemicals were purchased from either Sigma-Aldrich, Co. (St. Louis, MO, USA) or Thermo Fisher Scientific (Waltham, MA, USA).

Anthocyanin Extraction, Purification, and Identification. Acylated anthocyanins were extracted from East Asian eggplant peels that had been frozen with liquid $N_2$, pulverized, and extracted with acidified (HCl and TFA) acetone. The plant material was phase partitioned with chloroform overnight in 4° C. and the solvents in the aqueous phase were removed by rotary evaporation (Brinkmann Büchi Rotavapor, New Castle, DE, USA). Further purification with solid phase extraction was done by loading the anthocyanins extract onto a Sep-Pak Vac 20 cc C18 cartridge (Waters Corporation, Milford, MA, USA) and washing it first with 0.01% HCl in $H_2O$, then with EtOAc, and finally with 0.01% HCl in MeOH. The acidified water and EtOAc washes were done three times, whereas the acidified MeOH rinse was performed until most of the pigments were recovered from the cartridge. A more detailed procedure is outlined by Rodriguez-Saona [27]. The resulting extract from this procedure will be termed semi-crude extract (SCE) for the rest of this description.

The anthocyanins profile of semi-crude extract was characterized by using a Nexera-i-LC 2040C 3D ultra-high performance liquid chromatography with a photo-diode array detector (UHPLC-PDA) coupled to LCMS-8040 triple quadrupole mass spectrometer with electrospray ionization (ESI-MS/MS, Shimadzu, Columbia, MD, USA). Chromatography was done with Kinetex 1.7 μm F5 column with 100 Å pore size and 100×2.1 mm dimensions (Phenomenex, Torrance, CA, USA). The photodiode array (PDA) chromatograms were collected for relative quantitation at 520 nm by % area of the two eluents.

Spectra were analyzed in order to characterize the two eluents by their retention times, fragmentation patterns, and absorbance. The solvents used for gradient-elution chromatography were 4.5% formic acid in MS-grade water for solvent A and MS-grade acetonitrile for solvent B. The UHPLC gradient started from B concentration of 1% for 1 min, 8% for 2 more min, 10% after 13 min, 25% after 2 min, then finally to 45% after 4 min. The column was flushed at 45% then equilibrated down to the starting B concentration. The LC-2040 oven was at 30° C., collision energy of −35 eV, ESI interface with nebulizer gas flow of 3 L/min, DL temperature 250° C., heat block temperature 400° C., and drying gas flow of 15 L/min. The ions were scanned under positive scan under three parameters: Q1 total scan from 100-1200 m/z, Q1 Selected Ion Monitoring (SIM) of 773, 919, and 611 m/z, and Q3 SIM 611, 465, and 303 m/z. The injection volume for the runs were 5 μL. Lab Solutions Software Ver.1 (Released 5.80) was used for data analysis and interpretation (Shimadzu, Columbia, MD, USA).

Anthocyanin Isomerization and Isolation. Semi-crude extract at a concentration of ~200 uM were placed in 30×10 mm polystyrene petri dishes at 10 mL per iteration and irradiated uncovered with UV light in a chamber (254 nm, Stratagene Stratalinker 1800 UV Crosslinker, La Jolla, CA, USA) for 15 minutes to produce delphinidin-3-cis-p-coumaroyl-rutinoside-5-glucoside (cis-Dp). The irradiated extract was then concentrated, mixed with acidified water, and passed through a 0.2 μm syringe filter for semi-preparative HPLC. The reverse phase semi-preparative HPLC system (Shimadzu, MD, USA) was LC-6AD pumps, a CBM-20A communication module, a SIL-20A HT autosampler, a CTO-20A column oven, a SPD-M20A Photodiode Array detector, and a pentafluorophenyl (PFP) column (5 μm particle size, 100 Å pore size, in a 250×21.2 mm) and ran at a flow rate of 10.0 mL/min (Phenomenex®, Torrance, CA, USA). LCMS Solution Software Version 3 (Shimadzu, Columbia, MD, USA) was used to monitor the eluting isolates. Both cis-Dp and delphinidin-3-trans-p-coumaroyl-rutinoside-5-glucoside (trans-Dp) were fractionated with acetonitrile as solvent A and 4.5% formic acid in HPLC-grade water as solvent B. The gradient for pigment isolation were as follows, with each percentage referring to solvent B—0 min: 18.5%, 2 min: 19%, 5 min: 19.5% and held until 13 min, then flushed out to 30% at 13.01 min and equilibrated to starting conditions. The purity of isolated cis- and trans-Dp was analyzed on an analytical HPLC-PDA instrument, composed of a DGU-20As degasser, LC-20AD pumps for the same two solvents used during anthocyanin identification, a SPD-M20A diode array detector, and a SIL-20AC auto sampler. The analytical column was a Kinetex EVO C18 column with 5 μm particle size, 100 Å pore size, and 150×4.6 mm in diameter and length (Phenomenex®, Torrance, CA, USA). The gradient was as follows, in which the percentages refer to the B % concentration—30 min from 10-23%, 2 min from 23-40%, flushed at 40% for 6 min, followed by equilibration to the starting B % concentration. The resulting chromatogram was used for relative quantitation at 520 nm by measurement of the retention times and % area of the two eluents. The purity was quantified by measuring the % area under the curve (AUC) of the pertinent peaks at 520 nm and 260-700 nm, after manual integration.

Monomeric Delphinidin Quantitation. The pH differential method was used to quantify monomeric anthocyanins in semi-crude extract. Using 700 nm and $\lambda_{max}$ of 540 nm under pH 1 and 4.5, the absorbance was measured by SpectraMax 190 Microplate Reader (Molecular Devices, Sunnyvale, CA, USA) and expressed as cyanidin-3-glucoside equivalents with the following equation (1) [28]:

$$\text{Monomeric } Dp(\text{mg}/\text{L}) = \frac{(Abs \times DF \times MW \times 1000)}{\varepsilon \times 1}, \tag{1}$$

in which DF=dilution factor, MW=molecular weight of cyanidin-3-glucoside (449.2 g/mol), and ε=molar absorptivity of cyanidin-3-glucoside (26,900 L/mol·cm) in pH 1 buffer.

Determination of Radiant Light Exposure Time: Preliminary Tests. In order to determine the time at which isomerization was maximized and degradation was minimized for each of the four radiant energies, 100 μM of semi-crude extract was irradiated in a sealed quartz cuvette (Science Outlet on Amazon, Seattle, WA) with a pathlength of 10 mm and a transmission spectral range of 190-1200 nm under UV chamber at 254 nm, 365 nm, and visible energies of D65 (daylight illuminant), and F2 (fluorescent light). UV chamber at 254 nm emitted 40 W of power within internal dimension of 13.7 cm (l)×18.1 cm (w)×16.8 cm (h) (UV Stratalinker 1800, Stratagene, La Jolla, CA, USA). Similarly, UV chamber at 365 nm emitted 40 W within 35 cm (l)×27 cm (w)×16 cm (h) dimensions (61 cm (l)×34 cm (w)×33 cm (h), UVP Crosslinker CL-3000L, Analytik Jena, Beverly, MA, USA). Lastly, visible light chamber (MiniMatcher MM-2e, GTI Graphic Technology Inc., Newburgh, NY, USA) equipped with both D65 (30 W) and F2 lights (15 W) were used. The time of exposure for each source of radiant energy was determined by irradiating semi-crude extract for specific lengths of time, in which the isomerization reached a plateau, signifying a chemical equilibrium. Semi-crude extract was irradiated up to 120 min with 254 nm, 180 min with 365 nm, 25 hrs with D65 lamp, and finally, 50 hrs with F2 lamp. The resulting isomerization and total delphinidin (Dp) degradation were quantified by the following equations (2, 3, 4):

$$\% \text{ cisDp isomerization} = \% \text{ final transDp} - \% \text{ initial transDp} \tag{2}$$

$$\% \text{ transDp and } \% \text{ SCE isomerization} = \% \text{ final cisDp} - \% \text{ initial cisDp} \tag{3}$$

$$\% \text{ total Dp degradation} = \% \text{ initial (cisDp+transDp)} - \text{final (cisDp+transDp)} \tag{4}$$

Isomerization by radiant energies were analyzed by analytical reverse phase HPLC, as described in the previous section Anthocyanin Isomerization and Isolation. The isomerization and degradation trends were fitted to nonparametric curves (FIG. 19-FIG. 22).

Ultraviolet-Visible Irradiation. Semi-crude extract, cis-Dp, and trans-Dp in acidified MeOH at 100 μM were sealed in quartz cuvettes and subjected to four radiant energies for their respective selected irradiation times. Environmental conditions such as temperature inside the laboratory (ranged between 21-23° C.) and placement of the light sources remained consistent, with the light bulbs above the transparent side of the cuvettes. In addition, the lid of a poly-D-lysine-coated polystyrene 96-well plate was placed under the quartz cuvettes and a white, reflective absorbent pad was used to cover the opening side of the light chamber, in order to maximize the light exposure. Immediately after isomerization for the respective times of each light source, the samples were frozen at −18° C. for up to 7 days before thawing and analyzing on the analytical HPLC-PDA.

Visible Spectrophotometry and Colorimetry. Initial absorbance spectra (from 250-800 nm) of cis- and trans-isolates in acidified MeOH were compared using a SpectraMax 190 Microplate Reader, under the cuvette setting. Then, both isolates were irradiated with UV chambers (254 nm and 365 nm) for up to 16 min and their shifts in spectra were measured at 2 min increments.

For colorimetry, cis-Dp and trans-Dp isolates (without irradiation) were placed in buffers pH 1-10 (0.025 M KCl for pH 1; CA—Na$_2$HPO$_4$ buffer solutions for pH 2-7; 0.1 M sodium bicarbonate (NaHCO$_3$) for pH 8; Na$_2$CO$_3$—NaHCO$_3$ buffer solutions for pH 9-10) and equilibrated for 15 min on a poly-D-lysine-coated polystyrene 96-well plate [28, 29]. Measurements were taken in triplicates from 250-700 nm in 5 nm intervals under SpectraMax 190 Microplate Reader for 24 hours in the dark, at 20° C. The two isomers' color characteristics were compared to the irradiated semi-crude extract (254 nm, D65, and F2) in acidic (pH 1, 2) and alkaline (pH 6-9) conditions. From pH 3-5, colors were not compared since initial screening of the two isolates' color showed very faint or translucent colors.

CIE 1976 L*a*b* color space, also known as CIELAB, is a quantitative method to characterize color coordinates. L* represents lightness, in which ±L* (white/black), ±a* (red/green), ±b* (yellow/blue), C*$_{ab}$ (chroma), and h*$_{ab}$ (hue angle). The spectral data from 380-750 nm was converted to colorimetric data using ColorBySpectra software, under 10° observer angle, D65 illuminant, and standard 1964 CIE equations.

Statistical Evaluation of Data. Under a randomized split-block design, the statistical significance of the HPLC data (area under the curves of irradiated semi-crude extract, cis-Dp and trans-Dp under 520 nm) was conducted by two-way analysis of variance ($\alpha$=0.05) and post hoc Tukey's test ($\alpha$=0.05) with SPSS Statistics software (IBM SPSS Statistics for Macintosh, Version 27.0). The technical software settings were chosen to set the two independent variables (radiant energy and chemical compound) as co-variants, for an accurate pairwise comparison.

Results and Discussion

Determination of Isolate Purity. East Asian eggplants have been previously characterized [30, 31] to have two major peaks absorbing in the 510-540 nm range, with trans-Dp making up most of the composition (~82%). Semi-crude extract's photodiode array chromatogram included 13.8% cis-Dp and 80.0% trans-Dp within a single run—with the cis-isomer eluting before the trans-isomer. To characterize these two peaks of the semi-crude extract, each of their fragmentation patterns, retention times, and absorbance spectra were compared to the literature. Then, when isolates of cis-Dp and trans-Dp were produced, the three aforementioned characteristic traits were compared for their identification. The fragmentation patterns of the two isomers were identical to each other. Specifically, 919 M$^+$ m/z was detected under Q1 Selective Ion Monitoring (SIM), signifying the intact p-coumaroyl acylated Dp. In addition, 303, 465, and 611 M$^+$ m/z were detected under MS/MS. These findings are in congruence with the literature, which states MS/MS fragmentation patterns of 757 (fully intact acylated Dp—one hexose), 611 (intact Dp—one hexose—one deoxy hexose), 465 (intact Dp—one hexose—p-coumaric acid), and 303 (delphinidin aglycone) m/z [32,33]. The absorbance spectra of the two peaks in semi-crude extract at 520 nm were compared to the respective isolates' absorbance spectra to use an additional method of characterization. Further information on cis-Dp and trans-Dp's difference in absorbance spectra will be presented in *Monitoring Photoisomerization with UV-Vis Spectroscopy*.

After semi-prep HPLC isolation, the trans-Dp isolate was 92% of the total area under curve (AUC) under max plot absorbance at 260-700 nm and 99% under absorbance at 520 nm (FIG. 11). Using the same method of quantification, cis-Dp represented 80% of the AUC at 260-700 nm and 89% at 520 nm. The impurities detected at 520 nm were the other isomer and 260-700 nm were trace amounts of phenolic acids absorbing at 290 nm and 317 nm. Around 37 min retention time, with solvent B concentration of 40%, a wide peak eluted for both trans-Dp and cis-Dp isolates that made up 9.7% and 8.9%, respectively. The same wide peak was observed in photodiode array chromatograms of trans-p-coumaric acid in acidified MeOH.

Selected Times for Radiant Light Exposure—Preliminary Tests. Radiant energies for anthocyanin excitation were chosen based on their accessibility and reproducibility. Previous work in photo-induced isomerization of acylated anthocyanins have shown the possibility of isomerization at 365 nm and sunlight levels [22, 23, 34]. Additionally, preliminary tests were done to include radiant energy of 254 nm, which is a common spectrum of light used for germicidal purposes in food safety. Photoisomerization of anthocyanins in sunlight was challenging due to the lack of controllability and reproducibility. To address this limitation, D65 illuminant was used as an analog of sunlight. Lastly, anthocyanins have applications in fruit juices and beverages, which are often exposed to fluorescent lighting in grocery stores. Ergo, F2 illuminant was used to account for the potential interaction of anthocyanins in these settings.

The time necessary for maximal isomerization with minimal degradation varied across the four radiant energies use in this study, because each of the light sources had different manufactured specifications. For this reason, semi-crude extract was used to select a specific time to be used for each of the 254 nm, 365 nm, D65, and F2 lamps. The main criteria for this selection process were based on the time that satisfies the following conditions: a) greatest amount of isomerization, b) equilibrium reached, c) extent of degradation, and d) time to achieve more isomerization with minimal degradation. Once the time exposures of the crude extracts were determined, the same time conditions were applied for photoisomerization of cis- and trans-isolates.

Irradiation at 254 nm reached its equilibrium of 37% cis-Dp: 63% trans-Dp (cis/trans ratio of 0.59) at 30 min, with degradation of 25±8.1%. Though, at 15 min, the extract had photoisomerized to produce 36% cis-Dp (cis/trans ratio of 0.56) with 4±0.9% total pigment degradation. By choosing the exposure parameter to 15 min, pigment degradation was minimized by 6.3 fold, time was saved by 50%, whilst only losing 1% in cis-production. Similarly, irradiation was conducted for up to 180 minutes under 365 nm radiant light in order to determine the time in which the isomerization plateau is observed. After 15 minutes of irradiation, 24% cis-Dp:76% trans-Dp (0.32 conversion ratio) with degradation of 4% is observed. At 30 min, semi-crude extract reached its equilibrium of 25% cis-Dp:75% trans-Dp (conversion ratio was 0.33) with degradation of 40±1%, with negligible increase in cis-production thereafter. Although equilibrium was observed at 30 min, the chosen time for 365 nm was 15 min because there was only 1% difference in accumulation of cis-Dp between 15 min and 30 min, with minimization of 10 fold in total pigment degradation. Since anthocyanins are also prone to degradation under light, general rule of thumb is to select a shorter exposure time. These preliminary tests showed that Dp also follows this rule, thereby saving time with minimal loss in production.

Irradiation with visible radiant energies required longer times to reach equilibrium than it did with UV energies. Photoisomerization with D65 lamp was conducted up to 25 hours, in which equilibrium of 49% cis-Dp:51% trans-Dp (0.96 conversion ratio) was reached at hour 6, with degradation of 37±0.5%. After the third hour of irradiation, 47% of the total pigment was cis-Dp with degradation of 1.1±0.7% and was therefore chosen as the time parameter for D65. Lastly, irradiation with F2 lamp was conducted for up to 50 hours, in which equilibrium of 52% cis-Dp: 48% trans-Dp (conversion ratio of 1.1) was reached at ~26 h, with little increase thereafter. Degradation was approximately 30%. At 20 h, cis-Dp production was at 51% (conversion ratio was 1.0) with 2.1±0.2% degradation. Similar to the determination of time for the UV chambers, since 20 h had 1% less cis-production while saving 6 hrs, hour 20 was chosen as the F2 time parameter. Determining the acceptable amount of degradation for the amount of isomerization is dependent on the application of the colorant. When isomerization leads to the production of an isomer with greater stability and tinctorial strength at specific pHs, as in the case with cis-Dp, less pigment is necessary to produce color. In which case, the consequence of total pigment photodegradation may be neutralized. If further mitigation of degradation is desired, then deoxygenation of photoreactants may be useful.

Figure 12:
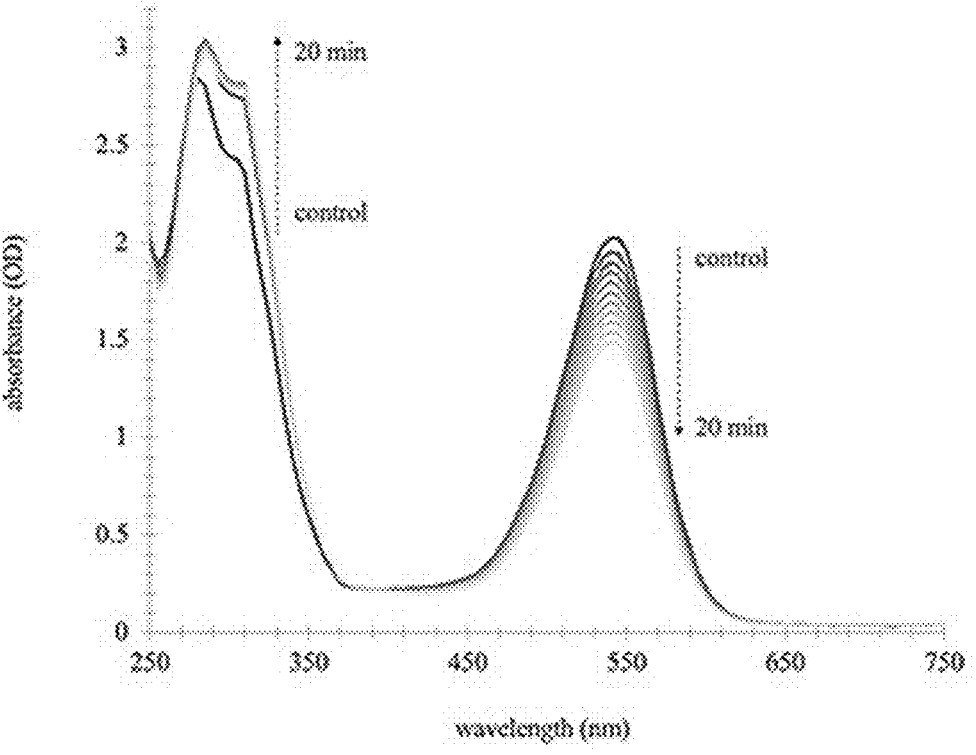
FIG. 12. Absorbance spectra of cis-Dp over time of exposure to 254 nm. Compound was dissolved in 0.01% HCl in MeOH.
Figure 13:
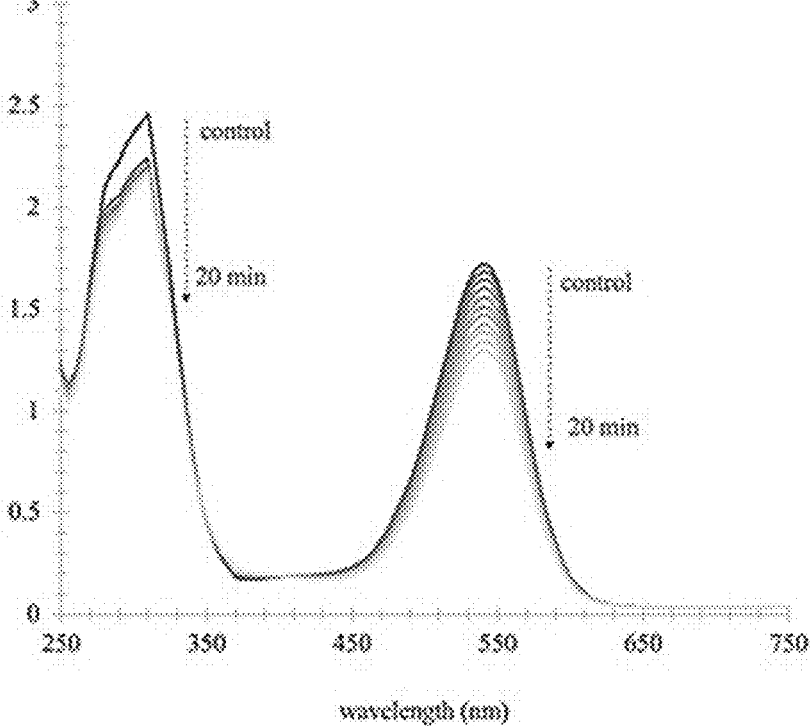
FIG. 13. Absorbance spectra of trans-Dp over time of exposure to 254 nm. Compound was dissolved in 0.01% HCl in MeOH FIG. 14. Ultraviolet-visible energies impact on isolates' and semi-crude extract (SCE)'s photoisomerization. The time of radiant energy exposure selected for each energies were kept constant. Semi-crude extract is a mixture of 86% trans-Dp and 14% cis-Dp FIG. 15. Absorbance spectra of trans-Dp under pH 1-10 with corresponding color swatch indicating the two isolate's color comparison at initial (0 h) and final (after 25 h storage for pH 1, 2 and 1 h storage for pH 3-10).

Monitoring Photoisomerization with UV-Vis Spectroscopy. The behavior of cis-Dp and trans-Dp under photoisomerization was monitored by ultraviolet-visible (UV-Vis) spectroscopy. Absorbance spectra of the two isomers differ the greatest in their curvatures at 285 nm and 310 nm (FIG. 12 and FIG. 13). While trans-Dp had greater absorbance at 310 nm than 285 nm, its cis-counterpart displayed the opposite behavior with greater absorbance at 285 nm than 310 nm. Although irradiation of both isolates under 254 nm for 20 min did not shift the curve patterns of the spectra, the presence of isomerization and degradation was observed as shifts in 285 nm and 310 nm (isomerization) and 540 nm (degradation) occurred. Thus, if the difference between $$\text{absorbance (285 nm)} - \text{absorbance (310 nm)} = \text{positive} \\ (+),$$

then the mixture is primarily made up of cis-isomer; whereas if the difference is a negative number, then the mixture is primarily made up of trans-isomer. Although specific numerical values in absorbance comparison at 285 nm or 310 nm was not enough to determine the extent of the photoisomerization reaction, this method of detecting positive or negative changes in curvature is a simple way to determine the dominant geometric isomer.

Figure 14:
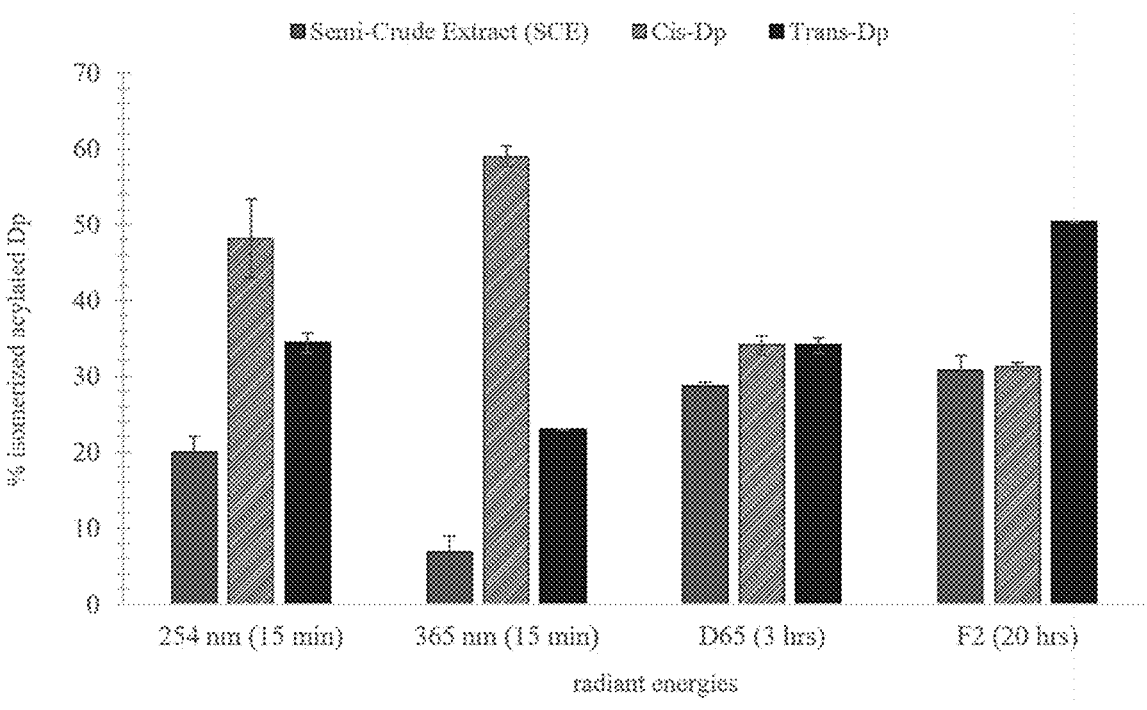

Equilibrium of Trans↔Cis and Cis↔Trans Photoisomerization. Applied radiant energies were not the only factor that affected the photoisomerization reaction of acylated Dp. Three different starting materials—semi-crude extract, cis-Dp, and trans-Dp—resulted in varying extents of isomerization when subjected to light (FIG. 14). Greatest % isomerization was observed with F2 lamp for semi-crude extract, 365 nm for cis-Dp, and F2 lamp for trans-Dp, showing that the extent of isomerization was dependent on the starting material of the irradiation. UV lamp at 254 nm induced 48±5.2% for cis-Dp, 34±1.3% for trans-Dp, and 20±2.0% isomerization for semi-crude extract. Likewise, UV lamp at 365 nm induced greatest % isomerization for cis-Dp at 59±1.7%, trans-Dp at 23±0.1%, and semi-crude extract at 7±2.0%. This may be attributed to cis-Dp absorbing more in the UV region in MeOH, the solvent of isomerization, thereby causing UV to favor cis to trans isomerization rather than trans to cis.

Starting materials' photoisomerization reactivities were different under irradiation with visible energies. Irradiation with D65 lamp yielded comparable conversion for both cis-Dp and trans-Dp at 34%, with standard deviation of 1.3% for cis-Dp and 0.9% for trans-Dp. Semi-crude extract did not isomerize as well as the isolates with 29% photoconversion ±0.5%. Irradiation with F2 was unexpectedly the most favorable for isomerizing trans-Dp at 50.3±0.1%, while both semi-crude extract and cis-Dp yielded 31% conversion with standard deviation of 2.0 for semi-crude extract and 0.6 for cis-Dp. Though these numbers may suggest that semi-crude extract's behavior under F2 irradiation was similar to cis-Dp rather than trans-Dp, the reverse is true based on some simple algebraic calculation. As described by equation (3), % isomerization of semi-crude extract was calculated by the subtraction of initial % cis-Dp. Consequently, the final % cis-Dp accumulation was ~45% AUC, comparable to semi-crude extract's 51% cis-production by F2 from Selected Times for Radiant Light Exposure—Preliminary Tests. Subtraction of ~14% initial cis-Dp from 45% is reflected as ~30% isomerization of semi-crude extract by F2 in FIG. 14.

Overall, cis-to-trans Dp photoisomerization was more efficiently induced by the following radiant energies (from most to least efficient): 365 nm>254 nm>D65≈F2. Photochemical processes are known to be wavelength-dependent [35]. As illustrated in FIG. 12 and FIG. 13, absorption of cis-Dp in 0.01% HCl in MeOH occurs the most at ~285 nm, though it also absorbs in the nearby regions—between 260-340 nm and 460-600 nm. Thus, the experimental finding that UV chamber with spectral peak at 365 nm yields the greatest amount of isomerization is in congruence with theory (details of the spectral distribution is found in FIG. 23-FIG. 26). Unlike the broad spectrum that exists for the spectral distribution of UV chamber at 365 nm, UV chamber at 254 nm emits a sharp spectral irradiance that does not overlap in the wavelengths of absorbance for cis-Dp. Furthermore, cis-p-coumaric acid absorbs at 294 nm, which is red shifted to the cis-Dp complex. This bathochromic shift also suggests the presence of intramolecular co-pigmentation [36].

On the other hand, trans-Dp to cis-Dp photoisomerization was induced in the order of: F2>D65≈254 nm>365 nm. Unlike cis-p-coumaric acid, trans-p-coumaric acid absorbs at an increased wavelength of 309 nm. Visible light's ability to induce excitation of the trans-isomer suggests that charge-transfer complexation between p-coumaric acid and delphinidin is occurring, followed by non-radiative decay of the complex. Anthocyanin-copigment complex has been understood to excite at low energies, according to theoretical molecular orbital calculations [37]. Thus, the flavylium cation excited state's absorption in wavelengths of visible light supports the order of the light sources favorable for this photoisomerization.

When the samples of irradiated semi-crude extract, cis-Dp, and trans-Dp were analyzed approximately a year later, cis-isomer was determined to be present, regardless of the radiant energy used. Though the quantification of cis-Dp's stability characteristics is not within the scope of this work, this analysis suggests that the thermal reaction back to trans-Dp is not a prominent mechanism.

A comparison between semi-crude extract and trans-Dp provides an opportunity to explore when it may be desirable to use an isolate versus an extract. The two differ approximately ~20% in their composition, with 80% of semi-crude extract comprised of the trans-isolate. Additional flavonoids and phenolics in semi-crude extract may absorb some of the emitted radiated energy, thereby lessening the total amount of energy absorbed by the chromophore. Thus, irradiation of semi-crude extract led to decrease in the extent of isomerization when compared to that of the trans-isolate. If the goal is to produce rare cis-isomers, then isolates are not required, because the semi-crude extract will still isomerize to produce the cis-isomer. However, it will not form as much cis-isomer as the isomerized trans-isomer isolate. The efficiency difference between semi-crude extract and trans-isomer are as follows, for each spectral energy: D65, 7% (greater for trans-isomer); 254 nm, 15%; 365 nm, 16%; F2, 19%. Therefore, if higher quantity of cis-Dp is desired, then it would be wise to start with a higher concentration of semi-crude extract, rather than using 100 µM. Contrastingly, if greater rate of photoconversion is desired to produce cis-isomer, then using trans-isomer isolate as the substrate would yield better results.

Figure 15:
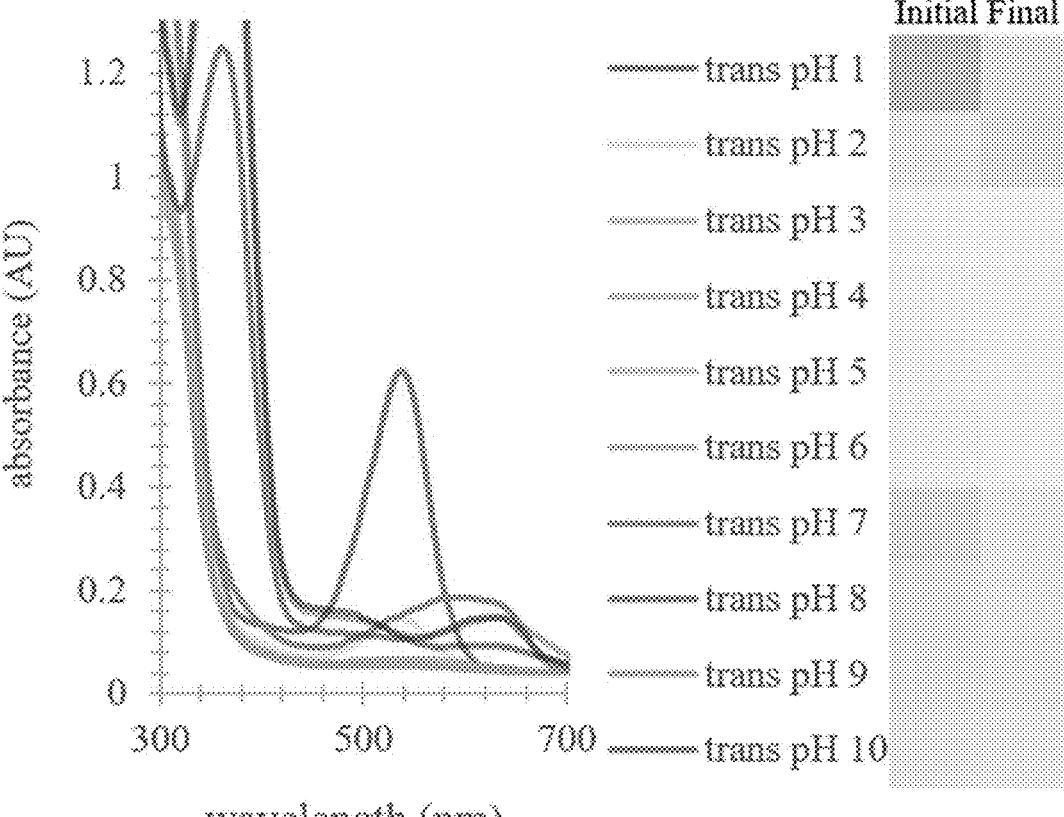
Figure 16:
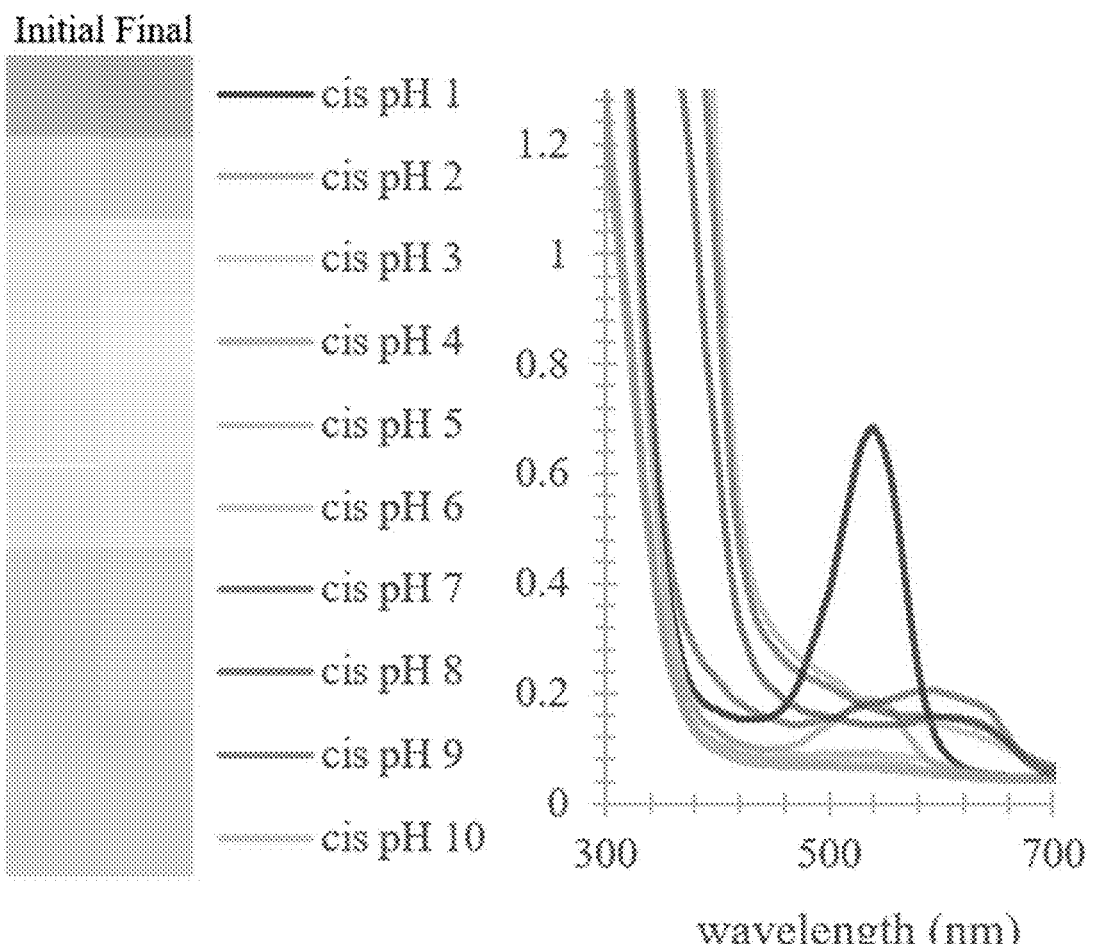
FIG. 16. Absorbance spectra of cis-Dp under pH 1-10 with corresponding color swatch indicating the two isolate's color comparison at initial (0 h) and final (after 25 h storage for pH 1, 2 and 1 h storage for pH 3-10).

Isomerized Extract Spectral Characteristics and Color Expression. Spectral absorbance of cis-Dp and trans-Dp was compared from 380-700 nm for pH 1-10. In highly acidic pH of 1-2, the patterns of absorbance across the wavelengths were comparable between the two isomers, but cis-Dp absorbed slightly greater than trans-Dp for both pHs (FIG. 15 and FIG. 16). In pH 3-5, both isomers did not absorb, which is supported by the colorless color swatch. The greatest difference between the two isomers occurred at pH 8, which is supported by their varying curvature around 380-430 nm (FIG. 15 and FIG. 16). In between the aforementioned range of wavelength, trans-Dp depicts a clear peak around 370 nm, whereas its cis-counterpart behaves closer to a peak around 360 nm, signifying a slight hypsochromic shift. The hypsochromic shift from trans-Dp to cis-Dp is in congruence with the bluer tone of trans-Dp under visual analysis.

On a previously reported study on cis- and trans-acylated Dp's color performance, the cis-isomer was shown to have greater half-life than the trans-isomer in pH 1 [38]. This finding is consistent with the noticeable color vibrance of cis-Dp in comparison to trans-Dp, after 25 hrs of storage under 20° C. in the dark, especially in the acidic pH range (FIG. 15 and FIG. 16). The aforementioned study also reported shorter color half-life for cis-Dp at alkaline pH in comparison to its trans-counterpart. In this study, the cis-isomer in alkaline pH retained its saturation for longer than trans-Dp, as depicted by the color swatch (FIG. 15 and FIG. 16). The findings could be attributed to the faint starting color at time 0 of the cis-isomer.

Irradiation of semi-crude extract under 254 nm, D65, and F2 lamp for their selected times resulted in comparable color characteristics to each other, regardless of the source of the radiant energy. Since the final equilibrium of trans-Dp-to-cis-Dp in irradiated semi-crude extract was known to be different for each of the radiant energy, their difference in final color characteristics were expected. As indicated in Selected Times for Radiant Light Exposure—Preliminary Tests, irradiation with 254 nm yielded 36% isomerization and irradiation with F2 lamp yielded the greatest conversion among the radiant energies at 51%. Despite their difference in isomer composition post-irradiation, their similar color characteristics suggest ~15% difference in isomer composition does not affect color characteristics. It is possible that a greater difference in chemical equilibrium, such as 60% cis-Dp vs 30% cis-Dp, may show a difference in color. Further studies on the relationship between isomer composition and color characteristics will need to be conducted for definitive conclusions.

Figure 17:
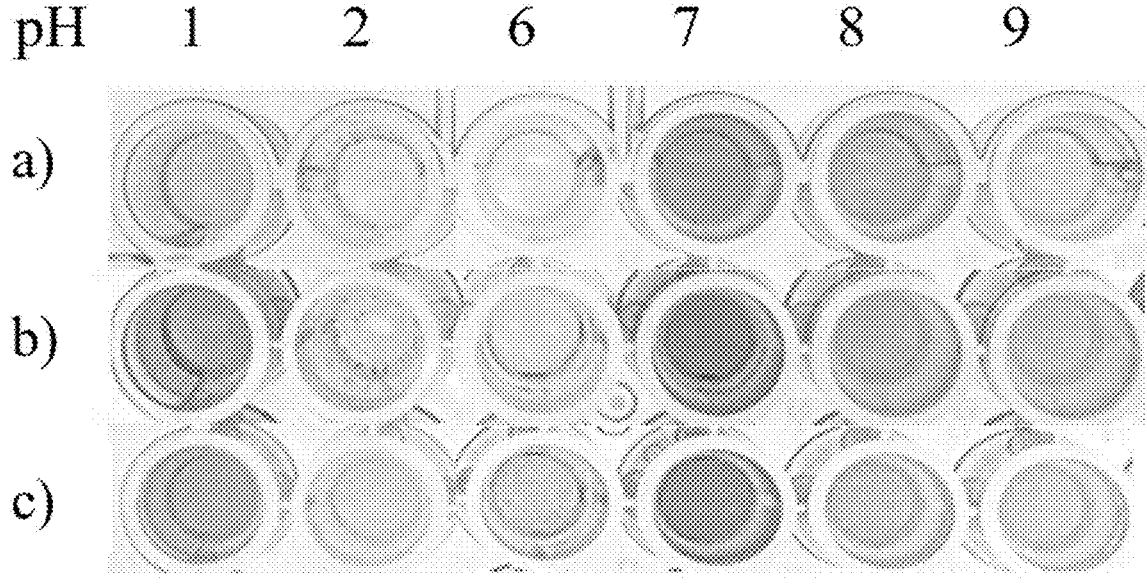
FIG. 17. Comparison between a) trans-Dp isolate (top row), b) cis-Dp isolate (middle row), and c) semi-crude extract (bottom row) irradiated with 254 nm for 15 min at t=0 (15 minutes after equilibration in pH buffers) before storage.

Irradiated semi-crude extract's colorimetric data were compared to both cis-Dp and trans-Dp isolate's in acidic pH and alkaline pH, but not from pH 3 to pH 5, since both isomers bleached in this region (FIG. 15 and FIG. 16). In acidic pH, irradiated semi-crude extract exhibited similar color expression to the trans-Dp isolate. Quantitative comparison showed that $\Delta E_{SCE\text{-}trans}$ was around 5, whereas $\Delta E_{SCE\text{-}cis}$ was closer to 10. Upon qualitative analysis, irradiated semi-crude extract resembled similar hue of trans-Dp in pH 1 and 2, but with the color intensity of cis-Dp (FIG. 17). This discrepancy could be due to the fact that the concentration of irradiated semi-crude extract was 100 µm whereas the isolates were 90 µm, which would affect $c^*_{ab}$ and $L^*$. $H^*_{ab}$ values would be unaffected by slight concentration differences, and upon its comparison, irradiated semi-crude extract was more similar to cis-Dp isolate in acidic pH. However, cis- and trans-isomers only differed by 1° in hue angle, so this observation may not be detected by consumers or untrained human eyes.

In pH 6 to pH 9, irradiated semi-crude extract resembled color expression of cis-Dp, as indicated by smaller $\Delta E_{SCE\text{-}cis}$ rather than $\Delta E_{SCE\text{-}trans}$ (Table 7). This quantitative analysis is supported by FIG. 17, which shows irradiated semi-crude extract's greater chromaticity in pH 6 and green hue in pH 8—much like the cis-Dp isolate. The color expression of irradiated semi-crude extract was expected to be like the dominant isomer, or trans-Dp for many of the radiant energies. However, its resemblance to cis-Dp suggests the that in alkaline conditions where anthocyanins are often unstable, cis-Dp was able to persevere—potentially due to an increase in intramolecular co-pigmentation effect as a result of the cis-hydroxycinnamic acid conformation [14].

TABLE 7

Colorimetric analysis of semi-crude extract (SCE) after irradiation with 254 nm, D65, and F2. CIELAB values were acquired immediately after equilibration and after 24 hours of storage in the dark at 20° C. Δ E was calculated for difference between irradiated semi-crude extract and cis-Dp isolate. L*: lightness; a*: red (+) to green (−); b*: yellow (+) to blue (−); $c^*_{ab}$: chroma; $h^*_{ab}$: hue angle.

| | | pH 1 | pH 2 | pH 6 | pH 7 | pH 8 | pH 9 |
|---|---|---|---|---|---|---|---|
| 0 h | L* | 76.5 | 87.8 | 87.5 | 79.5 | 85.6 | 86.2 |
| | | (±1.3) | (±1.1) | (±0.9) | (±1.0) | (±0.3) | (±0.8) |
| | a* | 37.1 | 12.5 | 3.5 | −1.1 | −1.7 | 0.02 |
| | | (±2.8) | (±2.1) | (±0.3) | (±0.08) | (±0.1) | (±0.3) |
| | b* | −11.9 | −0.3 | 2.2 | −5.7 | 16.0 | 20.9 |
| | | (±1.1) | (±0.8) | (±0.3) | (±1.1) | (±0.4) | (±1.1) |
| | $c^*_{ab}$ | 39.0 | 12.9 | 4.1 | 5.8 | 16.1 | 20.9 |
| | | (±2.9) | (±1.7) | (±0.4) | (±1.1) | (±0.4) | (±1.1) |
| | $h^*_{ab}$ | 342.4 | 184.7 | 32.4 | 258.7 | 96.2 | 90.0 |
| | | (±0.5) | (±6.3) | (±5.1) | (±0.9) | (±1.1) | (±0.9) |
| | Δ $E_{SCE-cis}$ | 9.5 | 7.6 | 5.2 | 8.8 | 10.8 | 5.6 |
| | Δ $E_{SCE-trans}$ | 5.5 | 5.8 | 7.0 | 9.5 | 17.2 | 17.6 |

TABLE 7-continued

Colorimetric analysis of semi-crude extract (SCE) after irradiation with 254 nm, D65, and F2. CIELAB values were acquired immediately after equilibration and after 24 hours of storage in the dark at 20° C. Δ E was calculated for difference between irradiated semi-crude extract and cis-Dp isolate. L*: lightness; a*: red (+) to green (−); b*: yellow (+) to blue (−); $c^*_{ab}$: chroma; $h^*_{ab}$: hue angle.

|  |  | pH 1 | pH 2 | pH 6 | pH 7 | pH 8 | pH 9 |
|---|---|---|---|---|---|---|---|
| 24 h | L* | 79.7 | 86.2 | 91.3 | 90.0 | 89.7 | 90.7 |
|  |  | (±1.1) | (±1.1) | (±1.2) | (±0.3) | (±0.2) | (±0.2) |
|  | a* | 31.3 | 16.3 | 0.1 | −0.2 | −0.9 | −1.4 |
|  |  | (±2.2) | (±2.3) | (±0.2) | (±0.1) | (±0.1) | (±0.04) |
|  | b* | −7.9 | −1.5 | 8.7 | 12.9 | 20.3 | 20.0 |
|  |  | (±0.9) | (±0.5) | (±0.07) | (±0.4) | (±0.7) | (±1.1) |
|  | $c^*_{ab}$ | 32.2 | 16.4 | 8.7 | 12.9 | 20.3 | 20.0 |
|  |  | (±2.3) | (±2.3) | (±0.08) | (±0.4) | (±0.7) | (±1.1) |
|  | $h^*_{ab}$ | 345.9 | 354.8 | 89.4 | 91.0 | 92.5 | 94.1 |
|  |  | (±0.6) | (±1.1) | (±1.6) | (±0.4) | (±0.5) | (±0.4) |
|  | Δ $E_{SCE-cis}$ | 36.2 | 21.2 | 7.0 | 1.1 | 6.0 | 7.5 |
|  | Δ $E_{SCE-trans}$ | 7.3 | 16.0 | 11.2 | 10.5 | 3.9 | 4.3 |

Figure 18:
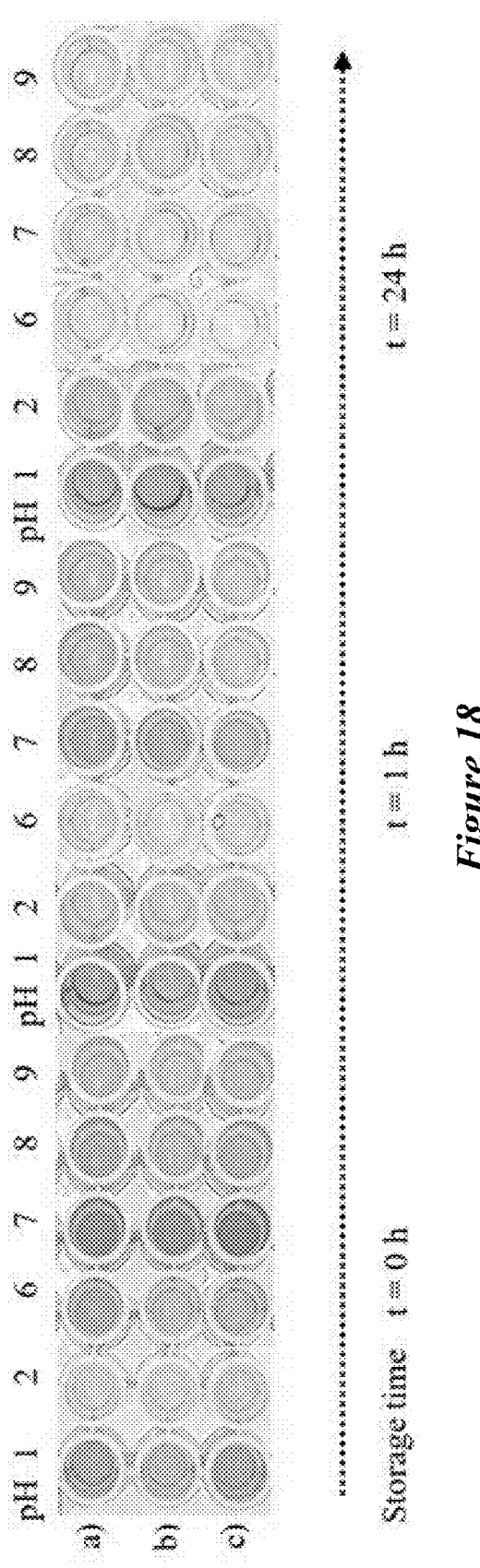
FIG. 18. Color characteristics of semi-crude extract irradiated with a) 254 nm for 15 min (top row) (cis-Dp: 36% and trans-Dp: 64%) b) F2 lamp for 20 hrs (middle row) (cis-Dp: 51% and trans-Dp: 49%), and c) D65 for 3 hrs (bottom row) (cis-Dp: 47% and trans-Dp: 53%). Isomerized samples were expressed in the pHs with the greatest difference from comparison of the cis-Dp and trans-Dp—pH 1, 2, 6, 7, 8, and 9
Figure 19:
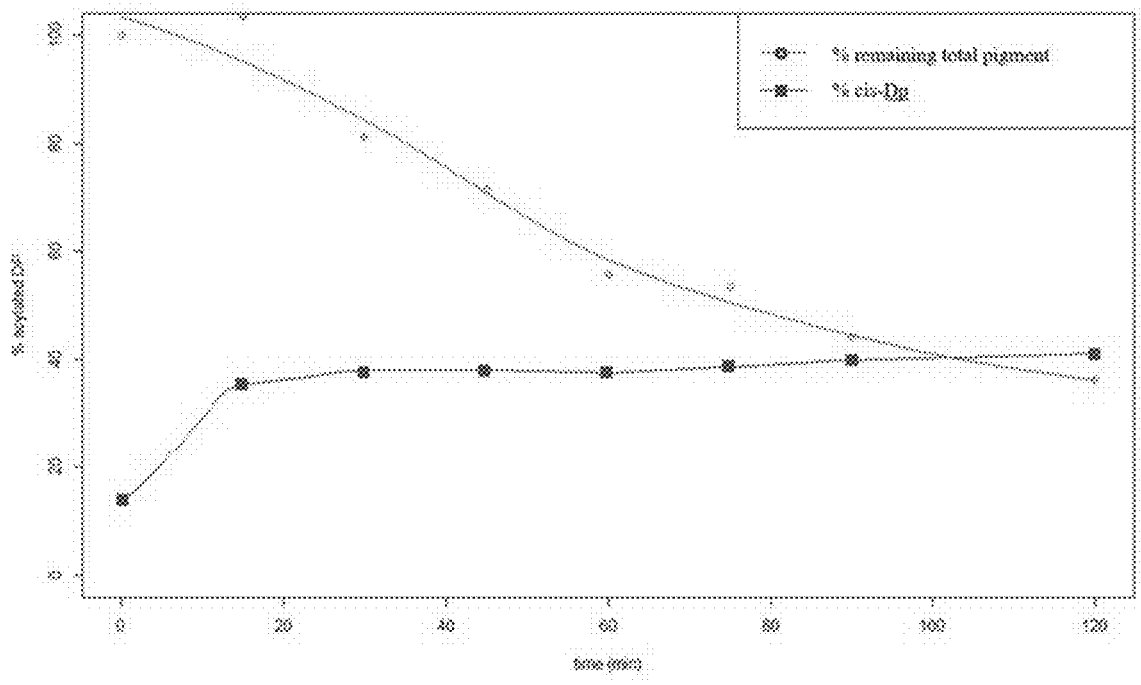
FIG. 19. Equilibrium of semi-crude extract isomerization under 254 nm.
Figure 20:
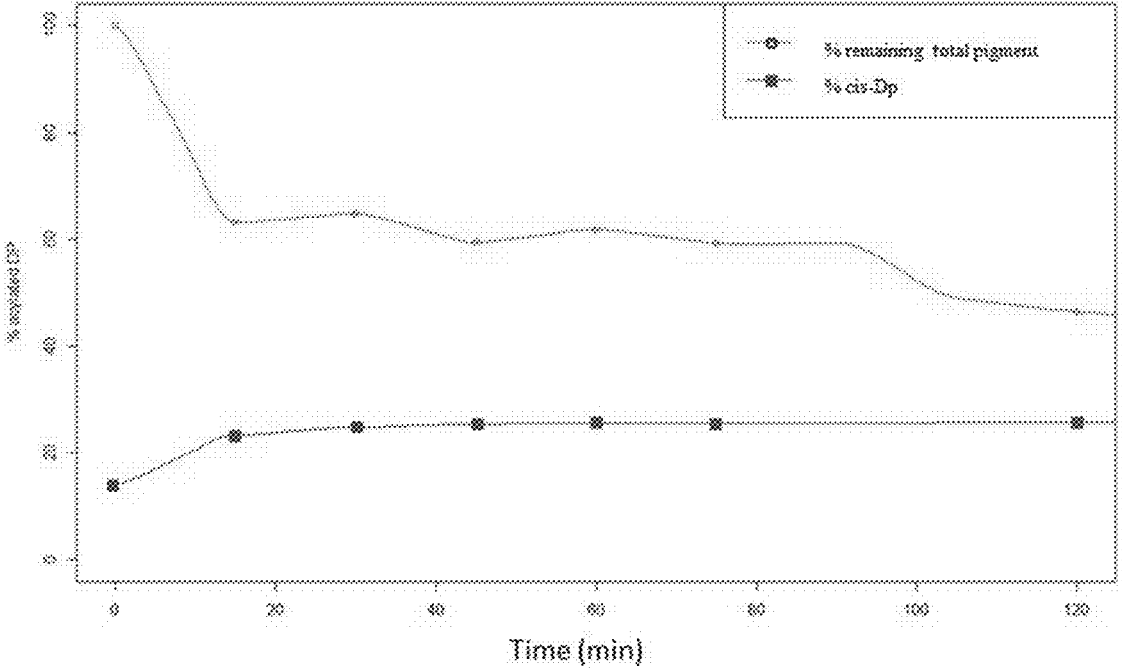
FIG. 20. Equilibrium of semi-crude extract isomerization under 365 nm
Figure 21:
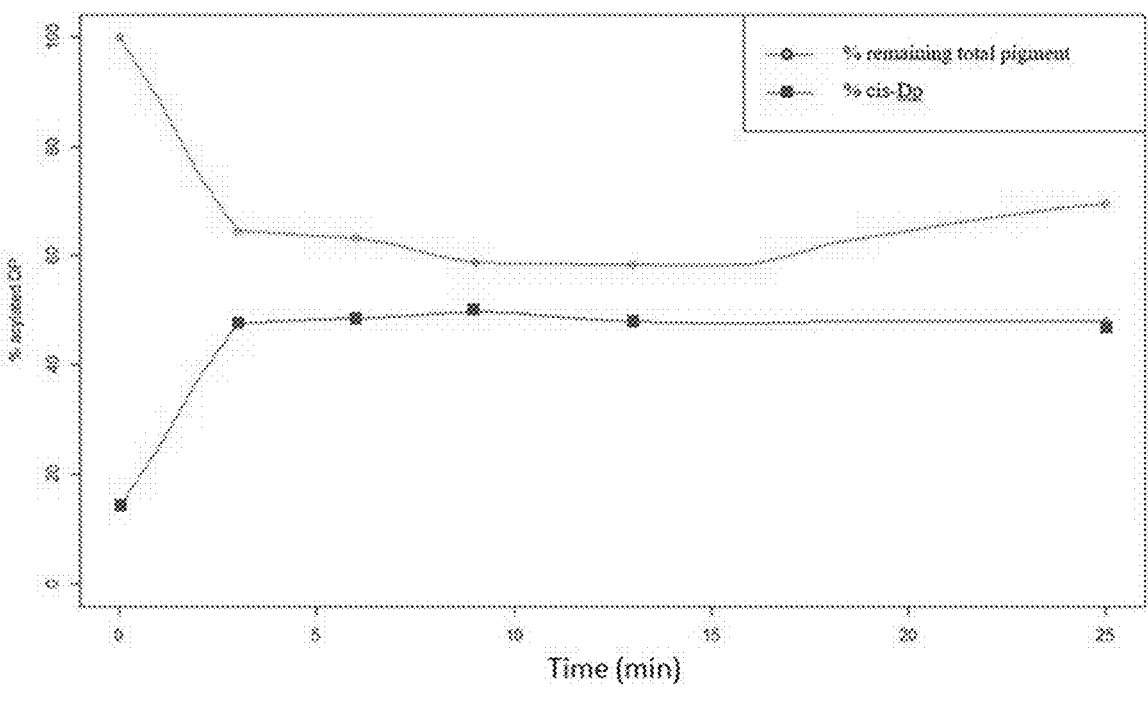
FIG. 21. Equilibrium of semi-crude extract isomerization under D65
Figure 22:
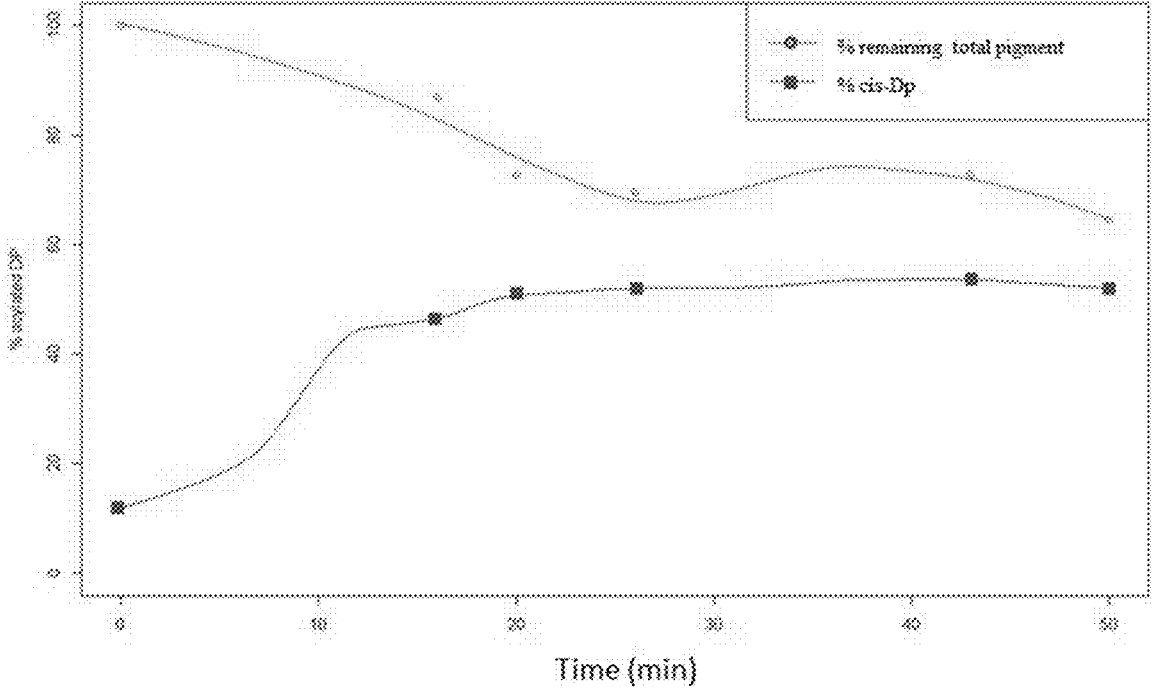
FIG. 22: Equilibrium of semi-crude extract isomerization under F2.
Figure 23:
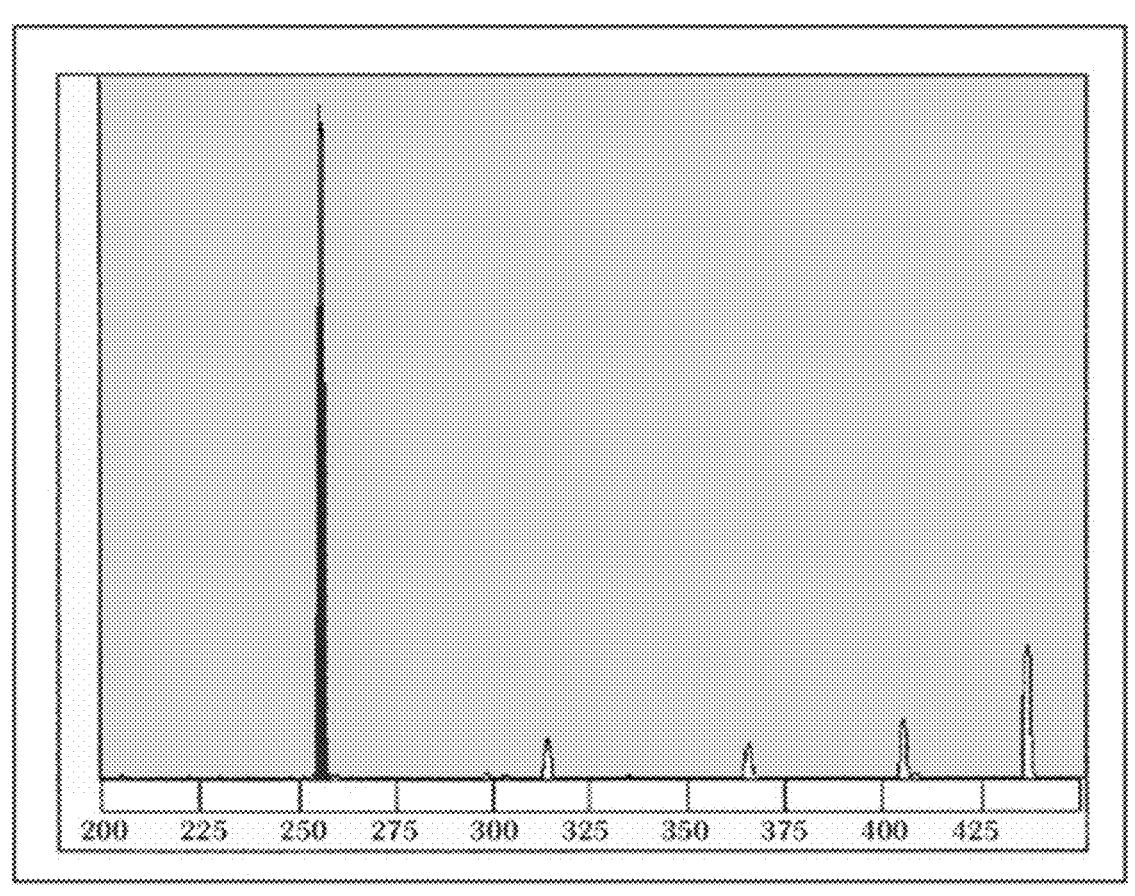
FIG. 23. Spectral distribution of the 254 nm radiant energy.
Figure 24:
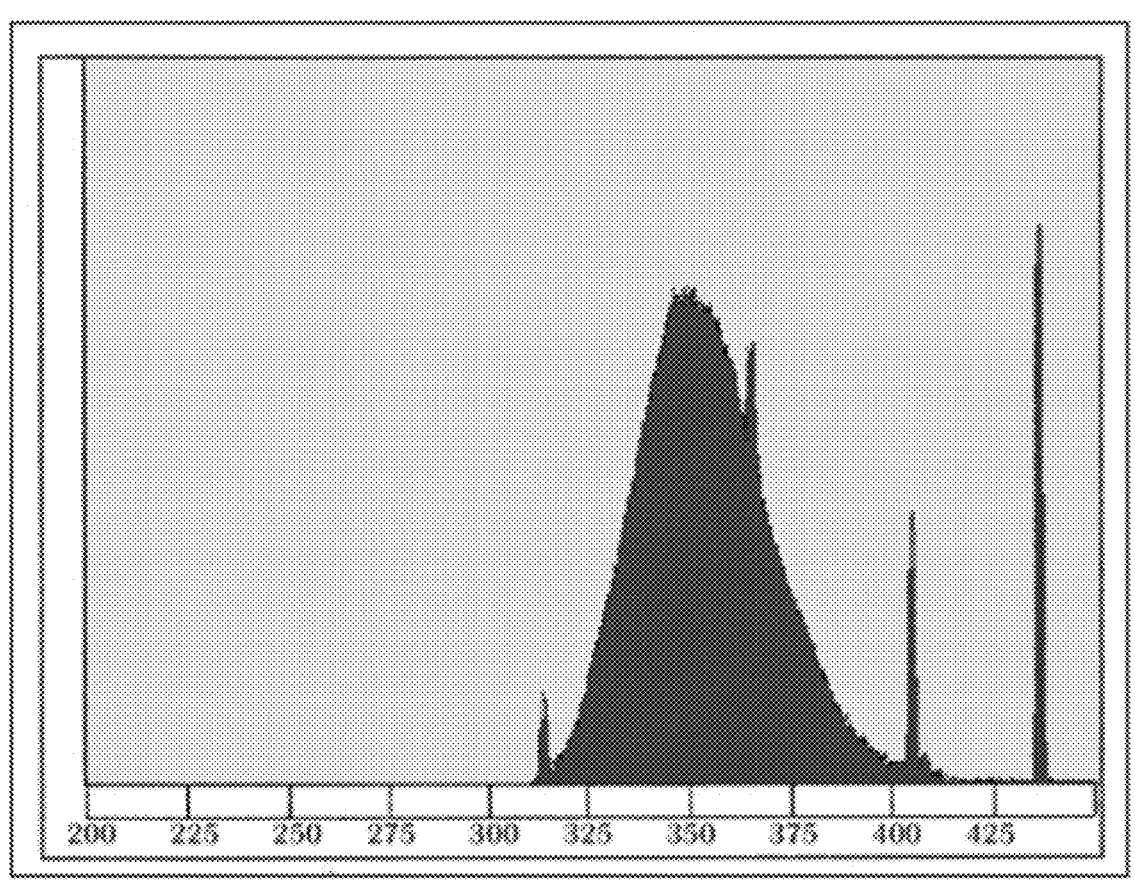
FIG. 24. Spectral distribution of the 365 nm radiant energy.
Figure 25:
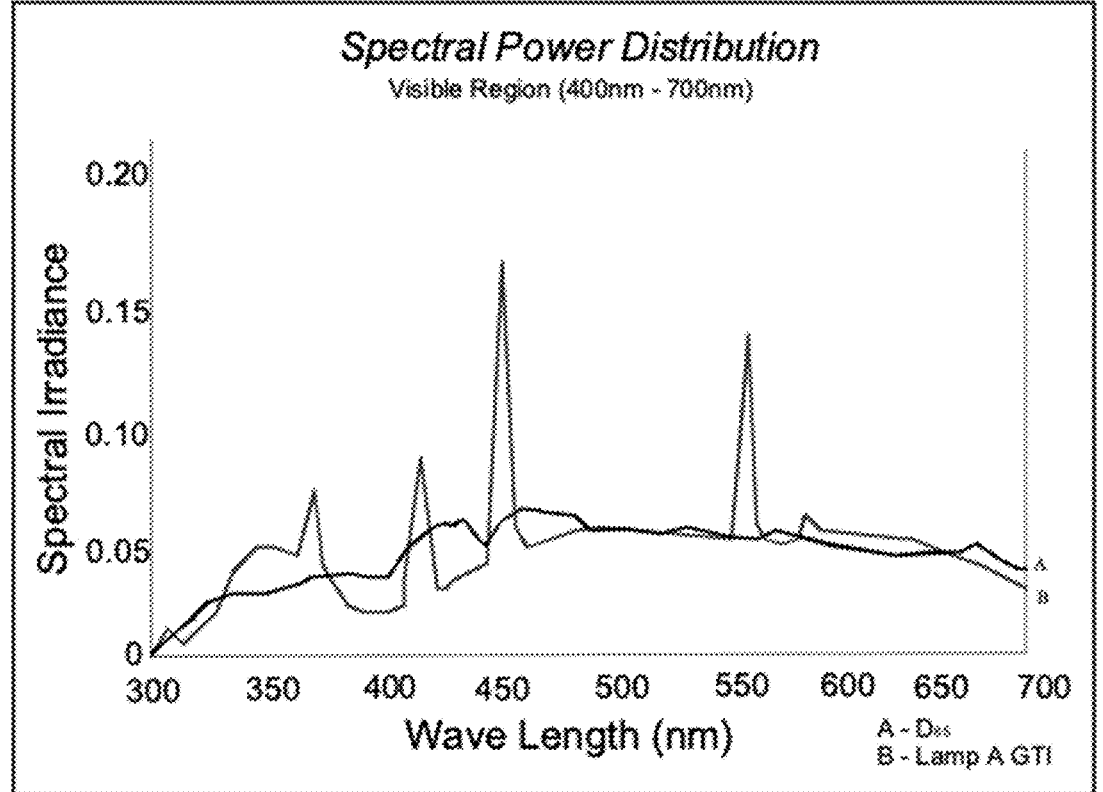
FIG. 25. Spectral distribution of the D65 radiant energy.
Figure 26:
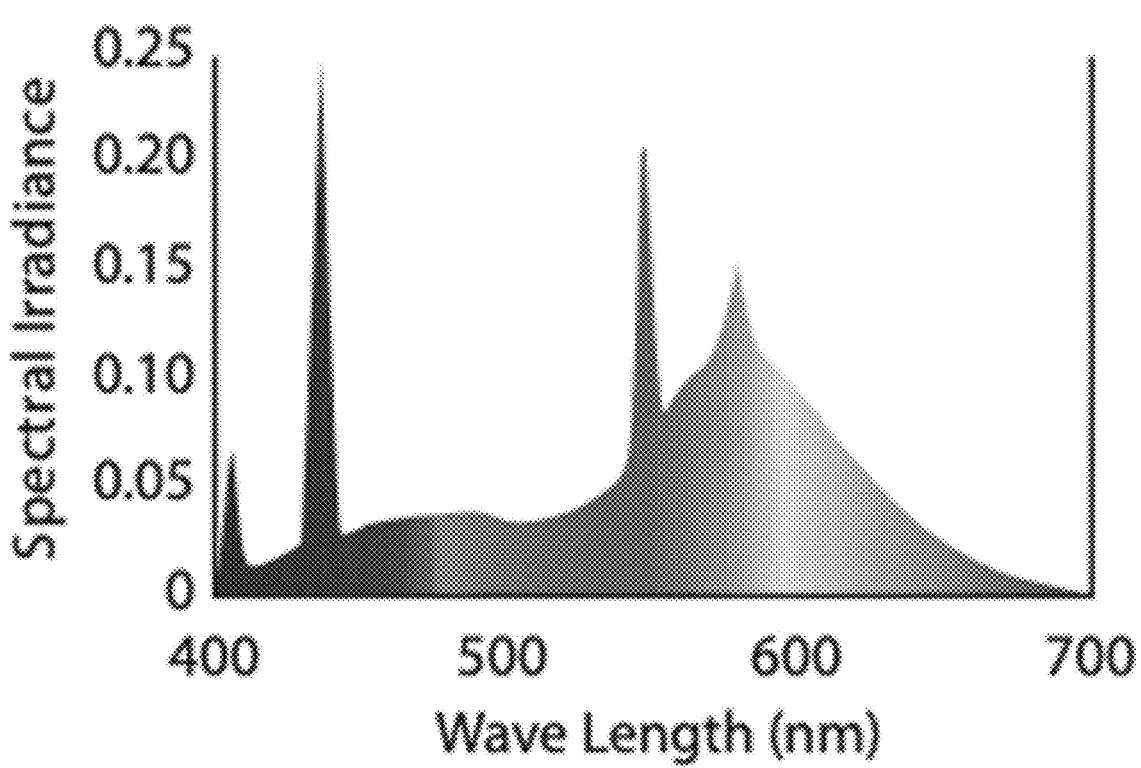
FIG. 26. Spectral distribution of the F2 radiant energy. CIE standard illuminant F2: wide band fluorescent lamp with high amounts of green and very little red energy. similar spectral power distribution to TL8.

Isomerized Extract Color Stability. Color stability of irradiated semi-crude extract was measured for up to 24 hours by storage in the dark at 20° C. (FIG. 18). According to the colorimetric values in Table 7, the $c^*_{ab}$ value of irradiated semi-crude extract at pH 1 decreased by 6.8 after storage, and still retained much of its color. This is comparable the behavior of cis-Dp at pH 1 after 25 hours of storage, which decreased in its $c^*_{ab}$ value by 2.1, rather than the trans-isomer, which decreased in saturation by 24.4 after storage. Although the irradiated semi-crude extract did not retain its green-blue hue in alkaline pH, its $c^*_{ab}$ increased after 24 hours of storage, just as cis-Dp—though, this increase in chromaticity is most likely due to browning. Comparison of the color between irradiated semi-crude extract in pH 1 (FIG. 18) to the color swatch of trans-Dp and cis-Dp after 25 hours of storage (FIG. 15 and FIG. 16) shows that the color intensity of the irradiated mixture remained vibrant like the cis-isomer in acidic pH. This allows for the opportunity to achieve favorable color performance using extracts with mixed composition of isomers, without the labor and resource-intensive method of acquiring pigment isolates.

Conclusions. Ultraviolet-visible energies induced photochromism of acylated Dp, though at varying yields and efficiencies depending on the starting material. Since specific laser wavelengths are often difficult to acquire and expensive, industry-accessible energies sources were used in this study. Excitation of trans-chromophore with visible radiant energy yielded whereas ultraviolet energies produced more isomerization of the cis-chromophore. Reactivity of the mixture of trans- and cis-acylated Dp were distinct from irradiation of isolates when the applied energies were ultraviolet. The resulting color differences between the two isomer pigments were the greatest in pH 1 and alkaline pH, though their stability varied the most in pH 1. The color performance of irradiated extracts were similar, regardless of the wavelengths of the applied energy. Their color characteristics in both the acidic and alkaline pHs were comparable to that of cis-isolates, including at pH 1, in which the irradiated extract were deemed as stable as the cis-isolate. This study gives insight to the photochromic properties of acylated Dp, as it absorbs ultraviolet-visible light. Production of rare cis-acylated Dp with easily acquirable light sources can aid in providing a greater color palette for the food industry.

Abbreviations Used. ACN: anthocyanins; Dp: delphinidins; Cis-Dp: delphinidin-3-cis-p-coumaroyl-rutinoside-5-glucoside; Trans-Dp: delphinidin-3-trans-p-coumaroyl-rutinoside-5-glucoside; SCE: semi-crude extract; UHPLC: ultra high pressure liquid chromatography; MS: mass spectrometry; MS/MS: tandem mass spectrometry; ESI: electrospray ionization; SIM: selected ion monitoring; UV: ultraviolet; Vis: visible; AUC: area under the curve; $C^*_{ab}$: chroma; $h^*_{ab}$: hue angle; DF: dilution factor; MW: molecular weight; ε: molar absorptivity; Abs: absorbance.

REFERENCES (1) He J et al. Anthocyanins: Natural Colorants with Health-Promoting Properties. Annu. Rev. Food. 2010, 1, 163-187.
(2) Konczak I et al. Anthocyanins—More Than Nature's Colours. J Biomed. Biotechnol. 2004, 5, 239-240.
(3) Wallace T C et al. Anthocyanins. Adv. Nutr. 2015, 6(5), 620-622.
(4) Cortez R et al. Natural Pigments: Stabilization Methods of Anthocyanins for Food Applications. Compr. Rev. Food Sci. Food Saf. 2017, 16(1), 180-198.
(5) Boulton R. The Copigmentation of Anthocyanins and Its Role in the Color of Red Wine: A Critical Review. Am. J. Enol. Vitic. 2001, 52(2), 67-87.
(6) Selig M J et al. High Pressure Processing of Beet Extract Complexed with Anionic Polysaccharides Enhances Red Color Thermal Stability at Low PH. Food Hydrocoll. 2018, 80, 292-297.
(7) Carocho M et al. Adding Molecules to Food, Pros and Cons: A Review on Synthetic and Natural Food Additives. Compr. Rev. Food Sci. Food Saf. 2014, 13(4), 377-399.
(8) Sigurdson G T et al. Natural Colorants: Food Colorants from Natural Sources. Annu. Rev. Food Sci. Technol. 2017, 8(1), 261-280.
(9) Malien-Aubert C et al. Color Stability of Commercial Anthocyanin-Based Extracts in Relation to the Phenolic Composition. Protective Effects by Intra- and Intermolecular Copigmentation. J. Agric. Food Chem. 2001, 49(1), 170-176.
(10) Giusti M M et al. Acylated Anthocyanins from Edible Sources and Their Applications in Food Systems. Biochem. Eng. J. 2003. 14(3), 217-225.
(11) Sigurdson G T et al. Molar Absorptivities (c) and Spectral and Colorimetric Characteristics of Purple Sweet Potato Anthocyanins. Food Chem. 2019, 271, 497-504.

(12) Turner L B et al. Light Induced Isomerization and Dimerization of Cinnamic Acid Derivatives in Cell Walls. Phytochem. 1993. 33(4), 791-796.

(13) Sigurdson G T et al. Cis-Trans Configuration of Coumaric Acid Acylation Affects the Spectral and Colorimetric Properties of Anthocyanins. Molecules 2018, 23(3), 598.

(14) George F et al. Influence of trans-cis isomerisation of coumaric acid substituents on colour variance and stabilisation in anthocyanins. Phytochem. 2001, 57, 791-795

(15) Trouillas P et al. Stabilizing and Modulating Color by Copigmentation: Insights from Theory and Experiment. Chem. Rev. 2016, 116(9), 4937-4982.

(16) Silva V O et al. Chemistry and Photochemistry of Natural Plant Pigments: The Anthocyanins. J. Phys. Org. Chem. 2016, 29(11), 594-599.

(17) Gavara R et al. 4'-Carboxy-7-Hydroxyflavylium. A Multistate System Involving Twelve Species Reversibly Interconverted by pH and Light Stimuli. J. Phys. Chem. A 2014, 118(26), 4723-4731.

(18) Leydet Y et al. Impact of Water on the Cis-Trans Photoisomerization of Hydroxychalcones. J. Phys. Chem. A 2013, 117(20), 4167-4173.

(19) Gago S et al. Flavylium Based Dual Photochromism: Addressing Cis-Trans Isomerization and Ring Opening-Closure by Different Light Inputs. Chem. Commun. 2015, 51(34), 7349-7351.

(20) Pina F et al. Chemistry and Applications of Flavylium Compounds: A Handful of Colours. Chem. Soc. Rev 2012, 41, 869-908.

(21) Basilio N et al. Chemistry and Photochemistry of Anthocyanins and Related Compounds: A Thermodynamic and Kinetic Approach. Molecules. 2016, 21, 1502.

(22) Mazza G et al. The Mechanism of Co-Pigmentation of Anthocyanins in Aqueous Solutions. Phytochem. 1990, 29(4), 1097-1102.

(23) Brouillard R et al. The Hemiacetal-Cis-Chalcone Equilibrium of Malvin, a Natural Anthocyanin. Can. J. Chem. 1990, 68, 755-761.

(24) Yoshida K et al. Structure of Anthocyanins Isolated from Purple Leaves of Perilla Ocimoides L. Var. Crispa Benth and Their Isomerization by Irradiation of Light. Agric. Biol. Chem. 1990, 54(7), 1745-1751.

(25) Hayashi K et al. Photo-Isomerization of the Nasunin, the Ma Jor Eggplant Anthocyanins. Food Sci. Technol. Int Tokyo 1998, 4(1), 25-28.

(26) Lin Y J et al. Effect of experimental factors on nitrobenzaldehyde photoisomerization. Chemosphere. 2002, 48, 1-8.

(27) Sakata K et al. Ab initio study of molecular structures and excited states in anthocyanins. Tetrahedron. 2006, 62, 3721-3731.

(28) Lui B F et al. Unusual concentration dependence of the photoisomerization reaction in donor-acceptor Stenhouse adducts. Photochem. Photobiol. Sci. 2019, 18, 1587-1595.

(29) Rodriguez-Saona L E et al. Current Protocols in Food Analytical Chemistry; John Wiley & Sons, Inc., 2001; p F1.1.1-F1.1.11.

(30) Giusti M M et al. Characterization and Measurement of Anthocyanins by UV-Visible Spectroscopy. In Handbook of Food Analytical Chemistry; 2001; Vol. 2-2, pp 19-31.

(31) Zhou Y et al. Accumulation of Anthocyanins and Other Phytochemicals in American Elderberry Cultivars during Fruit Ripening and its Impact on Color Expression. Plants. 2020, 9, 1721.

(32) Sigurdson G T et al. Bathochromic and Hyperchromic Effects of Aluminum Salt Complexation by Anthocyanins from Edible Sources for Blue Color Development. J. Agric. Food Chem. 2014, 62(29), 6955-6965.

(33) Ichiyanagi T et al. Nasunin from Eggplant Consists of Cis-Trans Isomers of Delphinidin 3-[4-(p-Coumaroyl)-L-rhamnosyl (1→6)glucopyranoside]]-5-glucopyranoside. J. Agric. Food Chem. 2005, 53, 9472-9477.

(34) Zheng J et al. Anthocyanins composition and antioxidant activity of wild Lycium ruthenicum Murr. from Qinghai-Tibet Plateau. Food Chem. 2010, 126(3), 859-865.

(35) Protti S et al. Wavelength dependence and wavelength selectivity in photochemical reactions. Photochem. Photobiol. Sci., 2019, 18, 2094.

(36) Sadilova E et al. Anthocyanins, Colour and Antioxidant Properties of Eggplant (Solanum melongena L.) and Violet Pepper (Capsicum annuum L.) Peel Extracts. Z Naturforsch C J Biosci. 2006, 61(7-8), 527-35.

(37) Yoshida K et al. Influence of E,Z-Isomerization and Stability of Acylated Anthocyanins under the UV Irradiation. In Biochem. Eng. J. 2003, 14, 163-169.

(38) Eiro M J et al. Anthocyanin Color Behavior and Stability during Storage: Effect of Intermolecular Copigmentation. J. Agric. Food Chem. 2002, 50(25), 7461-7466

Example 4—Effect of Light Energy on Photoisomerization of Acylated Anthocyanins for the Expansion of Their Color Expression Color is an identifying characteristic of food products (Sigurdson et al. Annu Rev Food Sci Technol, 2017, 8, 261-280). In recent years, consumers have been demanding more colorants derived from plant materials, such as fruits and vegetables (Ahmadiani et al. Food Chem. 2016, 197, 900-906). Therefore, research efforts on anthocyanins (ACN) have increased (Bakowska-Barczak. J. Food Nutr. Sci. 2005, 14, 107-116).

Applying light treatment to acylated anthocyanins can modulate its color expression, without external addition of stabilizing compounds. Specifically, photoisomerization of anthocyanins acylating group from trans- to cis-configuration leads to an expansion of their color expression.

The impact of different light sources on the production of anthocyanin pigments with enhanced performance was investigated.

Anthocyanins were extracted from eggplants using acetone:chloroform (1:2). Solid phase extraction was used for semi-purification of the samples. Samples were prepared in quartz cuvettes and irradiated with sunlight, in a light box, or in a UV chamber at 365 nm.

Figure 27:
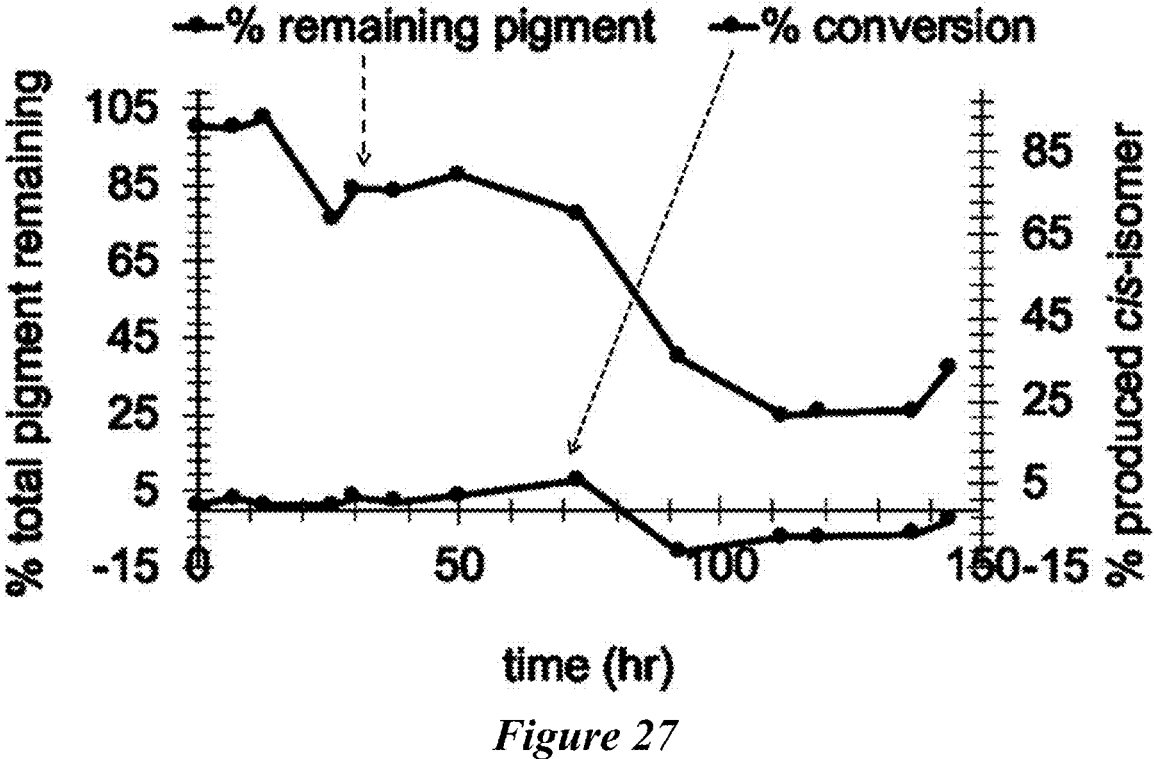
FIG. 27. Remaining pigment and % conversion from trans to cis when acylated delphinidin was exposed to the sunlight. The % total pigment degradation was much greater than the % photoconversion.

The greatest conversion from trans to cis was observed after 73 hours when acylated delphinidin was exposed to the sunlight (FIG. 27). The % total pigment degradation was much greater than the % photoconversion (FIG. 27).

Figure 28:
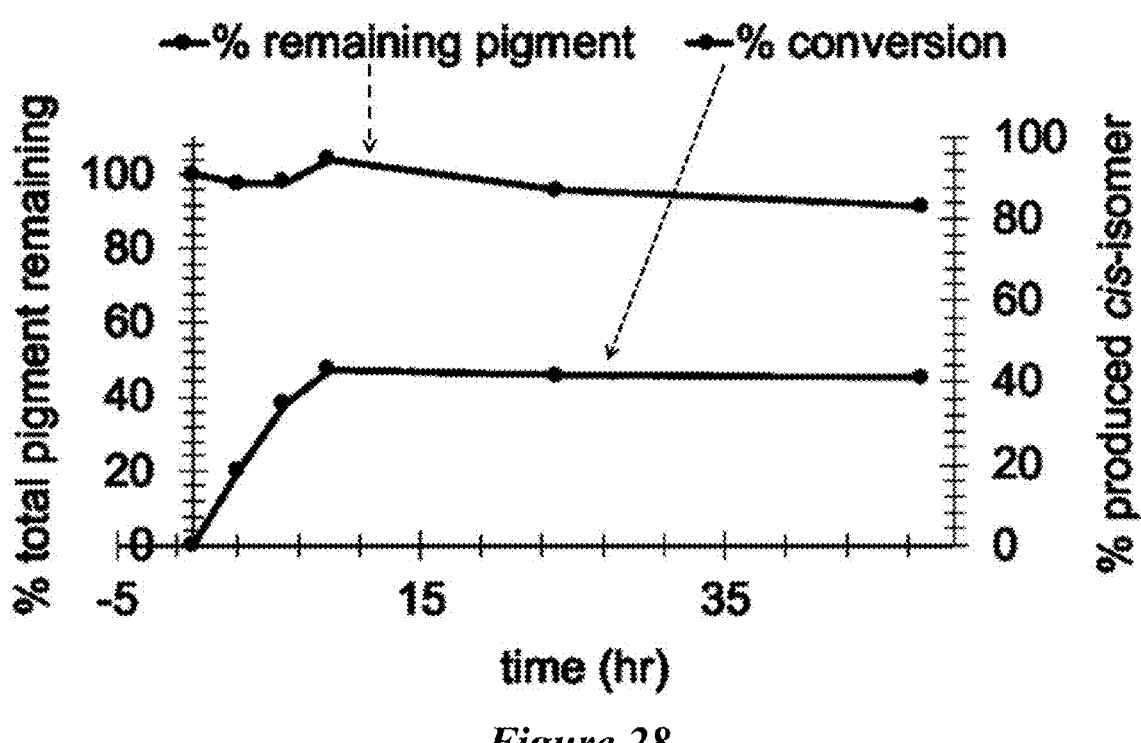
FIG. 28. Remaining pigment and % conversion from trans to cis when acylated delphinidin was exposed to the light box. The greatest conversion from trans to cis was observed after 9.5 hours when acylated delphinidin was exposed to irradiation from the light box, which included a D65 lamp (artificial sunlight), tungsten, and fluorescent lamp.

The greatest conversion from trans to cis was observed after 9.5 hours when acylated delphinidin was exposed to irradiation from the light box, which included a D65 lamp (artificial sunlight), tungsten, and fluorescent lamp (FIG. 28).

Figure 29:
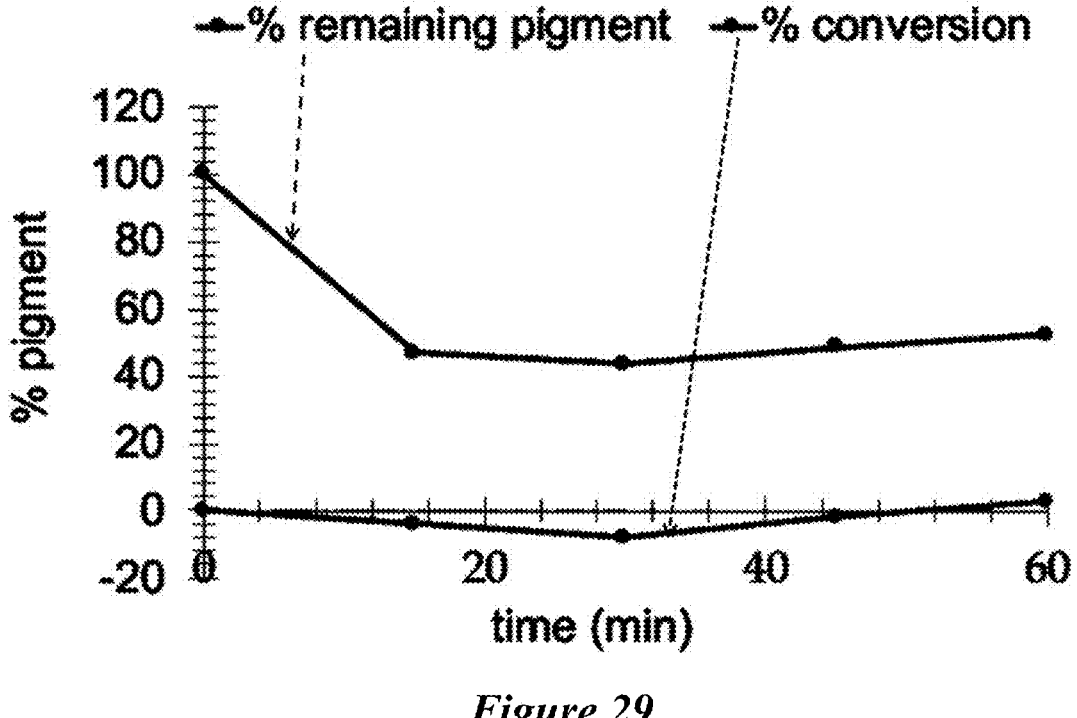
FIG. 29. Remaining pigment and % conversion from trans to cis when acylated delphinidin was exposed to UV treatment. The trans to cis-Delphinidin isomerization was negligible under UV irradiation. The total pigment content decreased immediately with UV treatment, most likely due to the concentration of light dispersion inside the chamber. Longer time points need to be tested.

The trans to cis-Delphinidin isomerization was negligible under UV irradiation (FIG. 29). The total pigment content decreased immediately with UV treatment, most likely due to the concentration of light dispersion inside the chamber. Longer time points need to be tested.

Figure 30:
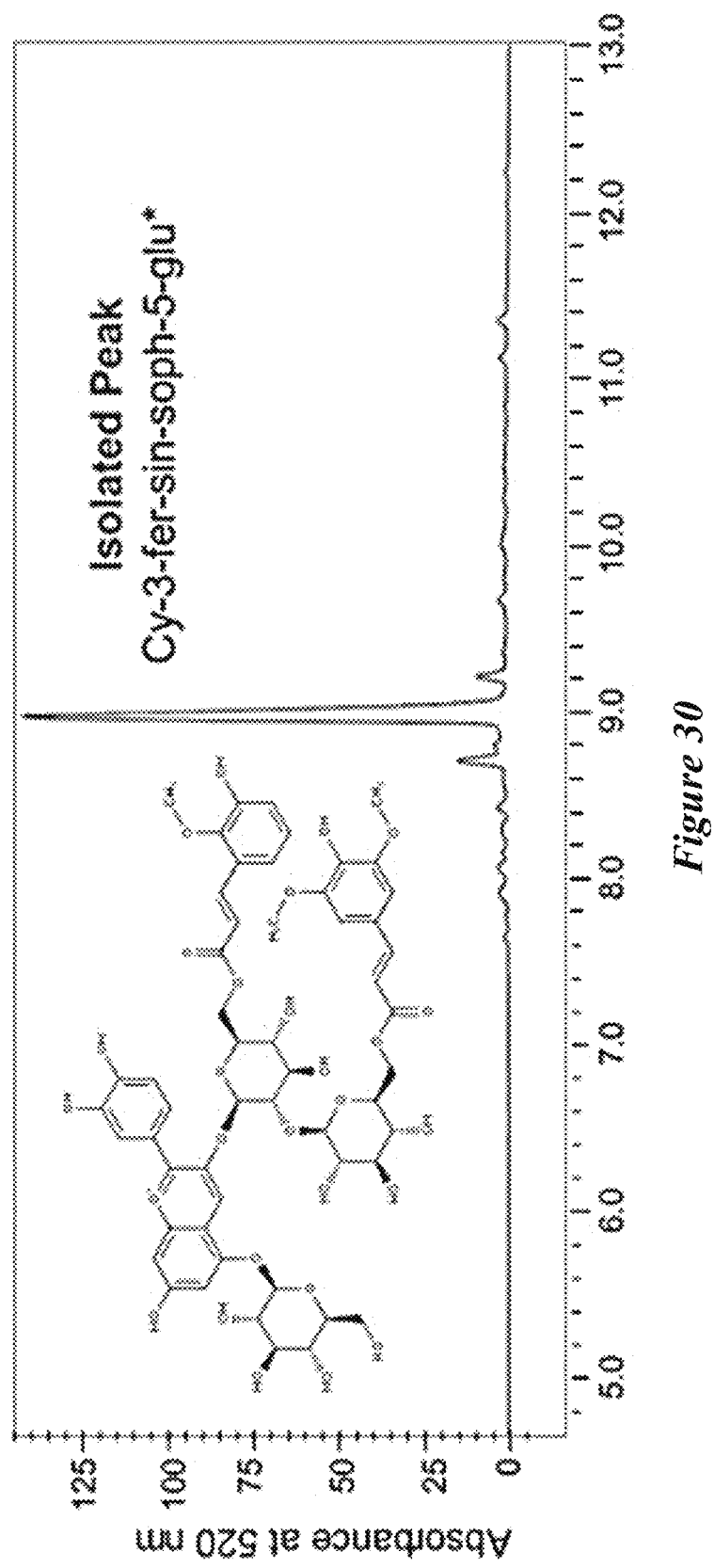
FIG. 30. HPLC chromatogram of the isolated di-acylated cyanidin (control: no light treatment).
Figure 31:
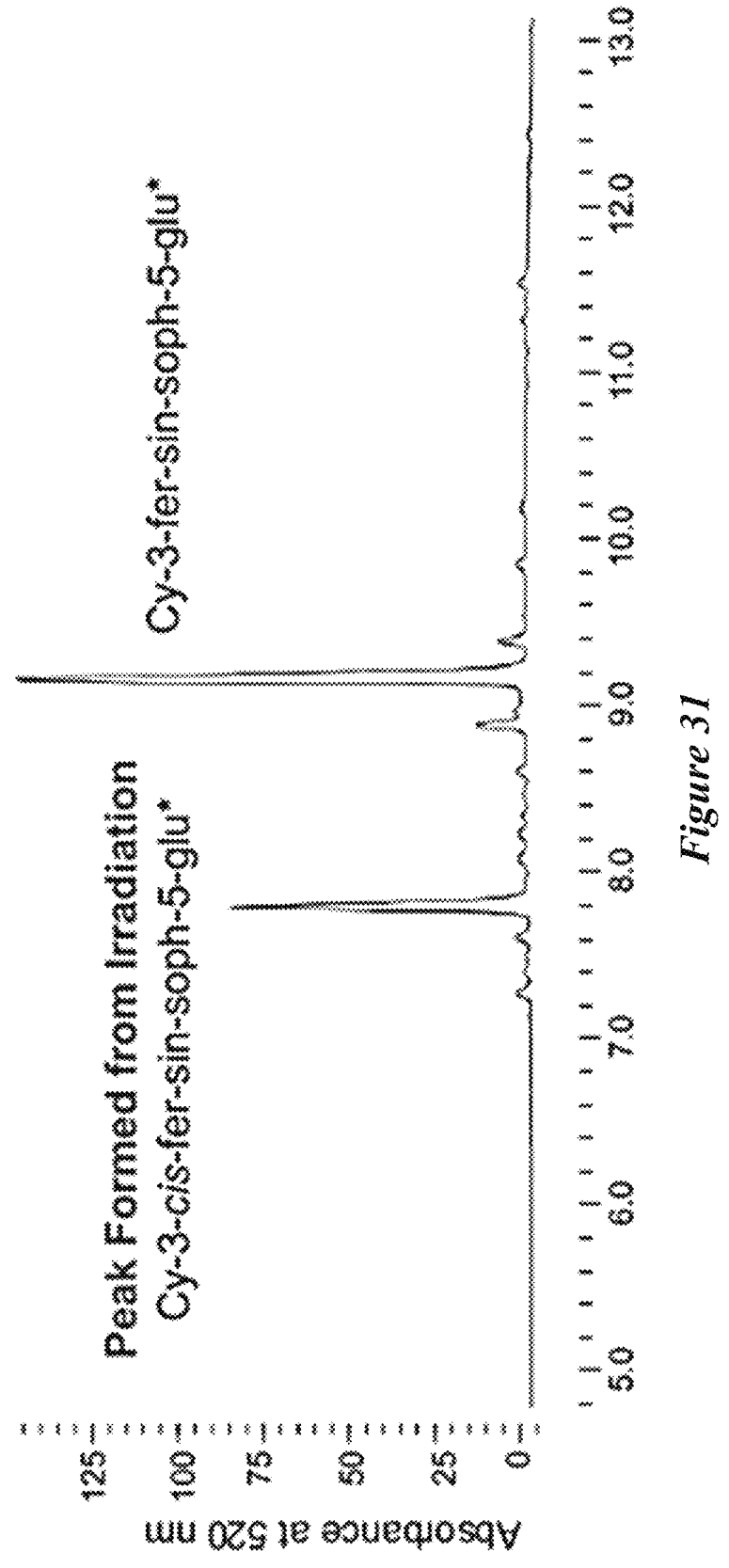
FIG. 31. HPLC chromatogram of the production of a new peak from 45 min of irradiation with 254 nm UV chamber.

HPLC chromatograms of the isolated di-acylated cyanidin (control: no light treatment) (FIG. 30) and the production of a new peak from 45 min of irradiation with 254 nm UV chamber (FIG. 31). This suggests that photoisomerization occurs with di-acylated ACN.

Figure 32:
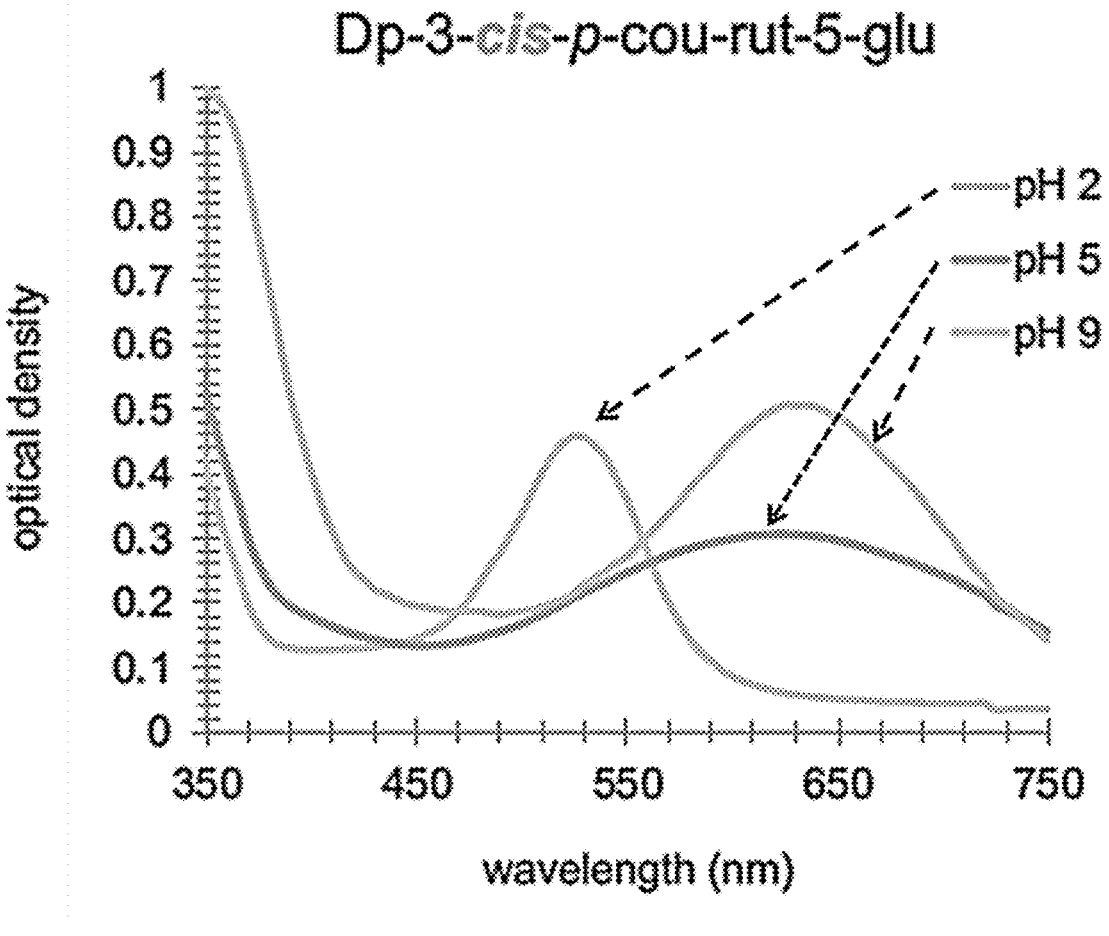
FIG. 32. Spectral distribution of cis-isomer in acidic, neutral, and alkaline pH.
Figure 33:
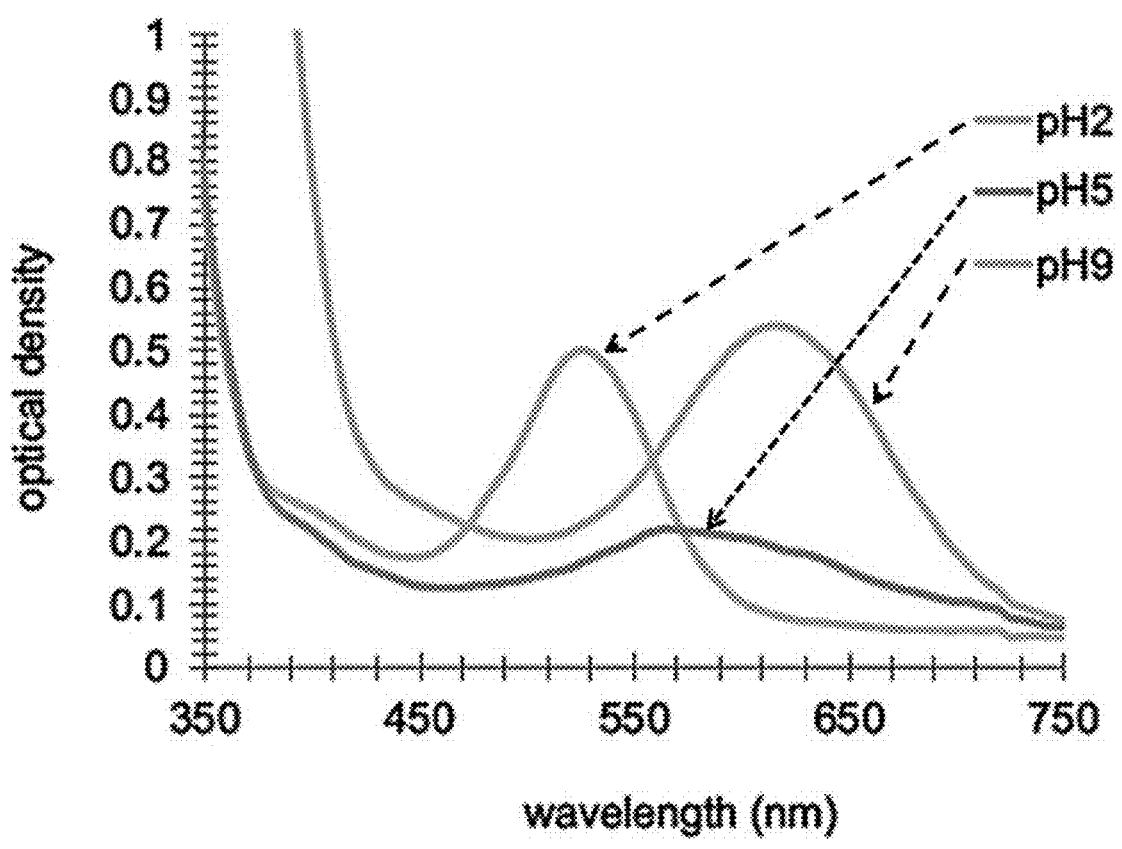
FIG. 33. Spectral distribution of trans-isomer in acidic, neutral, and alkaline pH.
Figure 34:
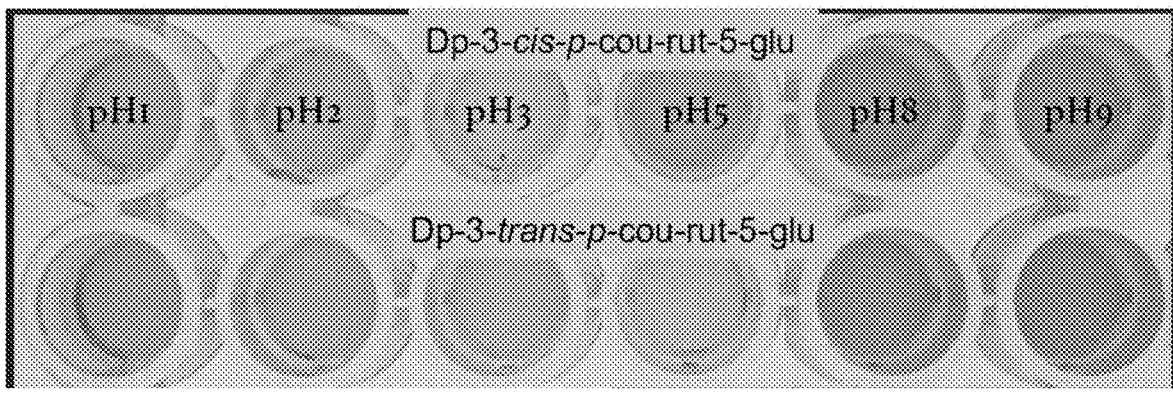
FIG. 34 shows the color expression of delphinidin (Dp)-3-cis-p-cou-rut-5-glu and Dp-3-trans-p-cou-rut-5-glu (top row and bottom row) from pH 1-pH 9 (left to right).

Spectral distribution of cis- and trans-isomers in acidic, neutral, and alkaline pH are shown in FIG. 32 and FIG. 33, respectively. FIG. 34 shows the color expression of delphinidin (Dp)-3-cis-p-cou-rut-5-glu and Dp-3-trans-p-cou-rut-5-glu (top row and bottom row) from pH 1-pH 9 (left to right).

Light box (D65, tungsten, and fluorescent lamp) produced greatest conversion with minimal total pigment degradation when the semi-purified extract was irradiated for 9.5 hours.

Sunlight generated maximal conversion at 73 hrs with minimal degradation at 13 hrs. Overall, sunlight produced considerable anthocyanin degradation due to its long irradiation time with negligible photoisomerization.

UV chamber irradiation at 365 nm produced negligible conversion with pigment degradation by half. This suggests that longer irradiation times must be tested.

Color characteristics and pigment stability of cis- and trans-isomer were different. cis-Acylated anthocyanin exhibited a distinct color range from its trans-counterpart, and in pH ranges typically challenging for anthocyanins.

In pH 4, cis-acylated delphinidin expressed color, whereas its trans-isomer bleached.

Diacylated ACN could also form a cis-isomer from its initial trans-configuration. Further studies must be done to determine the likelihood of photoisomerization based on type of acylating group and position.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The methods of the appended claims are not limited in scope by the specific methods described herein, which are intended as illustrations of a few aspects of the claims and any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

What is claimed is:

1. A method of making a photoisomerized composition, the method comprising:

irradiating a first composition comprising an anthocyanin dissolved in a solvent solution with UV light;

wherein the anthocyanin comprises cyanidin-3-p-coumaroyl-sambubioside-5-glucoside;

wherein at least a portion of the anthocyanin is present as a trans isomer before the irradiation;

wherein the solvent solution comprises ethanol and water in a ratio of ethanol to water (volume/volume) of from 90:10 to 80:20;

thereby converting at least a portion of trans isomer to a cis isomer via photoisomerization to produce the photoisomerized composition.

2. The method of claim 1, wherein the solvent solution comprises ethanol and water in a ratio of ethanol to water of 90:10 or 80:20.

3. The method of claim 1, wherein the UV light comprises light of one or more wavelengths of from 100 nm to 400 nm.

4. The method of claim 1, wherein the first composition is irradiated for an amount of time of from 1 minute to 60 minutes.

5. The method of claim 1, wherein the first composition comprises a crude extract derived from a plant dissolved in the solvent solution.

6. The method of claim 1, wherein the first composition comprises a crude extract derived from a raw agricultural product dissolved in the solvent solution.

7. The method of claim 1, wherein the first composition comprises a crude extract derived from an elderberry dissolved in the solvent solution.

8. The method of claim 1, wherein the anthocyanin is derived from a plant and/or a raw agricultural product.

9. The method of claim 1, wherein the anthocyanin is derived from an elderberry.

10. The method of claim 1, wherein the anthocyanin comprises an acylated anthocyanin.

11. The method of claim 1, wherein the anthocyanin comprises a cinnamic acid acylated anthocyanin.

12. The method of claim 1, wherein the first composition comprises the anthocyanin in a concentration of from 50 to 500 micromoles per liter (micromolar, μM).

13. The method of claim 1, wherein the cis isomer to the trans isomer are present in the photoisomerized composition in a ratio of greater than 0.5.

14. The method of claim 1, wherein the cis isomer is present in the photoisomerized composition in a concentration of 20 μM or more.

15. The method of claim 1, wherein the photoisomerized composition has improved color and stability relative to the first composition before irradiation.

16. The method of claim 1, wherein the photoisomerized composition has a more intense and stable blue color at pH 8 relative to the first composition before irradiation.

17. The method of claim 1, wherein the method further comprises making the first composition by dissolving the anthocyanin in the solvent solution.

18. A photoisomerized composition made using the method of claim 1.

19. A method of use of the photoisomerized composition of claim 18, the method comprising using the photoisomerized composition as a natural food dye, on an OTC coating, or in a cosmetic.

20. The method of claim 1, wherein the cis isomer to the trans isomer are present in the photoisomerized composition in a ratio of 0.65 or more.

* * * * *